US006395275B1

(12) United States Patent
Barbas et al.

(10) Patent No.: US 6,395,275 B1
(45) Date of Patent: May 28, 2002

(54) SYNTHETIC HUMAN NEUTRALIZING MONOCLONAL ANTIBODIES TO HUMAN IMMUNODEFICIENCY VIRUS

(75) Inventors: Carlos F. Barbas, San Diego; Dennis R. Burton; Richard A. Lerner, both of La Jolla, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 7 days.

(21) Appl. No.: 09/611,451

(22) Filed: Jul. 6, 2000

Related U.S. Application Data

(60) Division of application No. 08/591,632, filed on Feb. 20, 1996, now Pat. No. 6,261,558, which is a continuation of application No. PCT/US94/11907, filed on Oct. 19, 1994, which is a continuation-in-part of application No. 08/308, 841, filed on Sep. 19, 1994, now abandoned, which is a continuation-in-part of application No. 08/233,619, filed on Apr. 26, 1994, now abandoned, which is a continuation-in-part of application No. 08/139,409, filed on Oct. 19, 1993, now abandoned.

(51) Int. Cl.[7] .......................... A61K 39/42; G01N 33/53
(52) U.S. Cl. ............................... 424/148.1; 424/160.1; 435/975
(58) Field of Search .......................... 424/148.1, 160.1; 435/975

(56) References Cited

FOREIGN PATENT DOCUMENTS

| EP | 0 459 779 A1 | 4/1991 |
|---|---|---|
| WO | WO 91/19797 | 6/1991 |
| WO | WO 93/08216 | 10/1991 |

OTHER PUBLICATIONS

Pezella, et al., "Detection of the NEF Cellular Protein by Synthetic Monoclonal Antibody from HIV Infected Subjects", *International Conference on AIDS* 5: 633 (1989).
Posner, et al., "An IgC Human Monoclonal Antibody That Reacts with HIV–1/GP120, Inhibits Virus Binding to Cells, and Neutralizes Infection", *J. Immunol.* 146; 4325–4332 (1991).
Barbas, III, et al., "Assembly of combinatorial antibody libraries on phage surfaces: The gene III site", *Proc. Natl. Acad. Sci. USA* 88: 7978–7982 (1991).

Kang, et al., "Antibody redesign by chain shuffling from random combinatorial immunoglobin libraries", *Proc. Natl. Acad. Sci. USA* 88: 11120–11123 (1991).
Corey, et al., "An Investigation into the Minimum Requirements for Peptide Hydrolysis by Mutation of the Catalytic Triad of Trypsin", *J. Am. Chem. Soc.* 114: 1784–1790 (1992).
Zebedec, et al., "Human combinatorial antibody libraries to hepatitis B surface antigen", *Proc. Natl. Acad. Sci. USA* 89: 3175–3179 (1992).
Gram, et al., "In vitro selection and affinity maturation of antibodies from a naive combinatorial immunoglobin library", *Proc. Natl. Acad. Sci. USA* 89: 3576–3580 (1992).
Barbas, et al., "Semisynthetic combinatorial antibody libraries: A chemical solution to the diversity problem", *Proc. Natl. Acad. Sci. USA* 89: 4457–4461 (1992).
Burton, et al., "Antibodies from libraries", *Nature* 359: 782–783 (1992).
Burton, et al., "Human Antibodies to HIV–1 by Recombinant DNA Methods", *Chem. Immunol.* 56: 112–126 (1993).
Gorny, et al., "Repertoire of Neutralizing Human Monoclonal Antibodies Specific for the V3 Domain of HIV–1 gp120", *J. Immunol.* 150: 635–643 (1993).
Levy, et al., "Pathogenesis of Human Immunodefiency Virus Infection", *Microbiol. Rev.* 57: 183–289 (1993).
Moore, et al., "The HIV gp120–CD4 interaction: A target for pharmacological or immunological intervention?", *Perspect. Drug Disc. Design* 1: 235–250 (1993).
Williamson, et al., "Human monoclonal antibodies against a plethora of viral pathogens from single combinatorial libraries", *Proc. Natl. Acad. Sci. USA* 90: 4141–4145 (1993).
Riechmann, et al., "Phage Display and Selection of a Site–Directed Randomized Single–Chain Antibody Fv Fragment for Its Affinity Improvement", *Biochem.* 32: 8848–8855 (1993).

*Primary Examiner*—Mark Navarro
(74) *Attorney, Agent, or Firm*—Thomas E. Northrup; Thomas Fitting

(57) ABSTRACT

The present invention describes synthetic human monoclonal antibodies that immunoreact with and neutralize human immunodeficiency virus (HIV). The synthetic monoclonal antibodies of this invention exhibit enhanced binding affinity and neutralization ability to gp120. Also disclosed are immunotherapeutic and diagnostic methods of using the monoclonal antibodies, as well as cell lines for producing the monoclonal antibodies.

3 Claims, 18 Drawing Sheets

```
Fab         FR1                         CDR1     FR2              CDR2
M14  LEQSGAEVKKPGASVKVSCQASGYRFS       NFVIH    WVRQAPGQRFEWMG   WINPYNGNKEFSAKFQD
            FR3                             CDR3                 FR4
     RVTFTADTSANTAYMELRSLRSADTAVYYCAR  VGPYSWDDSPQDNYYMDV       WGKGTTVIVSS

Fab         FR1                         CDR1     FR2              CDR2
3b1  LEQSGAEVKKPGASVKVSCQASGYRFS       WFTLM    WVRQAPGQRFEWMG   WINPYNGNKEFSAKFQD
            FR3                             CDR3                 FR4
     RVTFTADTSANTAYMELRSLRSADTAVYYCAR  VGQWNWDDSPQDHYYMDV       WGKGTTVIVSS

Fab         FR1                         CDR1     FR2              CDR2
3b3  LEQSGAEVKKPGASVKVSCQASGYRFS       NFTVH    WVRQAPGQRFEWMG   WINPYNGNKEFSAKFQD
            FR3                             CDR3                 FR4
     RVTFTADTSANTAYMELRSLRSADTAVYYCAR  VGEWGWDDSPQDNYYMDV       WGKGTTVIVSS

Fab         FR1                         CDR1     FR2              CDR2
3b4  LEQSGAEVKKPGASVKVSCQASGYRFS       NYTLI    WVRQAPGQRFEWMG   WINPYNGNKEFSAKFQD
            FR3                             CDR3                 FR4
     RVTFTADTSANTAYMELRSLRSADTAVYYCAR  VGPWNWDSPQDNYYMDV        WGKGTTVIVSS

Fab         FR1                         CDR1     FR2              CDR2
3b9  LEQSGAEVKKPGASVKVSCQASGYRFS       NFTVH    WVRQAPGQRFEWMG   WINPYNGNKEFSAKFQD
            FR3                             CDR3                 FR4
     RVTFTADTSANTAYMELRSLRSADTAVYYCAR  VGPWRWDDSPQDNYYMDV       WGKGTTVIVSS
```

FIG. 1

```
Fab        FR1                    CDR1           FR2              CDR2
MT4  ELTQSPGTLSLSPGERATFSC       RSSHSTRSRRVA   WYQHKPGQAPRLVIH  GVSNRAS
           FR3                             CDR3              FR4
     GTSDRFSGSGSGTDFTLTTTRVEPEDFALYYC  QVYGASSYT       FGQGTKLERKRT
```

FIG. 2

```
                10                    20                    30                         40
CTC GAG CAG TCT GGG GCT GAG GTG AAG AAG CCT GGG GCC TCA GTG AAG 50              60              70              80              90
GTT TCT TGT CAA GCT TCT GGA TAC AGA TTC AGT AAC TTT GTT ATT CAT 100             110             120             130             140
TGG GTG CGC CAG GCC CCC GGA CAG AGG TTT GAG TGG ATG GGA TGG ATC 150             160             170             180             190
AAT CCT TAC AAC GGA AAC AAA GAA TTT TCA GCG AAG TTC CAG GAC AGA 200             210             220             230             240
GTC ACC TTT ACC GCG GAC ACA TCC GCG AAC ACA GCC TAC ATG GAG TGG 250             260             270             280
AGG AGC CTC AGA TCT GCA GAC ACG GCT GTT TAT TAT TGT GCG AGA GTG 290             300             310             320             330
GGG CCA TAT AGT TGG GAT GAT TCT CCC CAG GAC AAT TAT TAT ATG GAC 340             350             360             370
GTC TGG GGC AAA GGG ACC ACG GTC ATC GTC TCC TCA
```

| Experiment A | | | | | | Experiment B | | | | | |
|---|---|---|---|---|---|---|---|---|---|---|---|
| CDR1 | | | | | | CDR1 | | | | CDR3 | |
| 31 | 32 | 33 | 34 | 35 | | 31 | 32 | 33 | 34 | 35 | | 96 | 97 | 98 | 99 | |
| N | F | V | I | H | (SEQ ID NO 8) | N | F | T | L | M | (SEQ ID NO 26) | P | Y | S | W | (SEQ ID NO 34) MT4 |
| R | Y | T | V | F | (SEQ ID NO 14) | N | Y | T | I | M | (SEQ ID NO 27) | Q | W | N | W | (SEQ ID NO 35) 3b1 |
| N | W | S | V | M | (SEQ ID NO 15) | N | F | T | V | H | (SEQ ID NO 28) | P | W | T | W | (SEQ ID NO 36) 3b2 |
| G | Y | T | L | L | (SEQ ID NO 16) | N | Y | T | L | I | (SEQ ID NO 29) | E | W | G | W | (SEQ ID NO 37) 3b3 |
| N | F | T | L | M | (SEQ ID NO 17) | N | F | H | I | M | (SEQ ID NO 30) | P | W | N | W | (SEQ ID NO 38) 3b4 |
| H | Y | S | L | M | (SEQ ID NO 18) | N | F | S | H | M | (SEQ ID NO 31) | L | W | N | W | (SEQ ID NO 39) 3b6 |
| N | W | S | V | H | (SEQ ID NO 19) | N | Y | T | H | Q | (SEQ ID NO 32) | S | W | R | W | (SEQ ID NO 40) 3b7 |
| N | F | S | I | M | (SEQ ID NO 20) | N | F | T | V | H | (SEQ ID NO 33) | P | Y | S | W | (SEQ ID NO 41) 3b8 |
| N | F | A | I | H | (SEQ ID NO 21) | | | | | | | P | W | R | W | (SEQ ID NO 42) 3b9 |
| N | F | T | M | V | (SEQ ID NO 22) | | | | | | | | | | | |
| N | F | T | L | Q | (SEQ ID NO 23) | | | | | | | | | | | |
| Y | F | T | M | H | (SEQ ID NO 24) | | | | | | | | | | | |
| S | Y | P | L | H | (SEQ ID NO 25) | | | | | | | | | | | |

| FAB | FR1 | CDR1 | FR2 | CDR2 |
|---|---|---|---|---|
| MT4 | LEQSGAEVKKPGASVKVSCQASGYRFS | NFVIH | WVRQAPGQRFEWMG | WINPYNGNKEFSAKFQD |
| H4H1-1 | = | HFTVH | = | = |
| H4H1-3 | = | HFTLH | = | = |
| H4H1-5 | = | HFTIM | = | = |
| H4H1-6 | = | NYTLQ | = | = |
| H4H1-7 | = | NFTLI | = | = |
| H4H1-8 | = | NWTIM | = | = |

FIG. 7A

| FR3 | CDR3 | FR4 | SEQ ID NO. |
|---|---|---|---|
| RVTFTADTSANTAYMELRSLRSADTAVYYCAR | VGPYSWDDSPQDNYYMDV | WGKGTTVIVSS | 1 |
| = | = | = | 45 |
| = | = | = | 46 |
| = | = | = | 47 |
| = | = | = | 48 |
| = | = | = | 49 |
| = | = | = | 50 |

FIG. 7B

| FAB | FR1 | CDR1 | FR2 | CDR2 |
|---|---|---|---|---|
| 3b3 | LEQSGAEVKKPGASVKVSCQASGYRFS | NFTVH | WVRQAPGQRFEWMG | WINPYNGNKEFSAKFQD |
| M556-2 | = | = | = | = |
| M556-3 | = | = | = | = |
| M556-7 | = | = | = | = |
| M556-10 | = | = | = | = |
| M556-15 | = | = | = | = |
| M556-16 | = | = | = | = |
| M556-5 | = | = | = | = |
| M556-13 | = | = | = | = |

FIG. 9A

| FR3 | CDR3 | FR4 | SEQ ID NO. |
|---|---|---|---|
| RVTFTADTSANTAYMELRSLRSADTAVYYCAR | VGEWGWDDSPQDNYYMDV | WGKGTTVIVSS | 3 |
| " | VGEWGWEQFRFDNYYMDV | " | 54 |
| " | VGEWGWEMFRYDNYYMDV | " | 55 |
| " | VGEWGWEMRRFDNYYMDV | " | 56 |
| " | VGEWGWHQRRYDNYYMDV | " | 57 |
| " | VGEWGWTQRRFDNYYMDV | " | 58 |
| " | VGEWGWDQVRYDNYYMDV | " | 59 |
| " | VGEWGWDQRRYDNYYMDV | " | 60 |
| " | VGEWGWEMAIQDNYYMDV | " | 61 |

FIG. 9B

```
        10              20              30              40
         *               *               *               *
GAG CTC ACG CAG TCT CCA GGC ACC CTG TCT CTG TCT CCA GGG AAA AGA 50              60              70              80              90
  *               *               *               *               *
GCC ACC TTC TCC TGT AGG TCC AGT CAC AGC ATT CGC AGC CGC CGC GTA 100             110             120             130             140
    *               *               *               *               *
GCC TGG TAC CAG CAC AAA CCT GGC CAG GCT CCA AGG CTG GTC ATA CAT 150             160             170             180             190
      *               *               *               *               *
GGT GTT TCC AAT AGG GCC TCT GGC ATC TCA GAC AGG TTC AGC GGC AGT 200             210             220             230             240
        *               *               *               *               *
GGG TCT GGG ACA GAC TTC ACT CTC ACC ATC ACC AGA GTG GAG CCT GAA 250             260             270             280
          *               *               *               *
GAC TTT GCA CTG TAC TAC TGT CAG GTC TAT GGT GCC TCC TCG TAC ACT 290             300             310             320
  *               *               *               *
TTT GGC CAG GGG ACC AAA CTG GAG AGG AAA CGA ACT
```

FIG. 10

| FAB 3b3 (or 4L) | FR1 | CDR1 | FR2 | CDR2 |
|---|---|---|---|---|
| | ELTQSPGTLSLSPGERATFSC | RSSHSIRSRRVA | WYQHKPGQAPRLVIH | GVSNRAS |
| A | = | RSSHKEFGRRVA | = | = |
| B | = | RSSHTVYRDRVA | = | = |
| C | = | RSSHPLHRARVA | = | = |
| D | = | RSSHQLDGSRVA | = | = |

FIG. 11A

| FR3 | CDR3 | FR4 | SEQ ID NO. |
|---|---|---|---|
| GISDRFSGSGSGTDFTLTITRVEPEDFALYYC | QVYGASSYT | FGQGTKLERKRT | 6 |
| = | = | = | 67 |
| = | = | = | 68 |
| = | = | = | 69 |
| = | = | = | 70 |

FIG. 11B

| FAB | FR1 | CDR1 | FR2 | CDR2 |
|---|---|---|---|---|
| 3b3 | ELTQSPGTLSLSPGERATFSC | RSSHSIRSRRVA | WYQHKPGQAPRLVIH | GVSNRAS |
| H4L3-2 | " | " | " | " |
| H4L3-3 | " | " | " | " |
| H4L3-4 | " | " | " | " |

FIG. 12A

| | FR3 | CDR3 | FR4 | SEQ ID NO. |
|---|---|---|---|---|
| | GISDRFSGSGSGTDFTLTITRVEPEDFALYYC | QVYGASSYT | FGQGTKLERKRT | 6 |
| | " | QQYGWPFYT | " | 73 |
| | " | QVYGGSAYT | " | 74 |
| | " | QKYGGGTYT | " | 75 |

FIG. 12B

| FAB | FR1 | CDR1 | FR2 | CDR2 |
|---|---|---|---|---|
| Fab D | ELTQSPGTLSLSPGERATFSC | RSSHQLDGSRVA | WYQHKPGQAPRLVIH | GVSNRAS |
| QA1 |  |  | = | = |
| QA2 |  |  | = | = |
| QA3 |  |  | = | = |
| QA4 |  |  | = | = |
| QA5 |  |  | = | = |
| QA6 |  |  | = | = |
| QA7 |  |  | = | = |
| QA8 |  |  | = | = |
| QA9 |  |  | = | = |
| QA10 |  |  | = | = |
| QA11 (or LH) |  |  | = | = |
| QA12 |  |  | = | = |

FIG. 13A

| FR3 | CDR3 | FR4 | SEQ ID NO. |
|---|---|---|---|
| GISDRFSGSGSGTDFTLTITRVEPEDFALYYC | QVYGASSYT | FGQGTKLERKRT | 70 |
| " | QVYGWSQYT | " | 76 |
| " | QLYGRGNYT | " | 77 |
| " | QTYGRGVYT | " | 78 |
| " | QSYGGRDYT | " | 79 |
| " | QTYGWSGYT | " | 80 |
| " | QKYGDSFYT | " | 81 |
| " | QMYGGRDYT | " | 82 |
| " | QQYGDSLYT | " | 83 |
| " | QMYGGFTYT | " | 84 |
| " | QTYGRGSYT | " | 85 |
| " | QTYGRGHYT | " | 86 |
| " | QTYGRGIYT | " | 87 |

| LIGHT CHAIN | FR1 | CDR1 | FR2 | CDR2 |
|---|---|---|---|---|
| L42 | ELTQSPGTLSLSPGERATFSC | RSSHQLDGSRVA | WYQHKPGQAPRLVIH | GVSNRAS |

FIG. 14B

| FR3 | CDR3 | FR4 | SEQ ID NO. |
|---|---|---|---|
| GISDRFSGSGSGTDFTLTITRVEPEDFALYYC | QQYGWPFYT | FGQGTKLERKRT | 88 |

| HEAVY CHAIN | FR1 | CDR1 | FR2 | CDR2 |
|---|---|---|---|---|
| H31 | LEQSGAEVKKPGASVKVSCQASGYRFS | HFTVH | WVRQAPGQRFEWHG | WINPYNGNKEFSAKFQD |
| H33 | " | HFTLH | " | " |
| H101 | " | HFTVH | " | " |
| H103 | " | HFTLH | " | " |

FIG. 15A

| | FR3 | CDR3 | FR4 | SEQ ID NO. |
|---|---|---|---|---|
| | RVTFTADTSANTAYMELRSLRSADTAVYYCAR | VGEWGWEMFRYDNYYMDV | WGKGTTVIVSS | 89 |
| | " | VGEWGWEMFRYDNYYMDV | " | 90 |
| | " | VGEWGWHQRRYDNYYMDV | " | 91 |
| | " | VGEWGWHQRRYDNYYMDV | " | 92 |

FIG. 15B

SYNTHETIC HUMAN NEUTRALIZING MONOCLONAL ANTIBODIES TO HUMAN IMMUNODEFICIENCY VIRUS

This application is a divisional of U.S. application Ser. No. 08/591,632, filed Feb. 20, 1996, now U.S. Pat. No. 6,261,558, which is a continuation of PCT/US94/11907, filed Oct. 19, 1994, which is a continuation-in-part of U.S. application Ser. No. 08/308,841, filed Sep. 19, 1994, now abandoned, which is a continuation-in-part of U.S. application Ser. No. 08/233,619, filed Apr. 26, 1994, now abandoned, which is a continuation-in-part of U.S. application Ser. No. 08/139,409, filed Oct. 19, 1993, now abandoned.

This invention was made with government support under Contract No. AI33292 by the National Institutes of Health. The government has certain rights in the invention.

TECHNICAL FIELD

The present invention relates generally to the field of immunology and specifically to synthetic human monoclonal antibodies that bind and neutralize human immunodeficiency virus (HIV).

BACKGROUND

1. HIV Immunotherapy

HIV is the focus of intense studies as it is the causative agent for acquired immunodeficiency syndrome (AIDS). Immunotherapeutic methods are one of several approaches to prevention, cure or remediation of HIV infection and HIV-induced diseases. Specifically, the use of neutralizing antibodies in passive immunotherapies is of central importance to the present invention.

Passive immunization of HIV-1 infected humans using human sera containing polyclonal antibodies immunoreactive with HIV has been reported. See for example, Jackson et al., Lancet, Sep. 17:647–652, (1988); Karpas et al., *Proc. Natl. Acad. Sci., USA*, 87:7613–7616 (1990).

Numerous groups have reported the preparation of human monoclonal antibodies that neutralize HIV isolates in vitro. The described antibodies typically have immunospecificities for epitopes on the HIV glycoprotein gp160 or the related glycoproteins gp120 or gp41. See, for example Karwowska et al., *Aids Research and Human Retroviruses*, 8:1099–1106 (1992); Takeda et al., *J. Clin. Invest.*, 89:1952–1957 (1992); Tilley et al., *Aids Research and Human Retroviruses*, 8:461–467 (1992); Laman et al., *J. Virol.*, 66:1823–1831 (1992); Thali et al., *J. Virol.*, 65:6188–6193 (1991); Ho et al., *Proc. Natl. Acad. Sci., USA*, 88:8949–8952 (1991); D'Souza et al., *AIDS*, 5:1061–1070 (1991); Tilley et al., *Res. Virol.*, 142:247–259 (1991); Broliden et al., *Immunol.*, 73:371–376 (1991); Matour et al., *J. Immunol.*, 146:4325–4332 (1991); and Gorny et al., *Proc. Natl. Acad. Sci., USA*, 88:3238–3242 (1991). For a current review of pathogenesis of HIV infection and therapeutic modalities including the use of passive immunity with anti-HIV antibodies, see Levy, *Microbiol. Rev.*, 57:183–289 (1993).

To date, none of the reported human monoclonal antibodies have been shown to be effective in passive immunization therapies. Further, as monoclonal antibodies, they all each react with an individual epitope on the HIV envelope surface glycoproteins, gp120 or gp160, or against the V3 loop of gp120 or against the envelope transmembrane glycoprotein, gp41. The epitope against which an effective neutralizing antibody immunoreacts has not been identified.

There continues to be a need to develop human monoclonal antibody preparations with significant HIV neutralization activity. In addition, there is a need for monoclonal antibodies immunoreactive with additional and diverse neutralizing epitopes on HIV gp120. Additional (new) epitope specificities are required because, upon passive immunization, the administered patient can produce an immune response against the administered antibody, thereby inactivating the particular therapeutic antibody.

Furthermore, the well documented ability of HIV to mutate its envelope glycoprotein structure and thereby alter its reactivity with the immune system of an infected host produces variant "field isolates" which compromise the utility of individual antibody preparations immunoreactive with an individual laboratory strain of HIV. Existing antibody preparations tend to be less potent against primary field isolates of HIV than against laboratory strains. Moore et al., *Perspectives in Drug Discovery and Design*, 1:235–250 (1993). In addition, no reported human monoclonal antibody has been shown to be effective at neutralizing multiple strains of HIV. Therefore, there also continues to be a need for a human monoclonal antibody with the ability to neutralize multiple different strains of HIV.

2. Human Monoclonal Antibodies Produced from Combinatorial Phagemid Libraries

The use of filamentous phage display vectors, referred to as phagemids, has been repeatedly shown to allow the efficient preparation of large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries. Kang et al., *Proc. Natl. Acad. Sci., USA*, 88:4363–4366 (1991). Combinatorial libraries of antibodies have been produced using both the cpVIII membrane anchor (Kang et al., *Proc. Natl. Acad. Sci., USA*, 88:4363–4366, 1991) and the cpIII membrane anchor. Barbas et al., *Proc. Natl. Acad. Sci., USA*, 88:7978–7982 (1991).

The diversity of a filamentous phage-based combinatorial antibody library can be increased by shuffling of the heavy and light chain genes (Kang et al., *Proc. Natl. Acad. Sci. USA*, 88:11120–11123, 1991), by altering the CDR3 regions of the cloned heavy chain genes of the library (Barbas et al., *Proc. Natl. Acad. Sci., USA*, 89:4457–4461, 1992), and by introducing random mutations into the library by error-prone polymerase chain reactions (PCR). Gram et al., *Proc. Natl. Acad. Sci., USA*, 89:3576–3580 (1992).

Filamentous phage display vectors have also been utilized to produce human monoclonal antibodies immunoreactive with hepatitis B virus (HBV) or HIV antigens. See, for example Zebedee et al., *Proc. Natl. Acad. Sci., USA*, 89:3175–3179 (1992); and Burton et al., *Proc. Natl. Acad. Sci., USA*, 88:10134–10137 (1991), respectively. Human monoclonal antibodies displayed on the surface of bacteriophage through the use of phage vectors, where the antibodies are specific for HIV-1 antigens, gp120 and gp41, have been generated through screening of combinatorial libraries. The resultant antibodies have been shown to be immunoreactive with HIV and to neutralize HIV. See, Barbas et al., *J. Mol. Biol.*, 230:812–823 (1993); Williamson et al., *Proc. Natl. Acad. Sci., USA*, 90:4141–4145 (1993); Burton et al., *Chem. Immunol.*, 56:112–126 (1993); and Barbas et al., *Proc. Natl. Acad. Sci., USA*, 89:9339–9343 (1992).

While the above-described phage display-derived anti-HIV antibodies have been shown to neutralize HIV infection, the screened antibodies are representative of the immune repertoire of an immunized or infected host. However, the heavy and light chain pairings isolated for their affinity for an antigen in vitro are not necessarily paired in vivo. Although the phage display system allows for unique pairing of heavy and light chains, in many cases affinity selection restores the approximate pairings. Burton et al., *Nature,* 359:782–783 (1992). While such immunized sources or immune priming by natural infection provides useful antibody libraries for some antigens, it is not always possible to acquire such libraries.

Although anti-HIV-1 neutralizing antibodies have been obtained through screening of phage libraries prepared from HIV-1 positive donors, the resultant antibodies are limited in specificity and affinity by the heavy and light chain amino acid residue sequences.

The diversity of a filamentous phage-based combinatorial antibody library, however, can be increased by shuffling of the heavy and light chain genes obtained from an initial screen of a library (Kang et al., *Proc. Natl. Acad. Sci., USA,* 88:11120–11123, 1991). Another approach is to introduce random mutations into the heavy and light chain genes by error-prone polymerase chain reactions (PCR). Gram et al., *Proc. Natl. Acad. Sci., USA,* 89:3576–3580, 1992). Mutagenesis of proteins has been utilized to alter the function, and in some cases the binding specificity, of a protein. Typically, the mutagenesis is site-directed, and therefore laborious depending on the systematic choice of mutation to induce in the protein. See, for example Corey et al., *J. Amer. Chem. Soc.,* 114:1784–1790 (1992), in which rat trypsins were modified by site-directed mutagenesis. More recently, Riechmann et al., *Biochem.,* 32:8848–8855 (1993), described the use of site-directed mutagenesis and phage display techniques prior to screening the randomized library to increase the affinity of a single-chain Fab fragment specific for the hapten 2-phenyloxazol-5-one.

A preferred approach, in order to more extensively sample the potential of antibody structure and function, is the preparation of semisynthetic antibodies in the context of phage display. In these molecules, one or more of the complementarity determining regions (CDR) of the cloned heavy or light chain genes obtained from screening of the library are altered resulting in new variable domain amino acid residue sequences. Barbas et al., *Proc. Natl. Acad. Sci., USA,* 89:4457–4461 (1992). Unlike antibodies cloned from a particular donor, semisynthetic antibodies can have CDR of any size with any sequence, thereby increasing the potential to obtain antibodies having new specificities and affinities.

BRIEF DESCRIPTION OF THE INVENTION

Synthetic Fab heterodimers specific for HIV-1 glycoproteins having enhanced affinity, specificity and neutralizing capacities as compared to the previously characterized antibodies have now been discovered. The new synthetic HIV-1-specific Fab heterodimers are obtained through the use of the synthetic method of randomly mutagenizing the complementarity determining regions (CDR) of the heavy and light chain genes encoding a recombinant Fab antibody to produce an antibody that binds to and neutralizes HIV.

The randomly mutagenized neutralizing antibodies define new epitopes on HIV, particularly on HIV glycoprotein gp120, thereby increasing the availability of new immunotherapeutic human monoclonal antibodies that exhibit higher affinity binding to the epitope as compared to antibodies selected from a nonrandomized combinatorial library.

The invention provides synthetic human monoclonal antibodies that neutralize HIV more efficiently than antibodies selected from non-randomized combinatorial libraries. Also provided are amino acid sequences which confer the enhanced neutralization function to the antigen binding domain of a monoclonal antibody, and which can be used immunogenically to identify other antibodies that specifically bind and neutralize HIV. The synthetic monoclonal antibodies of the invention find particular utility as reagents for the diagnosis and immunotherapy of HIV-induced disease.

A major advantage of the monoclonal antibodies of the invention derives from the fact that they are encoded by a human polynucleotide sequence, i.e., they are human antibodies. Thus, in vivo use of the monoclonal antibodies of the invention for diagnosis and immunotherapy of HIV-induced disease greatly reduces the problems of significant host immune response to the passively administered antibodies which is a problem commonly encountered when monoclonal antibodies of xenogeneic or chimeric derivation are utilized.

Another major advantage of the human monoclonal antibodies of the present invention is that the antibodies have dramatically increased immunoaffinity for the target antigen, making the antibodies particularly potent both diagnostically and therapeutically.

In one embodiment, the invention contemplates a synthetic human monoclonal antibody capable of immunoreacting with and neutralizing human immunodeficiency virus (HIV). A synthetic monoclonal antibody has the capacity to reduce HIV infectivity titer in an in vitro virus infectivity assay by 50% at a concentration of less than 100 nanograms (ng) of antibody per milliliter (ml) of culture medium in the assay. In preferred embodiments, the monoclonal antibody reduces infectivity titers 50% at a concentration is less than 20 ng/ml, and preferably less than 10 ng/ml.

A preferred synthetic monoclonal antibody is a Fab fragment. More preferred are synthetic monoclonal antibody molecules that immunoreact with an HIV glycoprotein, particularly the HIV glycoprotein gp120.

The invention also describes human monoclonal antibodies, and their method of preparation, which exhibit enhanced or improved virus neutralization capacity for multiple different strains of HIV, i.e., increased breadth of virus strain neutralizing capacity. Thus, a preferred human monoclonal antibody has the ability to neutralize a preselected first HIV strain as described above, and further has the capacity to reduce the HIV infectivity titer of a second field strain of HIV in the in vitro virus infectivity assay by 50% at a concentration of less than 10 micrograms (ug) of antibody per milliliter (ml). By neutralizing multiple strains of HIV, the present antibodies exhibit strain crossreactivity and multi-strain neutralizing abilities.

A preferred synthetic human monoclonal antibody has the binding specificity of a monoclonal antibody comprising a heavy chain immunoglobulin variable region amino acid residue sequence selected from the group consisting of SEQ ID NOs 2, 3, 4 and 5. Another preferred synthetic human monoclonal antibody has the binding specificity of a monoclonal antibody comprising a light chain immunoglobulin variable region amino acid residue sequence in SEQ ID NO 6.

In preferred embodiment, the invention describes the neutralizing antibodies as being immunoreactive with HIV glycoprotein gp120 with a dissociation constant ($K_d$) of about $1\times10^{-8}$ M or less, preferably from about $1\times10^{-9}$ M to about $1\times10^{-30}$ M, more preferably from about $1\times10^{-10}$ M to about $1\times10^{-11}$ M, and most preferably from about $1\times10^{-11}$ M to about $1\times10^{-12}$ M.

A preferred human monoclonal antibody having the above high-affinity binding specificity comprises a heavy chain immunoglobulin variable region amino acid residue sequence selected from the group consisting of SEQ ID NOs 1, 2, 3, 4, 5, 54, 55, 56, 57, 58, 59, 89, 90, 91 and 92, and conservative substitutions thereof. In addition, a preferred human monoclonal antibody having the above high-affinity binding specificity comprises a light chain immunoglobulin variable region amino acid residue sequence selected from the group consisting of SEQ ID NOs 6, 69, 70, 73, 75, 76, 77, 79, 80, 82, 83, 84, 85, 86, 87 and 88, and conservative substitutions thereof. Particularly preferred is a human monoclonal antibody wherein the monoclonal antibody has the binding specificity of a monoclonal antibody having heavy and light chain immunoglobulin variable region amino acid residue sequences in pairs selected from the group consisting of SEQ ID NOs 2:6, 3:6, 4:6, 5:6, 3:69, 3:70, 3:73, 3:75, 3:76, 3:77, 3:79, 3:80, 3:82, 3:83, 3:84, 3:85, 3:86, 3:87, 54:6, 55:6, 56:6, 57:6, 58:6, 59:6, 89:6, 89:88, 90:86, 90:88, 91:6, 91:88 and 92:88, and conservative substitutions thereof.

Also contemplated are methods of producing a synthetic anti-HIV monoclonal antibody using random mutagenesis methods for sequentially mutagenizing one or more preselected domains of the immunoglobulin heavy chain, preferably a complementarity determining region (CDR), and subsequently selecting for antibodies which strongly immunoreact with and neutralize HIV.

In another embodiment, the invention describes a polynucleotide sequence encoding a heavy or light chain immunoglobulin variable region amino acid residue sequence portion of a synthetic human monoclonal antibody of this invention. Also contemplated are DNA expression vectors containing the polynucleotide, and host cells containing the vectors and polynucleotides of the invention.

The invention also contemplates a method of detecting human immunodeficiency virus (HIV) comprising contacting a sample suspected of containing HIV with a diagnostically effective amount of the synthetic monoclonal antibody of this invention, and determining whether the synthetic monoclonal antibody immunoreacts with the sample. The method can be practiced in vitro or in vivo, and may include a variety of methods for determining the presence of an immunoreaction product.

In another embodiment, the invention describes a method for providing passive immunotherapy to human immunodeficiency virus (HIV) disease in a human, comprising administering to the human an immunotherapeutically effective amount of the synthetic monoclonal antibody of this invention. The administration can be provided prophylactically, and by a parenteral administration. Pharmaceutical compositions containing one or more of the different synthetic human monoclonal antibodies are described for use in the therapeutic methods of the invention.

BRIEF DESCRIPTION OF THE DRAWINGS

In the drawings forming a portion of this disclosure:

FIG. 1 illustrates the amino acid residue sequences of variable heavy ($V_H$) domains of human Fabs binding to gp120. The Fab heterodimer designations corresponding to the DNA clone from which the Fabs are expressed are indicated in the left hand column. The Fabs, MT4, 3b1, 3b3, 3b4 and 3b9, have been respectively assigned SEQ ID NOs 1–5 and are listed as such in the Sequence Listing. Fab MT4 is expressed from the original clone selected from a plasmid library generated from patient MT. The library was screened against gp120 as described in Example 1A. The synthetic human HIV-1 neutralizing Fabs, 3b1, 3b3, 3b4 and 3b9, are the Fabs that resulted from randomizing CDR1 and CDR3 of the heavy chain as described in Example 1, specifically Examples 1B and 1E. The sequenced regions of each Fab listed from left to right are framework region 1 (FR1), complementary determining region 1 (CDR1), framework region 2 (FR2), complementary determining region 2 (CDR2), framework region 3 (FR3), complementary determining region 3 (CDR3), and framework region 4 (FR4).

FIG. 2 illustrates the amino acid residue sequence of the variable kappa light ($V_K$) domain of the Fabs binding to gp120. The Fab heterodimer designation is indicated in the left hand column. The light chain of Fab MT4 has been assigned SEQ ID NO 6 and is listed as such in the Sequence Listing. Fab MT4 is expressed from the original clone selected from a plasmid library generated from patient MT. The library was screened against gp120 as described in Example 1A. In addition, since the MT4 light chain was not randomized in the generation of the synthetic Fabs described in FIG. 1, the light chain amino acid sequence of MT4 is present in each of the Fabs 3b1, 3b3, 3b4 and 3b9, as described in Example 1.

FIG. 4 illustrates the coding nucleotide strand shown in the 5' to 3' direction of the heavy chain variable domain of original clone pMT4. The sequence is also listed in SEQ ID NO 7. The corresponding encoded heavy chain variable domain amino acid residue sequence is shown in FIG. 1. The pMT4 nucleotide sequence was randomized according to the present invention at the region of residues 82–96 corresponding to CDR1 and in separate mutagenesis procedures from residues 292–303, and then from 304–318 in CDR3. The positions of the residues are indicated in the figure numerically at every tenth residue marked with an asterisk.

FIG. 5 illustrates the amino acid residue sequences of variable heavy ($V_H$) domains of human Fabs binding to gp120. In Experiment A, CDR1 is randomized over amino acid residues 31–35. The CDR1 randomized library was screened against gp120 as described in Example 1A, and Example 1D. The amino acid residues 31–35 deduced from the nucleotide sequence of 12 selected Fabs in Experiment A is listed from right to left as complementary determining region 1 (CDR1). The 12 Fabs have been designated SEQ ID NOs 14–25 from the top of the column to the bottom, respectively, and are listed as such in the Sequence Listing. The sequence of the CDR1 of MT4 from which the other Fabs were derived is designated SEQ ID NO 8. The CDR1 randomized library was further randomized in the complementary determining region 3 (CDR3) region as described in Examples 1B and 1E. The deduced amino acid sequence of the CDR1 and CDR3 from eight Fabs selected from the randomized CDR1 and CDR3 library are given in Experiment B. The Fab heterodimer designations corresponding to the DNA clone from which the Fabs are expressed are indicated in the right hand column. The complete heavy chain variable domain sequences of Fabs, MT4, 3b1, 3b3, 3b4 and 3b9, have been respectively assigned SEQ ID NOs 1–5 and are listed as such in the Sequence Listing. The CDR1 of the Fabs 3b1, 3b2, 3b3, 3b4, 3b6, 3b7, 3b8, and 3b9 have been respectively assigned SEQ ID NOs 26–33 and are listed as such in the Sequence Listing. Fab MT4 is expressed from the original clone selected from a plasmid library generated from patient MT. The sequence of the CDR3 of MT4 from which the other Fabs were derived is designated SEQ ID NO 34. The sequenced regions of each Fab listed from left to right are amino acid residues 96–99 of CDR3. The CDR3 of the Fabs 3b1, 3b2, 3b3, 3b4, 3b6, 3b7, 3b8, and 3b9, have been respectively assigned SEQ ID NOs 35–42 and are listed as such in the Sequence Listing.

Figure 6:
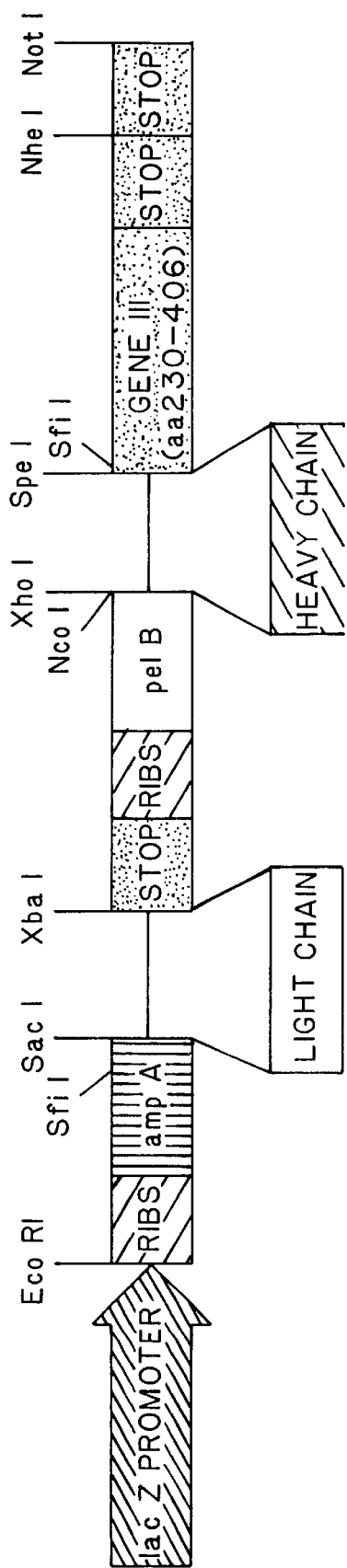

FIG. 6 illustrates a schematic representation of the heavy and light chain expression-control region of the phagemid Fab-display expression vector, pComb3H, as described in Example 2.

FIGS. 7A–7B illustrate the amino acid residue sequences of variable heavy ($V_H$) chain domains of gp120-specific human Fabs derived from mutagenizing the heavy chain CDR1 of phagemid MT4-3 (pMT4-3). The H4H1 series Fab heterodimer designations corresponding to the DNA clone from which the Fabs are expressed are indicated in the left hand column. The amino acid residue sequence of the heavy chain variable domain of the template Fab MT4 is presented under the indicated regions as described in the legend for FIG. 1. The portions of the amino acid residue sequence of the derived Fabs that are identical to the template Fab are indicated by ditto (") marks. The mutagenized CDR for each derived Fab is shown. The complete variable domain for each derived Fab having mutagenized heavy chain CDR1 is listed in the Sequence Listing corresponding to the assigned identifiers. The Fabs were obtained as described in Example 2.

Figure 8:
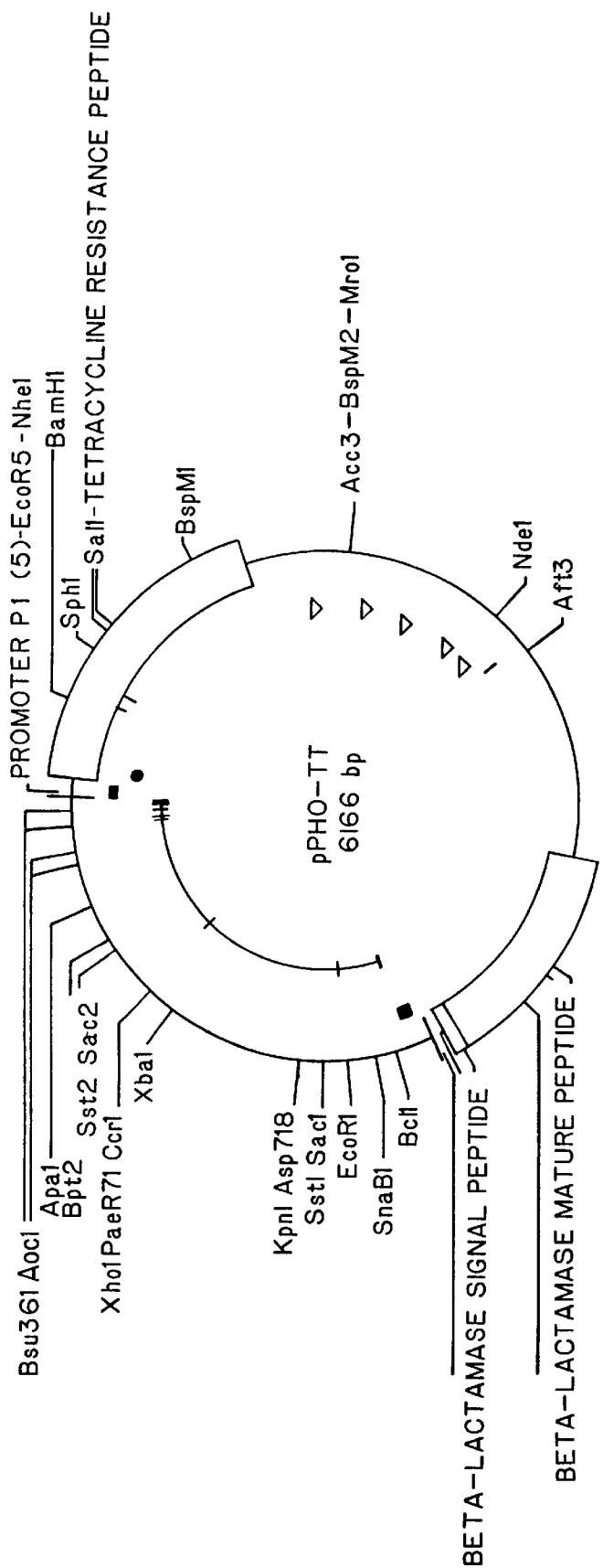

FIG. 8 illustrates the restriction map of the pPho-TT expression vector as described in Example 2. The complete nucleotide coding sequence of pPho-TT expression vector in 5' to 3' direction containing the nucleotide sequences encoding the heavy and light chain variable domains of a tetanus toxin (TT)-directed Fab is listed in the Sequence Listing as SEQ ID NO 51. The description of this vector and use thereof to express soluble Fabs of this invention replacing the anti-TT Fab is described in Example 2.

FIGS. 9A–9B illustrates the amino acid residue sequences of variable heavy ($V_H$) chain domains of gp120-specific human Fabs derived from mutagenizing the heavy chain CDR3 of phagemid 3b3 (p3b3). The M556 series Fab heterodimer designations corresponding to the DNA clone from which the Fabs are expressed are indicated in the left hand column. The amino acid residue sequence of the heavy chain variable domain of the template Fab 3b3 are presented under the indicated regions as described in the legend for FIG. 1. The portions of the amino acid residue sequence of the derived Fabs that are identical to the template Fab is indicated by ditto (") marks. The mutagenized CDR for each derived Fab is shown. The complete variable domain for each derived Fab having mutagenized heavy chain CDR3 is listed in the Sequence Listing corresponding to the assigned identifiers. The Fabs were obtained as described in Example 2.

FIG. 10 illustrates the coding nucleotide strand shown in the 5' to 3' direction of the light chain variable domain of original clone pMT4-3. The sequence is also listed in SEQ ID NO 62. The corresponding encoded light chain variable domain amino acid residue sequence is shown in FIG. 2 (SEQ ID NO 6).

FIGS. 11A–11B illustrate the amino acid residue sequences of variable kappa light ($V_K$) chain domains of gp120-specific human Fabs derived from mutagenizing the light chain CDR1 of phagemid 3b3 (p3b3) which is the same light chain as that encoded by pMT4-3 (SEQ ID NO 6) shown in FIG. 2. The A-D series Fab heterodimer designations corresponding to the DNA clone from which the Fabs are expressed are indicated in the left hand column. The amino acid residue sequence of the light chain variable domain of the template Fab 3b3 is presented under the indicated regions as described in the legend for FIG. 1. The portions of the amino acid residue sequence of the derived Fabs that are identical to the template Fab are indicated by ditto (") marks. The mutagenized CDR for each derived Fab is shown. The complete variable domain for each derived Fab having mutagenized light chain CDR1 is listed in the Sequence Listing with the assigned identifiers. The Fabs were obtained as described in Example 2.

FIGS. 12A–12B illustrate the amino acid residue sequences of variable kappa light ($V_K$) chain domains of gp120-specific human Fabs derived from mutagenizing the light chain CDR3 of phagemid 3b3 (p3b3) which is the same light chain as that of pMT4-3 (SEQ ID NO 6) shown in FIG. 2. The H4L3 series Fab heterodimer designations corresponding to the DNA clone from which the Fabs are expressed are indicated in the left hand column. The amino acid residue sequence of the light chain variable domain of the template Fab 3b3 is presented under the indicated regions as described in the legend for FIG. 1. The portions of the amino acid residue sequence of the derived Fabs that are identical to the template Fab are indicated by ditto (") marks. The mutagenized CDR for each derived Fab is shown. The complete variable domain for each derived Fab having mutagenized light chain CDR3 is listed in the Sequence Listing with the assigned identifiers. The Fabs were obtained as described in Example 2.

FIGS. 13A–13B illustrate the amino acid residue sequences of variable kappa light ($V_K$) chain domains of gp120-specific human Fabs derived from mutagenizing the light chain CDR3 of phagemid D encoding the previously CDR1-mutagenized and selected Fab D (SEQ ID NO 70) shown in FIGS. 11 and 13. The QA series Fab heterodimer designations corresponding to the DNA clone from which the Fabs are expressed are indicated in the left hand column. The amino acid residue sequence of the light chain variable domain of the template Fab D is presented under the indicated regions as described in the legend for FIG. 1. The portions of the amino acid residue sequence of the derived Fabs that are identical to the template Fab are indicated by ditto (") marks. The mutagenized CDR for each derived Fab is shown. The complete variable domain for each derived Fab having mutagenized light chain CDR3 is listed in the Sequence Listing with the assigned identifiers. The Fabs were obtained as described in Example 3.

FIGS. 14A–14B illustrate the amino acid residue sequence of the variable kappa light ($V_K$) chain domain of the gp120-specific human composite light chain designated L42. The L42 phagemid for encoding the L42 light chain was derived from ligating the Sac I/Kpn I fragment of phagemid D (encodes Fab D shown in FIGS. 11 and 13) with the Kpn I/Xba I fragment of phagemid H4L3-2 (encodes Fab H4L3-2 shown in FIG. 12). The amino acid residue sequence of the L42 composite light chain variable domain is presented under the indicated regions as described in the legend for FIG. 1 and in the Sequence Listing in SEQ ID NO 88. The L42 light chain was obtained as described in Example 3.

FIGS. 15A–15B illustrate the amino acid residue sequences of the variable heavy ($V_H$) chain domains of the gp120-specific human composite heavy chains designated H31, H33, H101 and H103. The composites were prepared as described in Example 3. The amino acid residue sequence of each composite heavy chain variable domain is presented under the indicated regions as described in the legend for FIG. 1 and in the identified SEQ ID NOs. The portions of the amino acid residue sequence of the composite heavy chain variable domain regions that are identical to that shown for H31 are indicated by ditto (") marks. The mutagenized CDR1 and CDR3 are separately indicated for each heavy chain composite.

DETAILED DESCRIPTION OF THE INVENTION

A. Definitions

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in J. Biol. Chem., 243:3552–59 (1969) and adopted at 37 CFR §1.822(b)(2)), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) Molecule: A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptase.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Synthetic Monoclonal Antibody: The term "synthetic" indicates, when used in the phrase "synthetic monoclonal antibody", that the antibody is not naturally isolated, but rather is the product of mutagenesis, as described herein, in the heavy or light chain variable regions of cloned human immunoglobulin genes to produce artificial antibodies having characteristic amino acid residue sequences which impart the immunospecificity, immunoaffinity and HIV-neutralization activity as described herein.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Leader Polypeptide: A short length of amino acid sequence at the amino end of a polypeptide, which carries or directs the polypeptide through the inner membrane and so ensures its eventual secretion into the periplasmic space and perhaps beyond. The leader sequence peptide is commonly removed before the polypeptide becomes active.

Reading Frame: Particular sequence of contiguous nucleotide triplets (codons) employed in translation. The reading frame depends on the location of the translation initiation codon.

B. Synthetic Human Monoclonal Antibodies

The present invention relates to synthetic human monoclonal antibodies which are specific for, and neutralize human immunodeficiency virus (HIV). In a preferred embodiment of the invention, human monoclonal antibodies are disclosed which are capable of binding epitopic polypeptide sequences in an HIV protein, and preferably in HIV glycoprotein gp120 or gp160.

The synthetic monoclonal antibodies are unusual insofar as they are of human derivation, but are modified by recombinant methodologies to yield a synthetic product which exhibits high immunoreaction affinity for target antigen. Furthermore, the synthetic monoclonal antibodies have a potent capacity to neutralize HIV. The capacity to neutralize HIV is expressed as a concentration of antibody molecules required to reduce the infectivity titer of a suspension of HIV when assayed in an typical in vitro infectivity assay, such as is described herein. A synthetic monoclonal antibody of this invention has the capacity to reduce HIV infectivity titer in an in vitro virus infectivity assay by 50% at a concentration of less than 100 nanograms (ng) of antibody per milliliter (ml) of culture medium in the assay, and preferably reduces infectivity titers 50% at a concentration of less than 20 ng/ml, and more preferably at concentrations less than 10 ng/ml.

Exemplary and preferred synthetic monoclonal antibodies described herein are effective at 5–20 ng/ml, and therefore are particularly well suited for inhibiting HIV in vitro and in vivo.

Also disclosed is an antibody having a specified amino acid sequence, which sequence confers the ability to bind a specific epitope and to neutralize HIV when the virus is bound by these antibodies. A human monoclonal antibody with a claimed specificity, and like human monoclonal antibodies with like specificity, are useful in the diagnosis and immunotherapy of HIV-induced disease.

The term "HIV-induced disease" means any disease caused, directly or indirectly, by HIV. An example of a HIV-induced disease is acquired autoimmunodeficiency syndrome (AIDS), and any of the numerous conditions associated generally with AIDS which are caused by HIV infection.

Thus, in one aspect, the present invention is directed to synthetic human monoclonal antibodies which are reactive with a HIV neutralization site and cell lines which produce such antibodies. The isolation of cell lines producing monoclonal antibodies of the invention is described in great detail further herein, and can be accomplished using the phagemid vector library methods described herein, and using routine screening techniques which permit determination of the elementary immunoreaction and neutralization patterns of the monoclonal antibody of interest. Thus, if a human monoclonal antibody being tested binds and neutralizes HIV, then the human monoclonal antibody being tested and the human monoclonal antibody produced by the cell lines of the invention are considered equivalent.

It is also possible to determine, without undue experimentation, if a human monoclonal antibody has the same (i.e., equivalent) specificity as a human monoclonal antibody of this invention by ascertaining whether the former prevents the latter from binding to HIV. If the human monoclonal antibody being tested competes with the human monoclonal antibody of the invention, as shown by a decrease in binding by the human monoclonal antibody of the invention in standard competition assays for binding to solid phase gp120 antigen, then it is likely that the two monoclonal antibodies bind to the same, or a closely related, epitope.

Still another way to determine whether a human monoclonal antibody has the specificity of a human monoclonal antibody of the invention is to pre-incubate the human monoclonal antibody of the invention with HIV with which it is normally reactive, and then add the human monoclonal antibody being tested to determine if the human monoclonal antibody being tested is inhibited in its ability to bind HIV. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out utilizing HIV neutralization assays and determining whether the monoclonal antibody neutralizes HIV.

The ability to neutralize HIV at one or more stages of virus infection is a desirable quality of a human monoclonal antibody of the present invention. Virus neutralization can be measured by a variety of in vitro and in vivo methodologies. Exemplary methods described herein for determining the capacity for neutralization are the in vitro assays that measure inhibition of HIV-induced syncytia formation, and assays that measure the inhibition of output of core p24 antigen from a cell infected with HIV.

As shown herein, the immunospecificity of a human monoclonal antibody of this invention can be directed to epitopes that are shared across serotypes and/or strains of HIV, or can be specific for a single strain of HIV, depending upon the epitope. Thus, a preferred human monoclonal antibody can immunoreact with HIV-1, HIV-2, or both, and can immunoreact with one or more of the HIV-1 strains IIIB, MN, RF, SF-2, Z2, Z6, CDC4, ELI and the like strains.

In a particularly preferred embodiment, the invention describes numerous human monoclonal antibodies produced by the present methods with each antibody exhibiting the ability to neutralize multiple strains of HIV, particularly field isolates. By sequential randomization of the CDR regions of heavy and/or light chain genes as described herein, multiple antibody species were produced that could neutralize several different field strains of HIV.

Thus, the invention also contemplates a human monoclonal antibody capable of immunoreacting with and neutralizing a first preselected human immunodeficiency virus (HIV), such as the laboratory isolate MN or IIB, that is further capable of immunoreacting with and neutralizing one or more other (i.e., second) strains of HIV, particularly field strains. In this embodiment, supported by the teachings of the Examples, the antibody has the capacity to reduce HIV infectivity titer in an in vitro virus infectivity assay of the first HIV strain by 50% at a concentration of less than 100 nanograms (ng) of antibody per milliliter (ml), and has the capacity to reduce HIV infectivity titer of a second field strain of HIV in the same in vitro virus infectivity assay by 50% at a concentration of less than about 10 micrograms (ug) of antibody per milliliter (ml). In more preferred embodiments and depending upon the particular HIV strain, the capacity to reduce infectivity titers by 50% can be exhibited at lower antibody concentrations, such as below 1 ug/ml, and preferably below 100 ng/ml.

The immunospecificity of an antibody, its HIV-neutralizing capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence. Preferred human monoclonal antibodies immunoreact with glycoprotein gp120.

A preferred human monoclonal antibody of this invention has the binding specificity of a monoclonal antibody comprising a heavy chain immunoglobulin variable region amino acid residue sequence selected from the group of sequences consisting of SEQ ID NOs 2, 3, 4 and 5, and conservative substitutions thereof.

Another preferred human monoclonal antibody of this invention has the binding specificity of a monoclonal antibody having a light chain immunoglobulin variable region amino acid residue sequence of SEQ ID NO 6, and conservative substitutions thereof.

Using known combinatorial library shuffling and screening methods, one can identify new heavy and light chain pairs (H:L) that function as a HIV-neutralizing monoclonal antibody. In particular, one can shuffle a known heavy chain, derived from an HIV-neutralizing human monoclonal antibody, with a library of light chains to identify new H:L pairs that form a functional antibody according to the present invention. Similarly, one can shuffle a known light chain, derived from an HIV-neutralizing human monoclonal antibody, with a library of heavy chains to identify new H:L pairs that form a functional antibody according to the present invention.

Particularly preferred human monoclonal antibodies are those having the immunoreaction (binding) specificity of a monoclonal antibody having heavy and light chain immunoglobulin variable region amino acid residue sequences in pairs (H:L) selected from the group consisting of SEQ ID NOs 2:6, 3:6, 4:6 and 5:6, and conservative substitutions thereof. The designation of two SEQ ID NOs with a colon, e.g., 2:6, is to connote a H:L pair formed by the heavy and light chain, respectively, amino acid residue sequences shown in SEQ ID NO 2 and SEQ ID NO 6, respectively.

Particularly preferred is a human monoclonal antibody having the binding specificity of the monoclonal antibody having a heavy chain sequence shown in SEQ ID NOs 2, 3, 4 or 5, and further that contains the sequences present in the antibody molecule MT4 encoded by the pMT4 expression vectors deposited with the ATCC on Oct. 19, 1993, as described further herein. By "having the binding specificity" is meant equivalent monoclonal antibodies which exhibit the same or similar immunoreaction and neutralization properties, and which compete for binding to an HIV antigen.

In a preferred embodiment, the immunoaffinity of the subject antibody is particularly high, thereby providing high potency in therapeutic applications and providing high specificity with low background in diagnostic applications. In this embodiment, a subject synthetic human monoclonal antibody, in addition to the above-recited neutralization capacity, immunoreacts with HIV with a dissociation constant ($K_d$) of about $1\times10^{-8}$ molar (M) or less. That is, antibodies which have affinities greater than $10^{-8}$ M are particularly preferred. By the present synthetic methods, numerous monoclonal antibodies have been generated with affinities, expressed as $K_d$, in the range of $10^{-9}$ to $10^{-12}$ M.

Insofar as either the light or heavy chain variable region, or both, can be modified in sequence by the present methods, a preferred antibody of this invention may contain a preferred heavy chain, light chain, or both. Thus a preferred synthetic human monoclonal antibody has the binding specificity of a monoclonal antibody comprising a heavy chain immunoglobulin variable region amino acid residue sequence selected from the group consisting of SEQ ID NOs 1, 3, 54, 55, 56, 57, 58, 59, 89, 90, 91 and 92, and conservative substitutions thereof. In addition, a preferred synthetic human monoclonal antibody has the binding specificity of a monoclonal antibody comprising a light chain immunoglobulin variable region amino acid residue sequence selected from the group consisting of SEQ ID NOs 6, 69, 70, 73, 75, 76, 77, 79, 80, 82, 83, 84, 85, 86, 87 and 88, and conservative substitutions thereof.

A particularly preferred synthetic human monoclonal antibody has a dissociation constant from about $1\times10^{-9}$ M to about $1\times10^{-10}$ M. In this embodiment, a specific preferred antibody has the binding specificity of a monoclonal antibody having heavy and light chain immunoglobulin variable region amino acid residue sequences in pairs selected from the group consisting of SEQ ID NOs 3:6, 3:69, 3:70, 3:73, 3:75, 3:76, 3:77, 3:79, 3:80, 3:82, 3:83, 3:84, 3:87, 54:6, 55:6, 56:6, 57:6, 58:6, 59:6, 90:88, 91:6, 91:88 and 92:88, and conservative substitutions thereof.

A still more preferred synthetic human monoclonal antibody has a dissociation constant from about $1\times10^{-10}$ M to about $1\times10^{-11}$ M. In this embodiment, a specific preferred antibody has the binding specificity of a monoclonal antibody having heavy and light chain immunoglobulin variable region amino acid residue sequences in pairs selected from the group consisting of SEQ ID NOs 3:85, 3:86, 89:6 and 90:86, and conservative substitutions thereof.

A more preferred synthetic human monoclonal antibody has a dissociation constant from about $1\times10^{-11}$ M to about $1\times10^{-12}$ M. In this embodiment, a specific preferred antibody has the binding specificity of a monoclonal antibody having heavy and light chain immunoglobulin variable region amino acid residue sequences in pairs shown in SEQ ID NOs 89:88, and conservative substitutions thereof. Particularly preferred is an antibody having the binding specificity of the monoclonal antibody produced by plasmid pPHO-H31/L42-1 contained in ATCC accession number 69691.

Exemplary antibodies having the above immunoaffinities are described in the examples.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also neutralize HIV. Analogously, another preferred embodiment of the invention relates to polynucleotides which encode the above noted heavy and/or light chain polypeptides and to polynucleotide sequences which are complementary to these polynucleotide sequences. Complementary polynucleotide sequences include those sequences which hybridize to the polynucleotide sequences of the invention under stringent hybridization conditions.

By using the human monoclonal antibodies of the invention, it is now possible to produce anti-idiotypic antibodies which can be used to screen human monoclonal antibodies to identify whether the antibody has the same binding specificity as a human monoclonal antibody of the invention and also used for active immunization (Herlyn et al., *Science,* 232:100 (1986)). Such anti-idiotypic antibodies can be produced using well-known hybridoma techniques (Kohler et al., *Nature,* 256:495 (1975)). An anti-idiotypic antibody is an antibody which recognizes unique determinants present on the human monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the human monoclonal antibody of the invention produced by a cell line which was used to immunize the second animal, it is now possible to identify other clones with the same idiotype as the antibody of the hybridoma used for immunization. Idiotypic identity between human monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

In one preferred embodiment, the invention contemplates a truncated immunoglobulin molecule comprising a Fab fragment derived from a human monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods. A preferred method of producing a soluble Fab fragment is described herein.

Human monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies.

The invention also contemplates, in one embodiment, a monoclonal antibody of this invention produced by the present methods.

C. Immunotherapeutic Methods and Compositions

The synthetic human monoclonal antibodies of this invention can also be used immunotherapeutically for HIV disease due to their demonstrated neutralization activity and high immunoaffinity for target antigen. The term "immunotherapeutically" or "immunotherapy" as used herein in conjunction with the monoclonal antibodies of the invention denotes both prophylactic as well as therapeutic administration. Thus, the monoclonal antibodies can be administered to high-risk patients in order to lessen the likelihood and/or severity of HIV-induced disease, administered to patients already evidencing active HIV infection, or administered to patients at risk of HIV infection.

1. Therapeutic Compositions

The present invention therefore contemplates therapeutic compositions useful for practicing the therapeutic methods described herein. Therapeutic compositions of the present invention contain a physiologically tolerable carrier together with at least one species of human monoclonal antibody as described herein, dissolved or dispersed therein as an active ingredient. In a preferred embodiment, the therapeutic composition is not immunogenic when administered to a human patient for therapeutic purposes, unless that purpose is to induce an immune response, as described elsewhere herein.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycon, polyethylene glycol and other solutes.

Liquid compositions can also contain liquid phases in addition to water and to the exclusion of water. Exemplary of such additional liquid phases are glycerin, vegetable oils such as cottonseed oil, organic esters such as ethyl oleate, and water-oil emulsions.

A therapeutic composition contains an HIV-neutralizing of a human monoclonal antibody of the present invention, typically an amount of at least 0.1 weight percent of antibody per weight of total therapeutic composition. A weight percent is a ratio by weight of antibody to total composition. Thus, for example, 0.1 weight percent is 0.1 grams of antibody per 100 grams of total composition.

2. Therapeutic Methods

In view of the demonstrated HIV neutralizing ability of the human monoclonal antibodies of the present invention, the present disclosure provides for a method for neutralizing HIV in vitro or in vivo. The method comprises contacting a sample believed to contain HIV with a composition comprising a therapeutically effective amount of a human monoclonal antibody of this invention. A preferred therapeutically effective amount is an amount sufficient to effect a 50% reduction in infectivity, preferably a 90% reduction, and more preferably a 99% reduction when assayed in an in vitro assay as described herein.

For in vivo modalities, the method comprises administering to the patient a therapeutically effective amount of a physiologically tolerable composition containing a human monoclonal antibody of the invention. Thus, the present invention describes in one embodiment a method for providing passive immunotherapy to HIV disease in a human comprising administering to the human an immunotherapeutically effective amount of the monoclonal antibody of this invention.

A representative patient for practicing the present passive immunotherapeutic methods is any human exhibiting symptoms of HIV-induced disease, including AIDS or related conditions believed to be caused by HIV infection, and humans at risk of HIV infection, i.e., prophylactic treatments to prevent infection. Patients at risk of infection by HIV include babies of HIV-infected pregnant mothers, recipients of transfusions known to contain HIV, users of HIV contaminated needles, individuals who have participated in high risk sexual activities with known HIV-infected individuals, and the like risk situations.

In one embodiment, the passive immunization method comprises administering a composition comprising more than one species of human monoclonal antibody of this invention, preferably directed to non-competing epitopes or directed to distinct serotypes or strains of HIV, as to afford increased effectiveness of the passive immunotherapy.

A therapeutically (immunotherapeutically) effective amount of a human monoclonal antibody is a predetermined amount calculated to achieve the desired effect, i.e., to neutralize the HIV present in the sample or in the patient, and thereby decrease the amount of detectable HIV in the sample or patient. In the case of in vivo therapies, an effective amount can be measured by improvements in one or more symptoms associated with HIV-induced disease occurring in the patient, or by serological decreases in HIV antigens.

Thus, the dosage ranges for the administration of the monoclonal antibodies of the invention are those large enough to produce the desired effect in which the symptoms of the HIV disease are ameliorated or the likelihood of infection decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an antibody of this invention is typically an amount of antibody such that when administered in a physiologically tolerable composition is sufficient to achieve a plasma concentration from about 0.1 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The human monoclonal antibodies of the invention can be administered parenterally by injection or by gradual infusion over time. Although the HIV infection is typically systemic and therefore most often treated by intravenous administration of therapeutic compositions, other tissues and delivery means are contemplated where there is a likelihood that the tissue targeted contains infectious HIV. Thus, human monoclonal antibodies of the invention can be administered intravenously, intraperitoneally, intramuscularly, subcutaneously, intracavity, transdermally, and can be delivered by peristaltic means.

The therapeutic compositions containing a human monoclonal antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of a monoclonal antibody, a diagnostic method for detecting a monoclonal antibody in the subject's blood is useful to characterize the fate of the administered therapeutic composition.

The invention also relates to a method for preparing a medicament or pharmaceutical composition comprising the human monoclonal antibodies of the invention, the medicament being used for immunotherapy of HIV disease.

D. Diagnostic Assay Methods

The present invention also contemplates various assay methods for determining the presence, and preferably amount, of HIV in a sample such as a biological fluid or tissue sample using a human monoclonal antibody of this invention as an immunochemical reagent to form an immunoreaction product whose amount relates, either directly or indirectly, to the amount of HIV in the sample.

Those skilled in the art will understand that there are numerous well known clinical diagnostic chemistry procedures in which an immunochemical reagent of this invention can be used to form an immunoreaction product, in vitro or in vivo, whose amount relates to the amount of HIV present in a body sample. Thus, while exemplary assay methods are described herein, the invention is not so limited.

Various heterogenous and homogeneous protocols, either competitive or noncompetitive, can be employed in performing an assay method of this invention. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of HIV. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, HIV may be detected by the monoclonal antibodies of the invention when present in samples of biological fluids and tissues. Any sample containing a detectable amount of HIV can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The monoclonal antibodies of the invention are suited for use in vitro, for example, in immunoassays in which they can be utilized in liquid phase or bound to a solid phase carrier for the detection of HIV in samples, as described above. The monoclonal antibodies in these immunoassays can be detectably labeled in various ways for in vitro use.

In using the human monoclonal antibodies of the invention for the in vivo detection of antigen, the detectably labeled human monoclonal antibody is given in a dose which is diagnostically effective. The term "diagnostically effective" means that the amount of detectably labeled human monoclonal antibody is administered in sufficient quantity to enable detection of the site having the HIV antigen for which the monoclonal antibodies are specific.

The concentration of detectably labeled human monoclonal antibody which is administered should be sufficient such that the binding to HIV is detectable compared to the background. Further, it is desirable that the detectably labeled monoclonal antibody be rapidly cleared from the circulatory system in order to give the best target-to-background signal ratio.

As a rule, the dosage of detectably labeled human monoclonal antibody for in vivo diagnosis will vary depending on such factors as age, sex, and extent of disease of the individual. The dosage of human monoclonal antibody can vary from about 0.01 mg/$M^2$ to about 500 mg/$m^2$, preferably 0.1 mg/$m^2$ to about 200 mg/$m^2$, most preferably about 0.1 mg/$m^2$ to about 10 mg/$m^2$. Such dosages may vary, for example, depending on whether multiple injections are given, tissue, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI.

Elements which are particularly useful in such techniques include $^{157}$Gd, $^{55}$Mn, $^{162}$Dy, $^{52}$Cr, and $^{56}$Fe.

The human monoclonal antibodies of the invention can be used in vitro and in vivo to monitor the course of HIV disease therapy. Thus, for example, by measuring the increase or decrease in the number of cells infected with HIV or changes in the concentration of HIV present in the body or in various body fluids, it would be possible to determine whether a particular therapeutic regimen aimed at ameliorating the HIV disease is effective.

E. Diagnostic Systems

The present invention also describes a diagnostic system, preferably in kit form, for assaying for the presence of HIV in a sample according to the diagnostic methods described herein. A diagnostic system includes, in an amount sufficient to perform at least one assay, a subject human monoclonal antibody, as a separately packaged reagent.

In another embodiment, a diagnostic system is contemplated for assaying for the presence of an anti-HIV monoclonal antibody in a body fluid sample such as for monitoring the fate of therapeutically administered antibody. The system includes, in an amount sufficient for at least one assay, a subject antibody as a control reagent, and preferably a preselected amount of HIV antigen, each as separately packaged immunochemical reagents.

Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In embodiments for detecting HIV in a body fluid, a diagnostic system of the present invention can include a label or indicating means capable of signaling the formation of an immunocomplex containing a human monoclonal antibody of the present invention.

The word "complex" as used herein refers to the product of a specific binding reaction such as an antibody-antigen reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethyl-rhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabelling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is 125I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of an APC inhibitor of this invention in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in some embodiments, a human monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a human monoclonal antibody of the invention which is, or can be, detectably labelled. The kit may also have containers containing any of the other above-recited immunochemical reagents used to practice the diagnostic methods.

F. Methods for Producing a Synthetic HIV-Neutralizing Human Monoclonal Antibody

The present invention describes methods for producing novel synthetic HIV-neutralizing human monoclonal antibodies. The methods are based generally on the use of combinatorial libraries of antibody molecules which can be produced from a variety of sources, and include naive libraries, modified libraries, and libraries produced directly from human donors exhibiting an HIV-specific immune response.

The combinatorial library production and manipulation methods have been extensively described in the literature, and will not be reviewed in detail herein, except for those feature required to make and use unique embodiments of the present invention. However, the methods generally involve the use of a filamentous phage (phagemid) surface expression vector system for cloning and expressing antibody species of the library. Various phagemid cloning systems to produce combinatorial libraries have been described by others. See, for example the preparation of combinatorial antibody libraries on phagemids as described by Kang et al., *Proc. Natl. Acad. Sci., USA*, 88:4363–4366 (1991); Barbas et al., *Proc. Natl. Acad. Sci., USA*, 88:7978–7982 (1991); Zebedee et al., *Proc. Natl. Acad. Sci. USA*, 89:3175–3179 (1992); Kang et al., *Proc. Natl. Acad. Sci., USA*, 88:11120–11123 (1991); Barbas et al., *Proc. Natl. Acad. Sci., USA*, 89:4457–4461 (1992); and Gram et al., *Proc. Natl. Acad. Sci., USA*, 89:3576–3580 (1992), the disclosures of which are hereby incorporated by reference.

In one embodiment, the method involves first preparing a phagemid library of human monoclonal antibodies by using donor immune cell messenger RNA from HIV-infected donors. The donors can be symptomatic of AIDS, but in preferred embodiments the donor is asymptomatic, as the resulting library contains a substantially higher number of HIV-neutralizing human monoclonal antibodies.

In another embodiment, the donor is naive relative to an immune response to HIV, i.e., the donor is not HIV-infected. Alternatively, the starting library can be synthetic, or can be derived from a donor who has an immune response to other antigens.

The method for producing a phagemid library of human monoclonal antibodies generally involves (1) preparing separate H and L chain-encoding gene libraries in cloning vectors using human immunoglobulin genes as a source for the libraries, (2) combining the H and L chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected antigen, thereby isolating one or more species of phagemid containing particular H and L chain-encoding genes forming antibody molecules that immunoreact with the preselected antigen.

As described herein the Examples, the resulting phagemid library is then manipulated to increase and/or alter the immunospecificities of the monoclonal antibodies of the library to produce and subsequently identify additional, desirable, human monoclonal antibodies of the present invention which are referred to as "synthetic" antibodies because they are not obtained directly from humans, but are derived from human antibodies following synthetic manipulations. Alternatively, a particular preselected monoclonal antibody can be manipulated to yield a synthetic antibody having superior properties as described further herein.

For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in one (or more) complementarity determining region (CDR) of the variable region of the immunoglobulin polypeptide, and subsequently screened for desirable immunoreaction and neutralization capabilities.

In one embodiment, the H and L genes can be cloned into separate, monocistronic expression vectors, referred to as a "binary" system described further herein. In this method, step (2) above differs in that the combining of H and L chain encoding genes occurs by the co-introduction of the two binary plasmids into a single host cell for expression and assembly of a phagemid having the surface accessible antibody heterodimer molecule.

In the present methods, the antibody molecules are monoclonal because the cloning methods allow for the preparation of clonally pure species of antibody producing cell lines. In addition, the monoclonal antibodies are human because the H and L chain encoding genes are derived from human immunoglobulin producing immune cells, such as those obtained from spleen, thymus, bone marrow, and the like.

The method of producing a HIV-neutralizing human monoclonal antibody also requires that the resulting antibody library, immunoreactive with a preselected HIV antigen, is screened for the presence of antibody species which have the capacity to neutralize HIV in one or more of the assays described herein for determining neutralization capacity. Thus, a preferred library of antibody molecules is first produced which binds to an HIV antigen, preferably gp160, gp120, the V3 loop region of gp160, or the CD4 binding site of gp120, and then is screened for the presence of HIV-neutralizing antibodies as described herein.

Additional libraries can be screened from shuffled libraries for additional HIV-immunoreactive and neutralizing human monoclonal antibodies.

As a further characterization of the present invention the nucleotide and corresponding amino acid residue sequence of the antibody molecule's H or L chain encoding gene is determined by nucleic acid sequencing. The primary amino acid residue sequence information provides essential information regarding the antibody molecule's epitope reactivity.

Synthetic human monoclonal antibodies of this invention are produced by altering the nucleotide sequence of a polynucleotide sequence that encodes a heavy or light chain of a monoclonal antibody. For example, by site-directed mutagenesis, one can alter the nucleotide sequence of an expression vector and thereby introduce changes in the resulting expressed amino acid residue sequence. Thus one can take the amino acid residue sequence of SEQ ID NO 2, for example, and convert it into the amino acid residue sequence of SEQ ID NO 3 via mutagenesis of the corresponding nucleic acids. Similarly, one can take a known polynucleotide and randomly alter it by random mutagenesis, reintroduce the altered polynucleotide into an expression system and subsequently screen the product H:L pair for HIV-neutralizing activity.

Site-directed and random mutagenesis methods are well known in the polynucleotide arts, and are not to be construed as limiting as methods for altering the nucleotide sequence of a subject polynucleotide.

Due to the presence of the phage particle in an immunoaffinity isolated antibody, one embodiment involves the manipulation of the resulting cloned genes to truncate the immunoglobulin-coding gene such that a soluble Fab fragment is secreted by the host *E. coli* cell containing the phagemid vector. Thus, the resulting manipulated cloned immunoglobulin genes produce a soluble Fab which can be readily characterized in ELISA assays for epitope binding studies, in competition assays with known anti-HIV antibody molecules, and in HIV neutralization assays. The solubilized Fab provides a reproducible and comparable antibody preparation for comparative and characterization studies.

The preparation of soluble Fab is generally described in the immunological arts, and can be conducted as described herein in the examples, or as described by Burton et al., *Proc. Natl. Acad. Sci., USA*, 88:10134–10137 (1991).

In addition, one can readily produce a whole antibody molecule that includes a functional Fc domain by further engineering of the Fab to add back the polypeptide sequences that define Fc, as is well known.

1. Phase Display Expression Vectors and Polynucleotides for Expressing Anti-HIV Monoclonal Antibodies The preparation of human monoclonal antibodies of this invention depends, in one embodiment, on the cloning and expression vectors used to prepare the combinatorial antibody libraries described herein. The cloned immunoglobulin heavy and light chain genes can be shuttled between lambda vectors, phagemid vectors and plasmid vectors at various stages of the methods described herein.

The phagemid vectors produce fusion proteins that are expressed on the surface of an assembled filamentous phage particle. The use of phage display vectors allow a particular advantage by providing a means to screen a very large population of expressed display proteins and thereby locate one or more specific clones that code for a desired binding reactivity. The use of phage display also facilitates the rapid and reproducible isolation of multiple species of the invention. For example, four antibodies were produced in one example of the present invention.

The use of phage display vectors derives from the previously described use of combinatorial libraries of antibody molecules based on phagemids. The combinatorial library production and manipulation methods have been extensively described in the literature, and will not be reviewed in detail herein, except for those features required to make and use unique embodiments of the present invention. However, the methods generally involve the use of a filamentous phage (phagemid) surface expression vector system for cloning and expressing antibody species of the library. Various phagemid cloning systems to produce combinatorial libraries have been described by others. See, for example the preparation of combinatorial antibody libraries on phagemids as described by Kang et al., *Proc. Natl. Acad. Sci., USA*, 88:4363–4366 (1991); Barbas et al., *Proc. Natl. Acad. Sci., USA*, 88:7978–7982 (1991); Zebedee et al., *Proc. Natl. Acad. Sci., USA*, 89:3175–3179 (1992); Kang et al., *Proc. Natl. Acad. Sci., USA*, 88:11120–11123 (1991); Barbas et al., *Proc. Natl. Acad. Sci., USA*, 89:4457–4461 (1992); and Gram et al., *Proc. Natl. Acad. Sci., USA*, 89:3576–3580 (1992), the disclosures of which are hereby incorporated by reference.

A phagemid vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide defining an immunoglobulin heavy or light chain variable region, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface.

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52 (Ohkawa et al., *J. Biol. Chem.,* 256:9951–9958, 1981). An exemplary membrane anchor would consist of residues 26 to 40 of cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage at one end of the phage particle with typically about 4 to 6 copies of the coat protein.

For detailed descriptions of the structure of filamentous phage particles, their coat proteins and particle assembly, see the reviews by Rached et al., *Microbiol. Rev.,* 50:401–427 (1986); and Model et al., in "The Bacteriophages: Vol. 2", R. Calendar, ed. Plenum Publishing Co., pp. 375–456 (1988).

The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei et al., *Nature,* 331:543–546 (1988).

The leader sequence of the pelB protein has previously been used as a secretion signal for fusion proteins (Better et al., *Science,* 240:1041–1043 (1988); Sastry et al., *Proc. Natl. Acad. Sci., USA,* 86:5728–5732 (1989); and Mullinax et al., *Proc. Natl. Acad. Sci., USA,* 87:8095–8099 (1990)).

Another preferred secretion signal is an ompA secretion signal. The predicted amino acid residue sequences of the secretion signal domain from the ompA gene product from *E. coli* is described in Movva, et al., *J. Mol. Biol.,* 147:317–328 (1980).

The leader sequence of the ompA protein has previously been used as a secretion signal for fusion proteins by Skerra et al., *Science,* 240:1038–1041 (1988).

Amino acid residue sequences for other secretion signal polypeptide domains from *E. coli* useful in this invention as described in Oliver, *Escherichia coli* and *Salmonella Typhimurium,* Neidhard, F. C. (ed.), American Society for Microbiology, Washington, D.C., 1:56–69 (1987).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

The 3' control sequences define at least one termination (stop) codon in frame with and operatively linked to the heterologous fusion polypeptide.

In preferred embodiments, the vector utilized includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli,* a preferred origin of replication is ColE1 found in pBR322 and a variety of other common plasmids. Also preferred is the p15A origin of replication found on PACYC and its derivatives. The ColE1 and p15A replicon have been extensively utilized in molecular biology, are available on a variety of plasmids and are described at least by Sambrook et al., in "Molecular Cloning: a Laboratory Manual", 2nd edition, Cold Spring Harbor Laboratory Press (1989).

The ColE1 and p15A replicons are particularly preferred for use in one embodiment of the present invention where two "binary" plasmids are utilized because they each have the ability to direct the replication of plasmid in *E. coli* while the other replicon is present in a second plasmid in the same *E. coli* cell. In other words, ColE1 and p15A are non-interfering replicons that allow the maintenance of two plasmids in the same host (see, for example, Sambrook et al., in "Molecular Cloning: a Laboratory Manual", 2nd edition, Cold Spring Harbor Laboratory Press (1989), at pages 1.3–1.4). This feature is particularly important when using binary vectors because a single host cell permissive for phage replication must support the independent and simultaneous replication of two separate vectors, for example when a first vector expresses a heavy chain polypeptide and a second vector expresses a light chain polypeptide.

In addition, those embodiments that include a prokaryotic replicon can also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which a transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see, for example, Rasched et al., *Microbiol. Rev.,* 50:401–427, 1986; and Horiuchi, *J. Mol. Biol.,* 188:215–223, 1986). A preferred filamentous phage origin of replication for use in the present invention is an M13, f1 or fd phage origin of replication (Short et al., *Nucl. Acids Res.,* 16:7583–7600, 1988).

Preferred DNA expression vectors for cloning and expressing a phagemid display protein of this invention are the dicistronic plasmid expression vectors pComb3, pComb3H-TT, pPHO-TT and pMT4-3 described herein. The complete nucleotide sequence of pComb3H-TT and pPHO-TT are shown in the Sequence Listing at SEQ ID NOs 43 and 51, respectively.

It is to be understood that, due to the genetic code and its attendant redundancies, numerous polynucleotide sequences can be designed that encode a contemplated heavy or light chain immunoglobulin variable region amino acid residue sequence. Thus, the invention contemplates such alternate polynucleotide sequences incorporating the features of the redundancy of the genetic code.

The phagemid and expression vectors of the present invention can be prepared in a variety of ways. The vectors can be assembled from component parts using the disclosed complete nucleotide sequences of preferred vectors, or can be derived by selective modifications of existing vectors. Other methods are apparent to one skilled in the art, and therefore, the methods for preparing and manipulating the vectors are not to be considered as limiting to the invention.

Insofar as the expression vector for producing a human monoclonal antibody of this invention is carried in a host cell compatible with expression of the antibody, the invention contemplates a host cell containing a vector or polynucleotide of this invention. A preferred host cell is *E. coli,* as described herein.

A preferred expression vector plasmid pMT4-3 used to produce a phagemid display protein of this invention was deposited in the form of pMT4 on Oct. 19, 1993, pursuant to Budapest Treaty requirements with the American Type Culture Collection (ATCC), Rockville, Md., as described herein.

The term "pMT4-3" refers to a particular phagemid expression vector in which the gene 3 membrane anchor is present, whereas the term "pMT4" refers to the same vector except that the gene 3 membrane anchor has been removed such that the expressed Fab is soluble as described in the Examples.

Insofar as polynucleotides are component parts of a DNA expression vector for producing a human monoclonal antibody heavy or light chain immunoglobulin variable region amino acid residue sequence, the invention also contemplates isolated polynucleotides that encode such heavy or light chain sequences.

2. Oligonucleotides

The modification of a cloned immunoglobulin to form a synthetic human antibody molecule of this invention involves the use of synthetic oligonucleotides designed to introduce random mutations into preselected domains of the immunoglobulin variable regions of the cloned immunoglobulin gene. Furthermore, the oligonucleotide strategies described herein have particular advantages in creating in a single reaction an extremely large population of different binding sites by the use of degenerate oligonucleotides.

The general structure of a preferred oligonucleotide for use in one of the present methods is described further hereinbelow.

Oligonucleotides for use in the present invention can be synthesized by a variety of chemistries as is well known. An excellent review is "Oligonucleotide Synthesis: A Practical Approach", ed. M. J. Gait, JRL Press, New York, N.Y. (1990). Suitable synthetic methods include, for example, the phosphotriester or phosphodiester methods see Narang et al., *Meth. Enzymol.,* 68:90, (1979); U.S. Pat. No. 4,356,270; and Brown et al., *Meth. Enzymol.,* 68:109, (1979). Purification of synthesized oligonucleotides for use in primer extension and PCR reactions is well known. See, example Ausubel et al., "Current Protocols in Molecular Biology", John Wiley & Sons, New York, (1987). Exemplary synthesis is described in the Examples.

3. Primer Extension Reactions

The term "polynucleotide" as used herein in reference to primers, probes and nucleic acid fragments or segments to be synthesized by primer extension is defined as a molecule comprised of two or more deoxyribonucleotides or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nuc. Acids Res.*, 12:7057–70 (1984); Studier et al., *J. Mol. Biol.*, 189:113–130 (1986); and *Molecular Cloning: A Laboratory Manual, Second Edition,* Sambrook et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197–1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719–736 (1974).

The choice of a primer's nucleotide sequence depends on factors such as the distance on the nucleic acid from the region of the display protein gene into which a binding site is being introduced, its hybridization site on the nucleic acid relative to any second primer to be used, and the like.

The PCR reaction is performed using any suitable method. Generally it occurs in a buffered aqueous solution, i.e., a PCR buffer, preferably at a pH of 7–9, most preferably about 8. Preferably, a molar excess of the primer is admixed to the buffer containing the template strand. A large molar excess of about $10^4$:1 of primer to template is preferred to improve the efficiency of the process.

The PCR buffer also contains the deoxyribonucleotide triphosphates dCTP, dCTP, dGTP, and dTTP and a polymerase, typically thermostable, all in adequate amounts for primer extension (polynucleotide synthesis) reaction. The resulting solution (PCR admixture) is heated to about 90 degrees Celsius (90 C.) to 100 C. for about 1 to 10 minutes, preferably from 1 to 4 minutes. After this heating period the solution is allowed to cool to 54 C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40 C. An exemplary PCR buffer comprises the following: 50 millimolar (mM) KCl; 10 mM Tris-HCl; pH 8.3; 1.5 mM MgCl$_2$; 0.001% (wt/vol) gelatin, 200 micromolar (uM) dATP; 200 uM dTTP; 200 uM dCTP; 200 uM dGTP; and 2.5 units *Thermus aquaticus* DNA polymerase I (U.S. Pat. No. 4,889,818) per 100 microliters (ul) of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SPG RNA polymerase. These polymerases produce a complementary RNA polynucleotide. The high turn over rate of the RNA polymerase amplifies the starting polynucleotide as has been described by Chamberlin et al., *The Enzymes,* ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acids Res.*, 17:711–722 (1989). Amplification systems based on transcription have been described by Gingeras et al., in *PCR Protocols, A Guide to Methods and Applications,* pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process, as is known for PCR.

PCR is typically carried out by thermocycling i.e., repeatedly increasing and decreasing the temperature of a PCR reaction admixture within a temperature range whose lower limit is about 10 C. to about 40 C. and whose upper limit is about 90 C. to about 100 C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990), the teachings of which are hereby incorporated by reference.

Preferred PCR reactions using the oligonucleotides and methods of this invention are described in the Examples.

4. Methods for Producing a Synthetic Antibody

The present invention provides methods for changing the diversity of a monoclonal antibody or a library of monoclonal antibodies of this invention. These methods generally increase the diversity of the library, thereby increasing the pool of possible epitope-binding complexes from which to screen for a desired and improved binding and HIV-neutralizing activity. Alternatively, the methods can be directed at enriching for a class of epitope-binding complexes. The class is typically defined by the ability to bind a particular epitope or family of epitopes present on a preselected antigen or group of antigens.

The method for producing a synthetic monoclonal antibody generally involves (1) introducing by mutagenesis random mutations into a preselected portion of the immunoglobulin variable gene encoded in a phagemid display protein vector by primer extension with an oligonucleotide as described herein, to form a large population of display vectors each capable of expressing different monoclonal antibodies displayed on a phagemid surface display protein, (2) expressing the display protein and antibody on the surface of a filamentous phage particle, and (3) isolating the surface-expressed phage particle using affinity techniques such as panning of phage particles against a preselected target molecule, thereby isolating one or more species of phagemid containing a synthetic monoclonal antibody that binds a preselected target molecule.

An exemplary preparation of a binding site in the CDR3 region of a heavy chain of an immunoglobulin is described in the Examples. The isolation of a particular vector capable of expressing a binding site of interest involves the introduction of the dicistronic expression vector into a host cell permissive for expression of filamentous phage genes and the assembly of phage particles. Typically, the host is *E. coli*. Thereafter, a helper phage genome is introduced into the host cell containing the phagemid expression vector to provide the genetic complementation necessary to allow phage particles to be assembled. The resulting host cell is cultured to allow the introduced phage genes and display protein genes to be expressed, and for phage particles to be assembled and shed from the host cell. The shed phage particles are then harvested (collected) from the host cell culture media and screened for desirable binding properties. Typically, the harvested particles are "panned" for binding with a preselected molecule. The strongly binding particles are then collected, and individual species of particles are clonally isolated and further screened for binding to the target molecule and for HIV neutralization. Phage which produce antibody molecules of desired binding specificity and neutralization capacity are selected.

As a further characterization of the present invention, the nucleotide and corresponding amino acid residue sequence of the gene coding the binding site is determined by nucleic acid sequencing. The primary amino acid residue sequence information provides essential information regarding the binding site's reactivity.

Mutation of nucleic acid can be conducted by a variety of means, but is most conveniently conducted in a PCR reaction during a PCR process of the present invention. PCR mutagenesis can be random or directed to specific nucleotide sequences, as is generally well known. Conducting PCR under conditions favorable to random mutagenesis has been described previously, and is referred to as "error prone PCR". Similarly, directed mutagenesis involves the use of PCR primers designed to target a specific type of mutation into a specific region of nucleotide sequence.

In one embodiment, the invention contemplates increasing diversity of one or more epitope-binding complexes by PCR-directed mutation of a complementarity determining region (CDR) of an antibody variable domain present in an epitope-binding complex polypeptide of this invention. CDR mutagenesis has been previously described in general terms for "humanizing" an antibody by introducing human sequences into the CDR region of a murine antibody. See European Application No. EP 239400.

Thus the invention contemplates a mutagenesis method for altering the immunological specificity of a cloned immunoglobulin gene present in a DNA vector of this invention. The method provides directed mutagenesis in a preselected CDR of an immunoglobulin gene which comprises subjecting a recombinant DNA molecule (rDNA) containing the cloned immunoglobulin gene having a target CDR to PCR conditions suitable for amplifying a preselected region of the CDR. In the method, the rDNA molecule is subjected to PCR conditions that include a PCR primer oligonucleotide as described below constituting the first primer in a PCR primer pair as is well known to produce an amplified PCR product that is derived from the preselected CDR but that includes the nucleotide sequences of the PCR primer. The second oligonucleotide in the PCR amplifying conditions can be any PCR primer derived from the immunoglobulin gene to be mutagenized, as described herein.

Preferred are methods using an oligonucleotide of this invention as described below.

In a related embodiment, therefore, an oligonucleotide is contemplated that is useful as a primer in a polymerase chain reaction (PCR) for inducing mutagenesis in a complementarity determining region (CDR) of an immunoglobulin gene. The oligonucleotide has 3' and 5' termini and comprises (1) a nucleotide sequence at its 3' terminus capable of hybridizing to a first framework region of an immunoglobulin gene, (2) a nucleotide sequence at its 5' terminus capable of hybridizing to a second framework region of an immunoglobulin gene, and (3) a nucleotide sequence between the 3' and 5' termini adapted for introducing mutations during a PCR into the CDR between the first and second framework regions of the immunoglobulin gene, thereby mutagenizing the CDR.

Insofar as immunoglobulin genes have three CDR regions on both the heavy chain and the light chain of an immunoglobulin, each separated by a distinctive framework region, it is to be understood that the above example is readily applicable to introducing mutations into a specific CDR by selection of the above 5' and 3' nucleotide sequences as to hybridize to the framework regions flanking the targeted CDR. Thus the above first and second framework sequences can be the conserved sequences flanking CDR1, CDR2 or CDR3 on either the heavy or light chain.

The length of the 3' and 5' terminal nucleotide sequences of a subject mutagenizing oligonucleotide can vary in length as is well known, so long as the length provides a stretch of nucleotides complementary to the target framework sequences as to hybridize thereto. In the case of the 3' terminal nucleotide sequence, it must be of sufficient length and complementarity to the target framework region located 3' to the CDR to be mutagenized as to hybridize and provide a 3' hydroxyl terminus for initiating a primer extension reaction. In the case of the 5' terminal nucleotide sequence, it must be of sufficient length and complementarity to the target framework region located 5' to the CDR to be mutagenized as to provide a means for hybridizing in a PCR overlap extension reaction as described above to assemble the complete immunoglobulin heavy or light chain.

Framework regions flanking a CDR are well characterized in the immunological arts, and include known nucleotide sequences or consensus sequences as described elsewhere herein. Where a single, preselected immunoglobulin gene is to be mutagenized, the framework-defined sequences flanking a particular CDR are known, or can be readily determined by nucleotide sequencing protocols. Where a repertoire of immunoglobulin genes are to be mutagenized, the framework-derived sequences are preferably conserved, as described elsewhere herein.

Preferably, the length of the 3' and 5' terminal nucleotide sequences are each at least 6 nucleotides in length, and can be up to 50 or more nucleotides in length, although these lengths are unnecessary to assure accurate and reproducible hybridization. Preferred are lengths in the range of 12 to 30 nucleotides, and typically are about 18 nucleotides.

The nucleotide sequence located between the 3' and 5' termini adapted for mutagenizing a CDR can be any nucleotide sequence, insofar as the novel sequence will be incorporated by the above methods. However, the present approach provides a means to produce a large population of mutagenized CDR's in a single PCR reaction by the use of a population of redundant sequences defining randomized or nearly randomized nucleotides in the CDR to be mutagenized.

A preferred oligonucleotide for mutagenizing CDR1, for example, comprises a nucleotide sequence represented by the formula in the direction of 5' to 3': A-B-C, where A and C represent nucleic acid sequences complementary to FR1 and FR2, respectively, B represents a nucleic acid sequence having the formula: $[NNS]_n$, wherein N can independently be any nucleotide, where S is G or C, n is 3 to about 24, and where FR1 and FR2 are the framework regions flanking CDR1 on the 5' and 3' termini, respectively. Preferably, n is 5.

Similarly, a preferred oligonucleotide for mutagenizing CDR3, for example, comprises an nucleotide sequence complementary to the sense (coding) strand of CDR3 represented by the formula in the direction of 5' to 3': C-D-A, where A and C represent nucleic acid sequences complementary to FR3 and FR4, respectively, D represents a nucleic acid sequence having the formula: $[MNN]_n$, wherein N can independently be any nucleotide, where M is C or A, n is 3 to 24, and where FR3 and FR4 are the framework regions flanking CDR3 on the 5' and 3' termini, respectively. Preferably, n is 4.

Thus, the invention contemplates a method for increasing the diversity of a library of filamentous phage particles comprising the steps of: a) providing one or more filamentous phage particles according to the present invention, and b) mutating the immunoglobulin variable domain-coding nucleotide sequence present in each provided phage particle having a DNA expression vector to form a library of phage particles each containing a mutated immunoglobulin variable domain nucleotide sequence.

The providing can include manipulating the genomes of the phage particles in the library in order to isolate the nucleic acids in preparation for a mutagenizing PCR reaction. Manipulations of a phage library to isolate the phage genome for use in a PCR reaction is described elsewhere herein.

Following, mutagenesis of a CDR in a preselected portion to form a library of phage containing synthetic monoclonal antibodies, the invention involves manipulations to change the diversity of the library by enriching the library for a preselected class of epitope-binding complexes. The process generally involves affinity selection of those phage particles in a library that are capable of binding a preselected antigen. The process of affinity selection, or panning, is described in detail in the Examples.

In a related embodiment, the invention contemplates a method for changing the diversity of a library of filamentous phage particles comprising the steps of a) providing a library of filamentous phage particles according to the present invention, b) contacting the provided library with a preselected ligand under conditions sufficient for members of the library to bind to the ligand and form a ligand-phage particle complex, and c) isolating phage particles in the complex away from non-bound library members to form a ligand-enriched library comprising phage particles having binding specificity for the preselected ligand.

In preferred embodiments, the preselected ligand is affixed to a solid support, and the ligand-phage particle complex is formed in the solid phase. This embodiment further comprises the steps of: i) washing the solid support after the contacting step to rinse non-bound library members from the solid support; and ii) eluting any solid-phase bound phage particles off of the solid support. The eluted phage particles are collected, thereby forming isolated phage particles that comprise an enriched library.

Elution can be conducted under a variety of conditions that disrupt the ligand-epitope-binding complex interaction. Typical conditions include high salt or low pH buffers. Particularly preferred are buffers of about pH 1 to 5, preferably about pH 2 to 3. Alternatively, the interaction can be disrupted by competition with an excess amount of the preselected ligand in the elution buffer. Both elution procedures are described in the Examples.

A related embodiment combines the features of both increasing diversity of a library by mutation and enriching the library by panning to "mature" epitope-binding complex affinities for a preselected ligand. Thus it is possible to evolve new binding specificities, and more potent binding specificities, using the present methods for changing library diversity.

The combination of these methods can be configured in a variety of ways, as will be apparent to a skilled practitioner. For example, one can isolate a library, mutagenize (diversify), and then screen (enrich) for a particular binding activity. Alternatively, one can enrich for a particular activity from a library, mutagenize the specific epitope-binding complex and further enrich the library produced by the mutagenesis.

In another permutation on this theme, one can utilize the differences between libraries based on cpIII- and cpVIII-derived membrane anchors due to their inherent differences in valency. Because a library of phage having the cpIII-derived membrane anchor will typically contain only 1 to 4 copies of the epitope-binding complex on the surface of each phage particle, the phage presents a binding complex of relatively "low" valency, approaching one. In contrast, a library of phage having a cpVIII-derived membrane anchor will typically contain 20 to 1000 copies of the epitope-binding complex on the surface of each phage particle, the particle presents a relatively "high" valency. Thus, cpIII-based libraries are referred to as monovalent and cpVIII-based libraries are referred to as multivalent.

Applying the well-known principles of antibody affinity and valence and the methods herein, it is demonstrated that a cpIII-based library can be produced and/or enriched upon screening to contain antibodies with generally higher affinity binding interactions, expressed as dissociation binding constants ($K_d$), of $10^6$ to $10^{12}$ $M^{-1}$, as compared to the broader range of affinities (binding constants of $10^4$ to $10^9$ $M^{-1}$) isolatable conventionally or by using a multivalent reagent found in the cpVIII-based library according to the present invention. Therefore, a cpVIII-based library is useful to isolate a broad range of affinities of epitope-binding complexes from low to high, whereas a cpIII-based library is useful to isolate a narrower range of higher affinity epitope-binding complexes. The high affinity antibodies are particularly preferred for their strong immunoreactivity and attendant selectivity and strong neutralization abilities as demonstrated herein. Preferred antibodies have affinities of at least $10^{-9}$, preferably at least $10^{-10}$, more preferably at least $10^{-11}$, and most preferably at least $10^{-12}$.

The invention also contemplates producing a first enriched library by enrichment of a cpVIII-based library. Thereafter the genes for encoding the epitope-binding complex polypeptides are transferred into a cpIII-based vector, and subsequently enriched for a high affinity binding interaction. In one embodiment, a mutation step can be utilized prior to the transfer into the cpIII-based vector.

Thus, the present invention also contemplates a method for maturing the affinity of an epitope-binding complex encoded by a filamentous phage of this invention comprising the steps of: a) providing the genome of a filamentous phage; b) mutating the immunoglobulin variable domain-coding nucleotide sequence present in the provided genome to form a library of phage particles containing a mutated immunoglobin variable domain nucleotide sequence; c) contacting the library formed in step (b) with a preselected ligand under conditions sufficient for members of the library to bind to the ligand and form a ligand-phage particle complex; and d) isolating phage particles in said complex away from non-bound library members to form a ligand-enriched library comprising phage particles having binding specificity for the preselected ligand.

In a particularly preferred embodiment demonstrated herein, multiple CDR regions are mutagenized through a series of cycles of mutagenesis and enrichment to synthetically evolve a highly superior monoclonal antibody.

For example, an anti-HIV glycoprotein gp120 monoclonal antibody in the form of a phage display protein was first randomly mutagenized in the CDR1 domain to form a first library of phagemids having synthetic antibodies, and then the library was enriched by panning against a preselected ligand, i.e. HIV gp120 in the solid phase. Thereafter, the highest affinity binding phagemids in the library were collected, and one or more were selected for further random mutagenesis in the CDR3 domain to form a second library of phagemids having synthetic antibodies, and the resulting library was then enriched by panning against the preselected ligand gp120 to form a high affinity phagemids having synthetic monoclonal antibodies capable of high affinity binding to HIV gp120. The resulting high affinity antibodies are then screened in conventional virus neutralization assays described herein to identify the synthetic antibodies with the highest neutralizing capacity, and selected as an antibody of this invention.

The sequence of mutagenesis and panning events can be altered. For example, one can mutagenize CDR3 prior to CDR1, or vice versa. Alternatively, one can further screen the first library for neutralization as a refinement of the enrichment step prior to the second mutagenesis and enrichment step.

Thus, in one embodiment, the invention describes a method for producing a synthetic human anti-HIV monoclonal antibody comprising the steps of:
a) providing the genome of filamentous phage encoding a monoclonal antibody having immunoglobulin heavy and light chain variable domains, said heavy chain variable domain present as a fusion polypeptide containing a filamentous phage membrane anchor domain, wherein said monoclonal antibody immunoreacts with HIV;

b) mutating the immunoglobulin heavy chain variable domain-coding nucleotide sequence present in the provided genome to form a first library of mutagenized phage particles containing a mutated immunoglobulin heavy chain variable domain nucleotide sequence;

c) contacting the library formed in step (b) with a preselected ligand under conditions sufficient for members of the library to bind to the ligand and form a first ligand-phage particle complex;

d) isolating phage particles in said first complex away from non-bound library members to form a first ligand-enriched library comprising phage particles having binding specificity for said preselected ligand;

e) providing the genome of filamentous phage from said first ligand-enriched library;

f) mutating the immunoglobulin heavy chain variable domain-coding nucleotide sequence present in the provided genome to form a second library of mutagenized phage particles containing a mutated immunoglobulin heavy chain variable domain nucleotide sequence;

g) contacting the library formed in step (f) with a preselected ligand under conditions sufficient for members of the library to bind to the ligand and form a second ligand-phage particle complex; and h) isolating phage particles in said second complex away from non-bound library members to form a second ligand-enriched library comprising phage particles having binding specificity for said preselected ligand.

In preferred embodiments, the mutating in steps (b) and (f) are directed to the same region of the immunoglobulin heavy chain variable domain. Alternatively, the mutating in steps (b) and (f) can be directed to two different regions of the immunoglobulin heavy chain variable domain. For example, in a preferred method, the mutating in step (b) is directed to a first CDR and the mutating in step (f) is directed to a second CDR. In preferred and exemplary methods, the first and second CDR's are CDR1 and CDR3, respectively.

As applied to HIV, it is particularly preferred where the monoclonal antibody of step (a) immunoreacts with HIV glycoprotein gp120 and where the preselected ligand used in the enrichment steps (c) and (g) is HIV glycoprotein gp120.

The particularly preferred method for inducing mutagenesis in step (b) comprises inducing mutagenesis in a CDR of an immunoglobulin gene in the phagemid genome which comprises amplifying a portion of the CDR of the immunoglobulin gene by polymerase chain reaction (PCR) using a PCR primer oligonucleotide, where the oligonucleotide has 5' and 3' termini and comprises:
a) a nucleotide sequence at the 5' terminus capable of hybridizing to a framework region upstream of the CDR;
b) a nucleotide sequence at the 3' terminus capable of hybridizing to a framework region downstream of the CDR; and
c) a nucleotide sequence between the 5' and 3' termini according to the formula:

$$[NNS]_n,$$

wherein N is independently any nucleotide, S is G or C, or analogs thereof, and n is 3 to about 24, the 3' and 5' terminal nucleotide sequences have a length of about 6 to 50 nucleotides, and sequences complementary thereto. Particularly preferred and exemplary of this embodiment is the method where n is 5, CDR is CDR1, and the upstream and downstream framework regions are FR1 and FR2, respectively.

Also preferred are methods for inducing mutagenesis in step (f) that comprise inducing mutagenesis in a CDR of an immunoglobulin gene in the phagemid genome which comprises amplifying a portion of the CDR of the immunoglobulin gene by polymerase chain reaction (PCR) using a PCR primer oligonucleotide, where the oligonucleotide has 5' and 3' termini and comprises:

a) a nucleotide sequence at the 5' terminus capable of hybridizing to the antisense (noncoding) framework region downstream of the CDR;

b) a nucleotide sequence at the 3' terminus capable of hybridizing to the antisense (noncoding) framework region upstream of the CDR; and c) a nucleotide sequence between the 5' and 3' termini according to the formula:

[MNN]$_n$, wherein N is independently any nucleotide, M is C or A, or analogs thereof, and n is 3 to about 24, the 3' and 5' terminal nucleotide sequences have a length of about 6 to 50 nucleotides, and sequences complementary thereto. Particularly preferred and exemplary of this embodiment is the method where n is 4, CDR is CDR3, and the upstream and downstream framework regions are FR3 and FR4, respectively.

Also contemplated are synthetic monoclonal antibodies immunoreactive with HIV according to the present invention and produced by an embodiment of the above described processes.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of Synthetic Human Fab Heterodimers that Exhibit Enhanced Affinity to gp120 of HIV-1 and Have Increased Neutralizing Ability A. Description of pMT4 and an Overview of the Methods to Obtain CDR1 and CDR3 Randomized gp120-Specific Fab Antibodies The immunoglobulin gene phagemid expression vector, designated as pMT4 to indicate the phagemid rather than the encoded Fab (MT4), contains the heavy and light chain sequences for expressing a Fab heterodimer antibody used as a template for the randomization of the complementarity determining regions (CDR) as shown herein. The pMT4 phagemid as deposited expresses a soluble Fab antibody designated MT4 that binds to the envelope glycoprotein of HIV-1, gp120. The selection of pMT4 from screening an IgG1K bone marrow library generated from an HIV-1 seropositive individual (MT) and characterization thereof has been described by Barbas et al., *J. Mol. Biol.*, 230:812–823 (1993), the disclosure of which is hereby incorporated by reference. The derived amino acid residue sequences of both the heavy and light chain variable domains of the Fab encoded by pMT4 has also been published by Barbas et al., *J. Mol. Biol.*, 230:812–823 (1993).

The pMT4 plasmid was deposited with the American Type Culture Collection, 1301 Parklawn Drive, Rockville, Md., USA (ATCC). The deposit of the plasmid-containing cells is listed under the name MT4 and has been assigned the ATCC accession number 75574. This deposit was made under the provisions of the Budapest Treaty on the International Recognition of the Deposit of Microorganisms for the Purpose of Patent Procedure and the Regulations thereunder (Budapest Treaty) as described in the Examples.

Deposited pMT4 can be manipulated to insert the gene 3 membrane anchor to form pMT4-3 by derivation of nucleotide sequence encoding the anchor from pComb3H-TT, described in Example 2B, by cleavage with, for example, Not I and Xho I, and moving the cleaved fragment into pMT4-3 at the same Not I/Xho I sites.

The phagemid pMT4-3 was used in polymerase chain reaction (PCR) amplifications as described herein to introduce nucleotide substitutions, also referred to as nucleotide mutations, into both CDR1 and CDR3 of the Fab heavy chain in the phagemid, to produce novel Fab antibodies that exhibit enhanced binding and neutralizing characteristics. The pMT4-3 vector was chosen as the template DNA on which randomization was performed as it was produced efficiently in *E. coli* and exhibited high affinity to gp120 and neutralization of HIV-1 infection in cells.

The methods of producing higher affinity gp120 Fab antibodies of this invention that exhibit enhanced ability to inhibit HIV-1 infection of cells involved the following steps presented as an overview: 1) The heavy chain CDR1 of pMT4-3 was first randomized through the use of polymerase chain reaction (PCR); 2) Amplification products from the PCR containing randomized CDR1 were ligated back into pMT4-3 to form a randomized library; 3) Following expression of bacteriophage coat protein 3-anchored Fab from the library, the Fab-expressing phage were panned against gp120, strain IIIb, resulting in the selection of gp120-specific CDR1 randomized Fabs; 4) The phagemid that encoded the selected Fabs were then subjected to randomization of 12 nucleotides in CDR3 in a one-step PCR amplification; 5) The resultant amplification products having both CDR1 and a portion of CDR3 randomized were then ligated back into pMT4-3 and the expression and panning process was repeated; 6) Following selection of gp12O-specific CDR1 and CDR3 randomized Fabs, the corresponding phagemids were sequenced and the amino acid residue sequence was derived therefrom; and lastly 7) Both surface plasmon resonance analysis to determine the binding affinity and neutralization assays to determine the ability of the antibody to inhibit HIV-1 infection were performed as a final characterization of the resultant CDR1 and CDR3 randomized gp120-specific Fabs.

The above-enumerated steps are presented in detail below in the following subsections.

B. Preparation of Randomized CDR1 of the Heavy Chain Variable Domain of Phagemid MT4-3

1) Randomization by Overlap PCR

Libraries having a heavy chain variable domain randomized CDR1 were produced with two different approaches. Overlap PCR was used as described herein for one approach. An alternative approach utilized a one-step PCR amplification process as described in Example 1B2) below. Randomization of heavy chain CDR1 in Fabs of this invention were derived from the latter one-step PCR approach.

To randomize CDR1 in the heavy chain variable domain of pMT4-3 described in Example 1A above, two separate PCR amplifications were performed as described herein followed by a third overlap PCR amplification that resulted in the annealing of the two previous amplification products, that was then followed by a third amplification. The nucleotide sequence of the heavy chain variable domain of template pMT4-3 is shown in FIG. 4 and is listed in SEQ ID NO 7. To facilitate subsequent PCR amplifications and subcloning, the pMT4-3 template was first mutagenized by PCR to introduce a Hind III restriction site to cut at nucleotide position 60 as shown in FIG. 4 and SEQ ID NO 7. The original guanine (G) nucleotide at position 60 in the coding strand was changed to an adenine (A) using PCR site-directed mutagenesis methods familiar to one of ordinary skill in the art. As a result of the site-directed mutagenesis, the pMT4-3 template contained an adenine nucleotide at position 60 along with the PCR amplified complementary thymine nucleotide. The coding sequence of the pMT4-3 heavy chain variable domain having the mutagenized bases at position 60 is shown in FIG. 4 and SEQ ID NO 7. This mutagenized pMT4-3 was then used for all subsequent PCR amplifications to introduce CDR randomizations.

The nucleotide positions that were randomized in the heavy chain of pMT4-3 began at nucleotide position 82 and ended at position 96. The template pMT4-3 DNA heavy chain sequence at that specified site encoded the five total amino acid residues in CDR1. The amino acid residue sequence of CDR1 encoded by pMT4-3 was Asn-Phe-Val-Ile-His (SEQ ID NO 8), as shown in the complete amino acid residue sequence of the heavy chain variable domain in FIG. 1, labeled MT4. In FIG. 1 and corresponding SEQ ID NO 1, the CDR1 of MT4-3 begins at amino acid residue position 28 and ends at 32. This corresponds to the conserved Kabat positions 31–35.

A pool of degenerate oligonucleotide primers, designated 12cdr1h3-f having the nucleotide formula shown below, synthesized by Operon Technologies, Alameda, Calif., were used for randomizing the heavy chain CDR1 of pMT4-3. The five triplet codons for introducing randomized nucleotides had the repeating sequence NNS, where S can be either G or C and N can be A, C, G or T.

The first PCR amplification resulted in the amplification of the region of the heavy chain fragment in the pMT4-3 phagemid vector clone of most of framework region 1 (FR1). To amplify this region, the following primer pairs were used. The 5' oligonucleotide primer, FTX3, having the nucleotide sequence 5'-GCAATTAACCCTCACTAAAGGG-3' (SEQ ID NO 9), hybridized to the noncoding strand of the heavy chain corresponding to the region 5' (vector sequence) of and including the first two nucleotides of FR1. The 3' oligonucleotide primer, 12h3-b, having the nucleotide sequence 5'-AGAAGCTTGACAAGAAGAAACCTTC-3' (SEQ ID NO 10) hybridized to the coding strand of the heavy chain ending at 15 nucleotides from the end of framework 1. The oligonucleotide primers were synthesized by Operon Technologies.

The PCR reaction was performed in a 100 microliter (ul) reaction containing one microgram (ug) of each of oligonucleotide primers FTX3 and 12h3-b, 200 millimolar (mM) dNTP's (dATP, dCTP, dGTP, dTTP), 1.5 mM $MgCl_2$ Taq polymerase (5 units) (Perkin-Elmer Corp., Norwalk, Conn.), 10 nanograms (ng) of template pMT4-3, and 10 ul of 10×PCR buffer purchased commercially (Perkin-Elmer Corp.). Thirty-five rounds of PCR amplification in a Perkin-Elmer Cetus 9600 GeneAmp PCR System thermocycler were then performed. The amplification cycle consisted of denaturing at 94 degrees C. (94 C.) for one minute, annealing at 50 C. for one minute, followed by extension at 72 C. for two minutes. To obtain sufficient quantities of amplification product, 15 identical PCR reactions were performed.

The resultant PCR amplification products were then gel purified on a 1.5% agarose gel using standard electroelution techniques as described in "Molecular Cloning: A Laboratory Manual", Sambrook et al., eds., Cold Spring Harbor, N.Y. (1989). Briefly, after gel electrophoresis of the digested PCR amplified Fab-display encoding synthetic binding sites, the region of the gel containing the DNA fragments of predetermined size was excised, electroeluted into a dialysis membrane, ethanol precipitated and resuspended in buffer containing 10 millimolar (mM) Tris-HCl [Tris (hydroxymethyl)aminomethane-hydrochloride] at pH 7.5 and 1 mM EDTA (ethylenediaminetetraacetic acid) to a final concentration of 50 nanograms/milliliter (ng/ml).

The purified resultant PCR amplification products from the first reaction were then used in an overlap extension PCR reaction with the products of the second PCR reaction, both as described below, to recombine the two products into reconstructed heavy chains containing randomized CDR1.

The second PCR reaction resulted in the amplification of the heavy chain overlapping framework 1 with the above products and extending 3' of framework 4 of the heavy chain. To amplify this region for randomizing the encoded five amino acid residue sequence of CDR1, the following primer pairs were used. The 5' coding oligonucleotide primer pool as described above, designated 12cdr1h3-f, had the nucleotide sequence represented by the formula, 5'-GAAGGTTTCTTGTCAAGCTTCTGGATACAGATTC-AGTNNSNNSNNSNNSNNSTGGGTGCGCCAGGCCCC-C-3' (SEQ ID NO 11), where N can be either A, C, G, or T and S is G or C. The 3' noncoding primer, R3B, hybridized to the coding strand at the 3' end of CH1 having the sequence 5'-TTGATATTCACAACGAATGG-3' (SEQ ID NO 12). The 5' end of the oligonucleotide primer pool is complementary to the 3' end of framework 1 and the 3' end of the oligonucleotide primer pool is complementary to the 5' end of framework 2. The region between the two specified ends of the primer pool is represented by a 15-mer NNS degeneracy. The second PCR reaction was performed on a second aliquot of pMT4-3 template in a 100 ul reaction as described above containing 1 ug of each of oligonucleotide primers as described. The resultant PCR products encoded a diverse population of randomized heavy chain CDR1 regions of 5 amino acid residues in length. The products were then gel purified as described above.

For the annealing reaction of the two PCR amplifications, 1 mg each of gel purified products from the first and second PCR reactions were then admixed and fused in the absence of primers for 35 cycles of PCR as described above. The resultant fusion product was then amplified with 1 ug each of FTX3 and R3B oligonucleotide primers as a primer pair in a final PCR reaction to form a complete heavy chain fragment by overlap extension. The overlap PCR amplification was performed as described above.

To obtain sufficient quantities of amplification product, 15 identical overlap PCR reactions were performed. The resulting heavy chain fragments extended from 5' to framework 1 to the end of CH1 and had randomized CDR1 for encoding 5 amino acid residues. The CDR1-randomized heavy chain fragment amplification products of approximately 880 base pairs (bp) in length in each of the 15 reactions were first pooled and then gel purified as described above prior to their religation into the pMT4-3 surface display phagemid expression vector to form a library for subsequent screening against gp120. The ligation procedure in creating expression vector libraries and the subsequent expression of the heavy chain CDR1-randomized pMT4-3 clones was performed as described in Example 1C.

2) Randomization by One-Step PCR

An alternative approach for randomizing CDR1 in a heavy chain variable domain to produce heavy chain CDR1-randomized Fabs of this invention was performed with one PCR mutagenesis step as described herein. The Fabs of this invention having a CDR1-randomized heavy chain variable domain as described in the following Examples were obtained from screening the phagemid-displayed Fab libraries produced from the one-step PCR approach.

Instead of performing three PCR amplifications to produce one full-length variable domain having a mutagenized CDR1 as described in Example 1B1) for overlap PCR, in one-step PCR, the amplifications were performed to utilize the Hind III restriction site preceding the heavy chain CDR1 that was previously introduced into the pMT4-3 phagemid vector template as described in Example 1B1). The nucleotide sequence of the heavy chain variable domain of template pMT4-3 is shown in FIG. 4 and is listed in SEQ ID NO 7. The region of the template that was randomized for introducing mutations into CDR1 was as previously described for overlap PCR. Thus, to randomize CDR1, the previously described primers, the mutagenizing coding primer 12cdr1h3-f (SEQ ID NO 11) and the 3' noncoding primer R3B (SEQ ID NO 12), were used to introduce randomized nucleotides into the heavy chain CDR1 with the PCR protocol as described in Example iBi) and to amplify sequences beginning at nucleotide position 45 as shown in FIG. 4 and in SEQ ID NO 7 extending into CH1 as previously described.

The resultant PCR products were gel purified, digested with Hind III and Spe I, and gel purified. The Hind III/Spe I digest resulted in a PCR product having a Hind III 5' coding overhanging end, the 5' end of which corresponded with nucleotide position 60 of the pMT4-3 heavy chain variable domain sequence shown in FIG. 4 and in SEQ ID NO 7 and a Spe I 3' end in framework 4 of the heavy chain variable domain.

The double digested PCR products were then directionally ligated into a similarly digested pMT4-3 vector in which the unmutagenized light chain variable domain for encoding Fab MT4 was retained. The Hind III digest of pMT4-3, due to the introduced Hind III site as described in Example 1B1), cut between nucleotide positions 59 and 60 as shown in FIG. 4 of pMT4-3 and in SEQ ID NO 7 leaving the adenine base in position 59 at the 3' coding end of a linearized vector along with a noncoding overhanging end to allow for directional ligation of the digested PCR products into the digested pMT4-3 vector.

Thus, the library of randomized products that were double digested with Hind III and Spe I were directionally ligated into a similarly digested pMT4-3 vector to form a library of circularized pMT4-3 vectors having a CDR1-randomized heavy chain variable domain and a unmutagenized light chain variable domain from the pMT4-3 vector as described in Example 1C. The ligation resulted in the in-frame ligation of the PCR amplified randomized heavy chain variable domain beginning at position 60 with the nucleotide sequence encoding the 5' end of the heavy chain from nucleotide positions 1 to 59. The resultant phagemid library produced from one-step PCR for introducing randomized nucleotide sequences into the heavy chain variable domain of pMT4-3 were then screened as described in Example 1D and used to derived the CDR1-randomized heavy chain variable domain Fabs described in this invention.

C. Preparation of a Phagemid-Displayed Fabs Having Randomized CDR1

The phagemid pMT4-3 containing heavy and light chain variable domain sequences is a pComb3 phagemid expression vector that provides for the expression of phage-displayed anchored proteins. The pComb3 expression vector has been designed to allow for anchoring of expressed proteins on the bacteriophage coat protein 3. Gene III of filamentous phage encodes this 406-residue minor phage coat protein, cpIII (cp3), which is expressed prior to extrusion in the phage assembly process on a bacterial membrane and accumulates on the inner membrane facing into the periplasm of E. coli.

In practicing this invention to obtain expression of Fab-displayed proteins containing a randomized CDR on the phage surface, the heavy (Fd consisting of $V_H$ and $C_H1$) and light (kappa) chains ($V_L$, $C_L$) of antibodies were first targeted to the periplasm of E. coli for the assembly of heterodimeric Fab molecules.

In this system, the first cistron encoded a periplasmic secretion signal (pelB leader) operatively linked to the fusion protein, Fd-cpIII. The second cistron encoded a second pelB leader operatively linked to a kappa light chain. The presence of the pelB leader facilitated the coordinated but separate secretion of both the fusion protein containing the synthetic binding site and light chain from the bacterial cytoplasm into the periplasmic space.

In this process, each chain was delivered to the periplasmic space by the pelB leader sequence, which was subsequently cleaved. The heavy chain containing the synthetic binding was anchored in the membrane by the cpIII membrane anchor domain while the light chain was secreted into the periplasm. Fab molecules were formed from the binding of the heavy chain with the soluble light chains.

The phagemid vector, designated pComb3, allowed for both surface display and soluble forms of Fabs. The vector was designed for the cloning of combinatorial Fab libraries. Xho I and Spe I sites were provided for cloning complete PCR-amplified heavy chain (Fd) sequences consisting of the region beginning with framework 1 and extending through framework 4. A Hind III site engineered into pMT4-3 provided for directional in-frame ligation of partial PCR amplified heavy chain variable domain fragments. An Aat II restriction site is also present in the heavy chain CDR3. The presence of the Aat II site allowed for the insertion of Xho I/Aat II digests of the PCR products prepared in Example 1E that contain sequences beginning with framework 1 and extending to the end of the CDR3 domain in which the sequences for encoding both mutagenized CDR1 and CDR3 are located. The insertion of an Xho I/Aat II digest into pMT4-3 as described in Example 1F resulted in the fusion of the randomized pMT4-3 heavy chain variable domain with framework 4 already present in the pMT4-3 vector. Thus, the ligation of the final heavy chain mutagenized nucleotide sequence prepared in Example 1E resulted in the in-frame ligation of a complete heavy chain fragment consisting of PCR amplified framework 1 through CDR3 and retained pMT4-3 framework 4. The cloning sites in the pComb3 expression vectors were compatible with previously reported mouse and human PCR primers as described by Huse et al., Science, 246:1275–1281 (1989) and Persson et al., Proc. Natl. Acad. Sci., USA, 88:2432–2436 (1991). The nucleotide sequence of the pelB, a leader sequence for directing the expressed protein to the periplasmic space, was as reported by Huse et al., Science, 246:1275–1281 (1989).

The vector also contained a ribosome binding site as described by Shine et al., Nature, 254:34 (1975). The sequence of the phagemid vector, pBluescript, which includes ColE1 and F1 origins and a beta-lactamase gene, has been previously described by Short et al., Nuc. Acids Res., 16:7583–7600 (1988) and has the GenBank Accession Number 52330 for the complete sequence. Additional restriction sites, Sal I, Acc I, Hinc II, Cla I, Hind III, Eco RV, Pst I and Sma I, located between the Xho I and Spe I sites of the empty vector were derived from a 51 base pair stuffer fragment of pBluescript as described by Short et al., *Nuc. Acids Res.*, 16:7583–7600 (1988). A nucleotide sequence that encodes a flexible 5 amino acid residue tether sequence which lacks an ordered secondary structure was juxtaposed between the Fab and cp3 nucleotide domains so that interaction in the expressed fusion protein was minimized.

Thus, the resultant combinatorial vector, pComb3, consisted of a DNA molecule having two cassettes to express one fusion protein, Fd/cp3, and one soluble protein, the light chain. The vector also contained nucleotide residue sequences for the following operatively linked elements listed in a 5' to 3' direction: a first cassette consisting of LacZ promoter/operator sequences; a Not I restriction site; a ribosome binding site; a pelB leader; a spacer region; a cloning region bordered by 5' Xho and 3' Spe I restriction sites; the tether sequence; the sequences encoding bacteriophage cp3 followed by a stop codon; a Nhe I restriction site located between the two cassettes; a second lacZ promoter/operator sequence followed by an expression control ribosome binding site; a pelB leader; a spacer region; a cloning region bordered by 5' Sac I and a 3' Xba I restriction sites followed by expression control stop sequences and a second Not I restriction site.

In the above expression vector, the Fd/cp3 fusion and light chain proteins were placed under the control of separate lac promoter/operator sequences and directed to the periplasmic space by pelB leader sequences for functional assembly on the membrane. Inclusion of the phage F1 intergenic region in the vector allowed for the packaging of single-stranded phagemid with the aid of helper phage. The use of helper phage superinfection allowed for the expression of two forms of cp3. Consequently, normal phage morphogenesis was perturbed by competition between the Fd/cp3 fusion and the native cp3 of the helper phage for incorporation into the virion. The resulting packaged phagemid carried native cp3, which is necessary for infection, and the encoded Fab fusion protein, which is displayed for selection. Fusion with the C-terminal domain was necessitated by the phagemid approach because fusion with the infective N-terminal domain would render the host cell resistant to infection.

The pComb3 expression vector described above forms the basic construct of the MT4 Fab display phagemid expression vector, also referred to as pMT4-3, used in this invention for the production of synthetic human Fab antibodies against gp120 of HIV-1.

1) Phagemid Library Construction

In order to obtain expressed synthetic human Fab antibodies having both heavy and light chain variable domains, phagemid libraries were constructed. The libraries provided for the expression of recombinant human Fab antibodies having heavy and light chains where CDR1 was randomized in the heavy chain as described in Example 1B.

For preparation of phagemid libraries for expressing the PCR products prepared in Example 1B, the PCR products from overlap PCR were first digested with Xho I and Spe I and separately ligated with similarly digested original (i.e., not randomized) pMT4-3 phagemid expression vectors prepared as described in Example 1A. The Xho I and Spe I sites were present in the framework 1 region and CHI domain, respectively. The ligation resulted in operatively linking the heavy chain variable domain from framework 1 to the end of framework 4 to the pMT4-3 vector, located 5' to the cp3 gene. Since the amplification products were inserted into the template pMT4-3 expression vector that originally had both heavy and light chain variable domain sequences for expressing Fab MT4, only the heavy chain domain was replaced leaving the rest of the pMT4-3 expression vector unchanged. In other words, the newly randomized CDR1 heavy chain amplification products were religated back into pMT4-3 with the original pMT4-3 light chain variable domain. Thus, upon expression from the recombinant clones, the expressed Fabs contained a CDR1-randomized heavy chain and the pMT4-3 light chain sequence, the latter of which is shown in FIG. 2 and in SEQ ID NO 6. The PCR products from the one-step PCR approach were digested with Hind III and Spe I and then separately ligated with similarly digested pMT4-3 expression vectors. The result was the same as that described for overlap PCR.

The pMT4-3 light chain variable domain nucleotide sequence was retained unchanged throughout the mutagenesis procedure. Therefore, all the preferred anti-gp120 Fab antibodies obtained by the methods of this invention as described in Example 1 contain the light chain amino acid residue sequence encoded by the original pMT4-3.

Phagemid libraries for expressing each of the Fab display synthetic binding sites of this invention were prepared in the following procedure. To form circularized vectors containing the PCR product insert, 640 ng of the digested PCR products were admixed with 2 ug of the linearized pMT4-3 phagemid vector and ligation was allowed to proceed overnight at room temperature using 10 units of BRL ligase (Gaithersburg, Md.) in BRL ligase buffer in a reaction volume of 150 ul. Five separate ligation reactions were performed to increase the size of the phage library having randomized CDR1. Following the ligation reactions, the circularized DNA was precipitated at −20 degrees Celsius (−20 C.) for 2 hours by the admixture of 2 ul of 20 mg/ml glycogen, 15 ul of 3 M sodium acetate at pH 5.2 and 300 ul of ethanol. DNA was then pelleted by microcentrifugation at 4 C. for 15 minutes. The DNA pellet was washed with cold 70% ethanol and dried under vacuum. The pellet was resuspended in 10 ul of water and transformed by electroporation into 300 ul of *E. coli* XL1-Blue cells to form a phage library.

After transformation, to isolate phage on which Fabs having mutagenized CDR1 were induced for subsequent panning on the gp120 glycoprotein as described in Example 1D, 3 ml of SOC medium (SOC was prepared by admixture of 20 grams (g) bacto-tryptone, 5 g yeast extract and 0.5 g NaCl in 1 liter of water, adjusting the pH to 7.5, autoclaving followed by admixture of 20 mM glucose) were admixed and the culture was shaken at 220 rpm for 1 hour at 37 C. After that, 10 ml of SB (SB was prepared by admixing 30 g tryptone, 20 g yeast extract, and 10 g Mops buffer per liter with pH adjusted to 7) containing 20 ug/ml carbenicillin and 10 ug/ml tetracycline were admixed and the admixture was shaken at 300 rpm for an additional hour. This resultant admixture was admixed to 100 ml SB containing 50 ug/ml carbenicillin and 10 ug/ml tetracycline and shaken for 1 hour, after which helper phage VCSM13 ($10^{12}$ pfu) were admixed and the admixture was shaken for an additional 2 hours at 37 C. After this time, 70 ug/ml kanamycin was admixed and maintained at 30 C. overnight. The lower temperature resulted in better heterodimer incorporation on the surface of the phage. The supernatant was cleared by centrifugation (4000 rpm for 15 minutes in a JALO rotor at 4 C.). Phage were precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4 C.). Phage pellets were resuspended in 2 ml of PBS and microcentrifuged for three minutes to pellet debris, transferred to fresh tubes and stored at −20 C. for subsequent screening as described below.

For determining the titering colony forming units (cfu), phage (packaged phagemid) were diluted in SB and 1 ul was used to infect 50 ul of fresh ($A_{OD600}$=1) E. coli XL1-Blue cells grown in SB containing 10 ug/ml tetracycline. Phage and cells were maintained at room temperature for 15 minutes and then directly plated on LB/carbenicillin plates. The resulting phage library containing randomized CDR1 heavy chain genes were thus found to contain about $2 \times 10^7$ phage particles (cfu).

For subsequent screening of the library, the library was amplified to a population size of about $10^{11}$ cfu containing a diversity of $2 \times 10^7$ particles, and the amplified library used as needed. Amplification of a phage library was conducted as described below for amplifying eluted phage in Example 1D1).

D. Selection of Anti-gp120 Fab Heterodimers Expressed on Phage Surfaces

1) Multiple Pannings of the Phage Library

The phage library produced in Example 1C from the one-step PCR approach was panned against recombinant gp120 of HIV-1 strain IIIb as described herein on coated microtiter plate select for anti-HIV-1 heterodimers.

The panning procedure used, comprised of several rounds of recognition and replication, was a modification of that originally described by Parmley and Smith (Parmley et al., Gene, 73:305–318 (1988). Four rounds of panning were performed to enrich for specific antigen-binding clones. For this procedure, four wells of a microtiter plate (Costar 3690) were coated overnight at 4 C. with 25 ul of 40 ug/ml gp120 (American Biotechnologies, Ossining, N.Y.) prepared above in 0.1 M bicarbonate, pH 8.6. The wells were washed twice with water and blocked by completely filling the well with 3% (w/v) BSA in PBS and maintaining the plate at 37 C. for one hour. After the blocking solution was shaken out, 50 ul of the amplified phage suspension prepared above (typically $10^{11}$ cfu) were admixed to each well, and the plate was maintained for 2 hours at 37 C.

Phage were removed and the plate was washed once with water. Each well was then washed 10 times with TBS/Tween (50 mM Tris-HCl at pH 7.5, 150 mM NaCl, 0.5% Tween 20) over a period of 1 hour at room temperature where the washing consisted of pipetting up and down to wash the well, each time allowing the well to remain completely filled with TBS/Tween between washings. The plate was washed once more with distilled water and adherent phage were eluted by the addition of 50 ul of elution buffer (0.1 M HCl, adjusted to pH 2.2 with solid glycine, containing 1 mg/ml BSA) to each well followed by maintenance at room temperature for 10 minutes. The elution buffer was pipetted up and down several times, removed, and neutralized with 3 ul of 2 M Tris base per 50 ul of elution buffer used.

The population of eluted phage was amplified to increase the total number of particles in the library and to facilitate subsequent titering of the library. To that end, eluted phage were used to infect 2 ml of fresh ($OD_{600}$=1) E. coli XL1-Blue cells for 15 minutes at room temperature, after which time 10 ml of SB containing 20 ug/ml carbenicillin and 10 ug/ml tetracycline were admixed. Aliquots of 20, 10, and 1/10 ul were removed from the culture for plating to determine the number of phage (packaged phagemids) that were eluted from the plate. The culture was shaken for 1 hour at 37 C., after which it was added to 100 ml of SB containing 50 ug/ml carbenicillin and 10 ug/ml tetracycline and shaken for 1 hour. Helper phage VCSM13 ($10^{12}$ pfu) were then added and the culture was shaken for an additional 2 hours. After this time, 70 ug/ml kanamycin were added and the culture was incubated at 37 C. overnight to form a population of amplified phage. Phage preparation and further panning were repeated as described above for a total of 4 rounds of panning.

Following each round of panning, the percentage yield of phage can be determined, where % yield—(number of phage eluted/number of phage applied)×100. The initial phage input ratio was calculated based on titering the amplified phage population on selective plates to be approximately $10^{11}$ cfu for each round of panning. The final phage output ratio can be determined by infecting two ml of logarithmic phase XL1-Blue cells as described above and plating aliquots on selective plates. Typically, the output of phage eluted from the panning procedure was about $10^5$–$10^6$ cfu. From this panning procedure, clones were selected from the Fab library for their ability to bind to glycosylated recombinant gp120 from the IIIB strain of HIV-1. The selected clones had randomized CDR1 heavy chain variable domains and the light chain variable domain sequence from pMT4-3.

The resulting selected clones that bound gp120 were sequenced to determine the CDR1 heavy chain sequence as described in Example 1D1).

2) Nucleic Acid Sequence Analysis Comparison Between HIV-1 Specific Monoclonal Antibody Fabs and the Corresponding Derived Amino Acid Residue Sequence Following Randomization of CDR1

Nucleic acid sequencing of the CDR1 randomized clones produced in Example 1D1) was performed on 12 randomly chosen soluble double-stranded Fab-expressing DNA using Sequenase 1.0 (USB, Cleveland, Ohio). Alignment of derived sequences with one another and with the Genbank database made use of the MacVector suite of programs. The derived heavy chain amino acid residue sequences of 12 selected specific synthetic gp120-specific Fabs and MT4 are shown in FIG. 5 under column heading Experiment A. The alignment of the variable heavy chain domains as shown in FIG. 5 reveals that in CDR1 the original MT4 gp120-specific Fab obtained from screening a bone marrow library from an HIV-1 seropositive individual, the amino acid residue sequence was Asn-Phe-Val-Ile-His (SEQ ID NO 8). Sequence comparisons indicated a preference for asparagine (N) at position 31, an aromatic residue at position 32, serine (S) or threonine (T) primarily at position 33, branched hydrophobic residues at position 34, and hydrophobic and/or aromatic residues at position 35. The amino acid residue positions 31–35 have been referred to on the basis on conserved Kabat position numbering. The actual amino acid residue position in the complete variable domain amino acid residue sequences shown in FIG. 1 begin and end at 28–32, respectively, resulting from a shortened framework 1. The 12 amino acid residue sequences, indicated in Experiment A for CDR1 of the 12 selected Fabs have been assigned SEQ ID NOs 14–25 as follows: Arg-Tyr-Thr-Val-Phe (SEQ ID NO 14), Asn-Trp-Ser-Val-Met (SEQ ID NO 15), Gly-Tyr-Thr-Leu-Met (SEQ ID NO 16), Asn-Phe-Thr-Leu-Leu (SEQ ID NO 17), His-Tyr-Ser-Leu-Met (SEQ ID NO 18), Asn-Trp-Val-Val-His (SEQ ID NO 19), Asn-Phe-Ser-Ile-Met (SEQ ID NO 20), Asn-Phe-Ala-Ile-His (SEQ ID NO 21), Asn-Phe-Thr-Met-Val (SEQ ID NO 22), Asn-Phe-Thr-Leu-Gln (SEQ ID NO 23), Tyr-Phe-Thr-Met-His (SEQ ID NO 24), and Ser-Tyr-Pro-Leu-His (SEQ ID NO 25).

The CDR3 in the heavy chain domain of the selected clones was then randomized as described in Example 1E to form a phagemid having randomized CDR1 and CDR3 for selection on gp120.

E. Preparation of Randomized CDR3 of the Heavy Chain Variable Domain of CDR1-Randomized Fab-Expressing Clones The selected CDR1-randomized heavy chain Fab-expressing clones from Example 1D were subjected to additional PCR amplifications in order to selectively randomize 12 nucleotides in the heavy chain CDR3 sequence of those clones. The nucleotide position in which the nucleotide randomization was directed began at nucleotide position 292 and ended at position 303 as shown in FIG. 4 and SEQ ID NO 7, of the heavy chain sequence of the original pMT4-3 phagemid. The 12 nucleotides as specified were randomized with a pool of degenerate oligonucleotide primers have a repeat of NNK, where N can either be A, C, G or T, and K is either G or T, as written in the 5' to 3' direction of the coding strand. In this instance, since the 3' end of the heavy chain was being randomized, the oligonucleotide primer pool was the 3' primer. The degenerate oligonucleotides, designed for incorporating the randomized nucleotides, thus were the anti-sense or noncoding strand that hybridized to the coding strand in the PCR amplification. The complementary sequence of NNK is NNM, where N has been defined above, and M is either A or C, and NNM is written in the 3' to 5' direction. The NNM repeat is written MNN in the convention of 5' to 3'. The degeneracy repeats for 4 times in the degenerate oligonucleotide pool.

The noncoding degenerate oligonucleotide primer pool, designated 12-4-cdr3, written in the 5' to 3' direction, had the nucleotide sequence 5'-CCCTTTGCCCCAGACGTCCATATAATAATTGTCCT-GGGGAGAATCATCMNNMNNMNNMNNCCCCACTC-TCGCACA-3' (SEQ ID NO 13). The 12-4-cdr3 primer had a natural Aat II restriction site for allowing the insertion of an Xho I and Aat II restricted amplification product into a similarly digested pMT4-3 phagemid as described below in Example 1F. The 5' oligonucleotide primer used in amplifying the CDR1-mutagenized selected clones from Example 1D was FTX3 described in Example 1C having the nucleotide sequence in SEQ ID NO 9.

The PCR amplification was performed as described in Example 1C with the exception that overlap PCR was not necessitated in this case as the entire heavy chain variable domain was amplified in one reaction extending from before and including framework 1 to the middle of framework 4. The resultant PCR products were purified as described in Example 1C and subsequently reinserted as described in Example 1F into a linearized pMT4-3 phagemid having the light chain variable domain of pMT4-3.

F. Preparation of a Phagemid-Displayed Fabs Having Randomized CDR1 and CDR3

The amplification products produced as described in Example 1E in which the heavy chain variable domain CDR1 and a 12 nucleotide sequence of CDR3 were randomized were then digested with Xho I and Aat II for ligation in a similarly digested original pMT4-3 phagemid. The Xho I site was present in the first six nucleotides of the heavy chain framework 1 region while the Aat II site was the last six nucleotides of CDR3. The ligation of a population of amplified Xho I/Aat II restriction digested heavy chain CDR1- and CDR3-mutagenized products resulted in the in-frame ligation of this portion of the heavy chain to the framework 4 region retained from pMT4-3. Thus, in stepwise randomizations of CDR1 and CDR3, only those specified nucleotides were randomized in the nucleotide sequence of pMT4-3 heavy chain variable domain. As previously described, the light chain of pMT4-3 was retained unchanged.

The resultant ligated pMT4-3 having a randomized heavy chain domain in the CDR1 and CDR3 was then processed as described in Example 1C for subsequent transformation into XL1-Blue. Following transformation, the phage were expressed as previously described to result in the phage-display of Fab antibodies having a randomized heavy chain domain in the CDR1 and CDR3 on a library of phage. The phage library was titered as before and contained about $8 \times 10^6$ phage particles (cfu). For subsequent manipulations, the library was first amplified to provide a stock library of $10^{11}$ cfu as described in Example 1D.

A second panning selection protocol which included 6 rounds of panning was then performed on the amplified library as described in Example 1D to obtain Fabs that bound to gp120. From the panning procedure, eight gp120-specific Fab heterodimers having heavy chain CDR1 and CDR3 randomized amino acid residue sequences and the original MT4 light chain sequence shown in FIG. 2 and listed in SEQ ID NO 6 were selected and further characterized as described in Examples 1G and 1H.

G. Nucleic Acid Sequence Analysis Comparison Between HIV-1 Specific Monoclonal Antibody Fabs and the Corresponding Derived Amino Acid Residue Sequence In order to further characterize, by sequence analysis and functional characteristics, the specificity of the mutagenized heterodimers expressed on the surface of phage as described above, soluble Fab heterodimers from acid eluted phage were prepared.

To prepare soluble heterodimers, phagemid DNA from the gp120-reactive clones prepared above was isolated and digested with Spe I and Nhe I. Digestion with these restriction enzymes produced compatible cohesive ends. The 4.7-kb DNA fragment lacking the gene III portion was gel-purified (0.6% agarose) and self-ligated. Transformation of E. coli XL1-Blue afforded the isolation of recombinants lacking the cpIII fragment. Clones were examined for removal of the cpIII fragment by Xho I-Xba I digestion, which should yield an 1.6-kb fragment. Clones were grown in 100 ml SB containing 50 ug/ml carbenicillin and 20 mM $MgCl_2$ at 37 C. until an $OD_{600}$ of 0.2 was achieved. IPTG (1 mM) was added and the culture grown overnight at 30 C. (growth at 37 C. provides only a slight reduction in heterodimer yield). Cells were pelleted by centrifugation at 4000 rpm for 15 minutes in a JA10 rotor at 4 C. Cells were resuspended in 4 ml PBS containing 34 ug/ml phenylmethylsulfonyl fluoride (PMSF) and lysed by sonication on ice (2–4 minutes at 50% duty). Debris was pelleted by centrifugation at 14,000 rpm in a JA20 rotor at 4 C. for 15 minutes. The supernatant was stored at −20 C. For the study of a large number of clones, 10 ml cultures provided sufficient heterodimer for analysis. In this case, sonications were performed in 2 ml of buffer.

Nucleic acid sequencing was performed on the soluble double-stranded Fab-expressing DNA using Sequenase 1.0 (USB, Cleveland, Ohio). The derived heavy chain amino acid residue sequences of four selected specific synthetic gp120-specific Fabs are shown in FIG. 1. The selected synthetic Fabs have been designated 3b1, 3b3, 3b4 and 3b9. The derived heavy chain amino acid residue sequences of eight selected specific synthetic gp120-specific Fabs are shown in FIG. 5. The eight sequences shown in FIG. 5 include Kabat identified amino acid residues 31 to 35 of CDR1 and amino acid residues 96 to 99 of CDR3 of the Fabs 3b1, 3b3, 3b4, and 3b9 which are also shown in FIG. 1. Kabat positions 96 to 99 correspond to actual amino acid residue positions 98–101 as shown in FIG. 1 and in the sequence listing (SEQ ID NOs 1–5). The selected synthetic Fabs have been designated 3b1, 3b2, 3b3, 3b4, 3b6, 3b7, 3b8, and 3b9.

The amino acid residues indicated in Experiment B in FIG. 5 for amino acid residues 31 to 35 of CDR1 have been assigned SEQ ID NOs 26–33 as follows: Asn-Phe-Thr-Leu-Met (3b1, SEQ ID NO 26), Asn-Tyr-Thr-Ile-Met (3b2, SEQ ID NO 27), Asn-Phe-Thr-Val-His (3b3, SEQ ID NO 28), Asn-Tyr-Thr-Leu-Ile (3b4, SEQ ID NO 29), Asn-Phe-Ile-Ile-Met (3b6, SEQ ID NO 30), Asn-Phe-Ser-Ile-Met (3b7, SEQ ID NO 31), Asn-Tyr-Thr-Ile-Gln (3b8, SEQ ID NO 32) and Asn-Phe-Thr-Val-His (3b9, SEQ ID NO 33). The amino acid residues indicated in Experiment B in FIG. 5 for Kabat identified amino acid residues 96 to 99 of CDR3 have been assigned SEQ ID NOs 34–42 as follows: Pro-Tyr-Ser-Trp (MT4, SEQ ID NO 34), Gln-Trp-Asn-Trp (3b1, SEQ ID NO 35), Pro-Trp-Thr-Trp (3b2, SEQ ID NO 36), Glu-Trp-Gly-Trp (3b3, SEQ ID NO 37), Pro-Trp-Asn-Trp (3b4, SEQ ID NO 38), Leu-Trp-Asn-Trp (3b6, SEQ ID NO 39), Ser-Trp-Arg-Trp (3b7, SEQ ID NO 40), Pro-Tyr-Ser-Trp (3b8, SEQ ID NO 41), and Pro-Trp-Arg-Trp (3b9, SEQ ID NO 42).

Alignment of derived sequences with one another and with the Genbank database made use of the MacVector suite of programs. For analysis of heavy chain CDR3 sequences as described by Sanz, *J. Immunol.*, 147:1720–1729 (1991), the most 5' nucleotide was considered to be the first nucleotide after codon 95 of the H chain variable region according to Kabat et al, Sequences of Proteins of Immunological Interest, US Dept. of Health and Human Services, Washington, D.C. (1991).

In assessing the randomization of amino acid residue sequence in CDR3 following 6 rounds of selection for binding to IIIb-derived gp120, conservation of particular amino acid residues is also noted. Specifically, the amino acid residues randomized in MT4 Fab were Pro-Tyr-Ser-Trp as shown in FIG. 1 from the third to the sixth amino acid residue positions in MT4. This corresponds to amino acid residue position 98–101 in SEQ ID NO 1 (Kabat positions 96–99). The tryptophan residue remained unchanged throughout the randomization and selection procedures. In all four preferred CDR1- and CDR3-randomized Fabs, the tyrosine amino acid residue was replaced by a tryptophan, therein exhibiting selection pressures for the particular amino acid residue in this position. The derived amino acid residue sequence of 3b8 is identical to that of MT4 and may indicate some contamination in the CDR1- and CDR3-randomized library.

In order to assess what effect the randomized amino acid residue sequences in the heavy chain CDR1 and CDR3 had on the functional abilities of the soluble Fabs, both binding affinity studies and neutralization assays were performed as described in Example 1H. Four clones, 3b1, 3b3, 3b4, and 3b9, were chosen for further study. These four clones have a sequence relatedness to one another characterized by small changes in amino acid sequence and also display the most dramatic change in amino acid residue identity at positions 96 and 98.

H. Functional Characterization of qp120-Specific Fabs Having Randomized CDR1 and CDR3 Heavy Chain Domains 1) Binding Affinity Analysis The four selected Fabs, 3b1, 3b3, 3b4 and 3b9, having randomized amino acid residue sequences in the entire CDR1 and in four of the 18 amino acid residues of the CDR3, were used in binding affinity assays. Surface plasmon resonance assays were performed in a BIAcore binding affinity measurement apparatus (Pharmacia, Piscataway, N.J.) following manufacturer's instructions to determine whether the affinity of the randomized Fabs had improved binding affinities as compared to the original MT4 Fab from which the new Fabs were derived.

In the assay, the gp120 glycoprotein, isolated from both MN (AgMed, Cambridge, Mass.) and IIIb (American Bio-Technologies) strains of HIV-1 were coated onto gold chips. The four soluble Fabs listed above, including MT4, were then separately admixed with the gp120-coated gold chips and the binding of the Fabs to the ligand was measured in the BIAcore apparatus. As the mass of the gold chips increases due to the binding of the Fabs to the ligand, the refractive index of the chips increases indicating a coordinate increase in the increase of the mass. Measurements of the "on" rate are made in addition to the "off" rates, the latter of which occurs as the Fabs begin to dissociate from the ligand and the mass coordinately decreases, thereby allowing a measurement of the change of the refractive index. Briefly, the sensor chip was activated for immobilization with N-hydroxysuccinimide an N-ethyl-N'-(3-diethyl aminopropyl) carbodiimide. The proteins, MN-derived or IIIb-derived gp120, were coupled to the surface by injection of 50 ul of a 50 ug/ml sample. Excess activated esters were quenched with 15 ul ethanolamine, 1 M pH 8.5. Typically, 4000 resonance units were immobilized. Binding of Fab fragments to immobilized gp120 was studied by injection of Fab in a range of concentrations (0.5 to 10 ug/ml) at a flow rate of 5 ul/minute. The association was monitored as the increase in resonance units per unit time. Dissociation measurements were acquired following the end of the association phase but with a flow rate of 50 ul/minute. The binding surface was regenerated with HCl, 1M NaCl, pH 3 and remained active for 20–40 measurements. The association and dissociation rate constants, $k_{on}$ and $k_{off}$, were determined from a series of measurements as described in Barbas et al., *Gene*, in press, (1993); Altschuh et al., *Biochemistry*, 31:6298–6304 (1992); and Karlsson et al., *J. Immunol. Methods*, 145:229–240, (1991). Equilibrium association and dissociation constants were deduced from the rate constants.

Both the on and off measurements for all four randomized Fabs and MT4 were collected. From these measurements, the association constant, $K_a$, was determined by dividing the on constant ($K_{on}$ ($M^{-1}s^{-1}$)) with the off ($K_{off}$ ($s^{-1}$)) constant. The dissociation constant, $K_d$, can also be determined from these measurements and is expressed as $K_{off}/K_{on}$. The measurement for both the on and off values for gp120 isolated from both MN and IIIb strains are shown, respectively, in Tables 1 and 2 below. In addition, the calculated value of the $K_a$ and $K_d$ from the measurement of the binding affinity is shown for all the Fabs analyzed.

TABLE 1

(MN Strain)

| Fab | $K_{on}$ ($M^{-1}s^{-1}$) | $K_{off}$ ($S^{-1}$) | $K_a$ ($M^{-1}$) | $K_d$ (M) |
|---|---|---|---|---|
| 3b1 | $1.4 \times 10^5$ | $1.8 \times 10^{-3}$ | $7.8 \times 10^7$ | $1.3 \times 10^{-8}$ |
| 3b3 | $1.6 \times 10^5$ | $1.2 \times 10^{-3}$ | $1.3 \times 10^8$ | $7.5 \times 10^{-9}$ |
| 3b4 | $8.6 \times 10^4$ | $4.1 \times 10^{-3}$ | $2.1 \times 10^7$ | $4.8 \times 10^{-8}$ |
| 3b9 | $8.1 \times 10^4$ | $1.1 \times 10^{-3}$ | $7.4 \times 10^7$ | $1.4 \times 10^{-8}$ |
| MT4 | $3.4 \times 10^4$ | $1.5 \times 10^{-3}$ | $2.3 \times 10^7$ | $4.4 \times 10^{-8}$ |

TABLE 2

(IIIb Strain)

| Fab | $K_{on}$ ($M^{-1}s^{-1}$) | $K_{off}$ ($S^{-1}$) | $K_a$ ($M^{-1}$) | $K_d$ (M) |
|---|---|---|---|---|
| 3b1 | $8.5 \times 10^4$ | $1.1 \times 10^{-4}$ | $7.7 \times 10^8$ | $1.3 \times 10^{-9}$ |
| 3b3 | $8.4 \times 10^4$ | $6.5 \times 10^{-5}$ | $1.3 \times 10^9$ | $7.7 \times 10^{-10}$ |

TABLE 2-continued (IIIb Strain)

| Fab | $K_{on}$ (M$^{-1}$S$^{-1}$) | $K_{off}$ (S$^{-1}$) | $K_a$ (M$^{-1}$) | $K_d$ (M) |
|---|---|---|---|---|
| 3b4 | $7.7 \times 10^4$ | $3.6 \times 10^{-4}$ | $2.1 \times 10^8$ | $4.8 \times 10^{-9}$ |
| 3b9 | $4.5 \times 10^4$ | $1.8 \times 10^{-4}$ | $2.5 \times 10^8$ | $5.0 \times 10^{-9}$ |
| MT4 | $7.6 \times 10^4$ | $4.8 \times 10^{-4}$ | $1.6 \times 10^8$ | $6.3 \times 10^{-9}$ |

In analyzing the data in Table 1 and Table 2, respectively, the binding affinity analysis of the randomized Fabs to gp120 from MN and IIIb strains of HIV-1, the binding affinity of the randomized Fabs is enhanced as compared to the original gp120-specific Fab, MT4, from which the randomized Fabs were derived. Only one Fab, 3b4, did not exhibit an increase in $K_a$ in binding to gp120 from the MN strain as shown in Table 1. All other Fabs in binding to MN-derived gp120 had a three to ten-fold increase in binding affinity over that of MT4. All the randomized Fabs showed even greater affinity to the IIIb-derived gp120 as shown in Table 2. Fab 3b3 had a $K_a$ of ten-fold greater than MT4 as it did with the MN-derived gp120. However, the binding affinity of 3b3 to the MN versus the IIIb strain was also 10 fold higher, $1.3 \times 10^8$ versus $1.3 \times 10^9$, respectively.

Thus, not only did the Fabs having randomized CDR1 and CDR3 exhibit heightened binding affinity as compared to the original MT4 Fab, the binding affinities were further enhanced depending on the HIV-1 strain from which the gp120 ligand was derived. The randomization of the CDR1 and CDR3 amino acid residue sequences in the four Fabs, 3b1, 3b3, 3b4 and 3b9, therefore has resulted in a significant and unexpected augmentation of the binding affinity of the Fabs to gp120, from both MN and IIIb strains of HIV-1. This functional aspect is an important attribute for diagnostic and therapeutic uses in that heightened binding affinity in comparison to known gp120-specific antibodies, as well as other HIV-1 antibodies, will provide an enhancement to targeting and neutralizing functions as described below.

2) Neutralizing Activity of gp120-Specific Fabs Having Randomized CDR1 and CDR3

Binding of antibodies to viruses can result in loss of infectivity or neutralization and, although not the only defense mechanism against viruses, it is widely accepted that antibodies have an important role to play. However, understanding of the molecular principles underlying antibody neutralization is limited and lags behind that of the other effector functions of antibody. Such understanding is required for the rational design of vaccines and for the most effective use of passive antibody for prophylaxis or therapy. This is particularly urgent for the human immunodeficiency viruses.

A number of studies have led to the general conclusion that viruses are neutralized by more than one mechanism and the one employed will depend on factors such as the nature of the virus, the epitope recognized, the isotype of the antibody, the cell receptor used for viral entry and the virus:antibody ratio. The principle mechanisms of neutralization can be considered as aggregation of virions, inhibition of attachment of virus to cell receptor and inhibition of events following attachment such as fusion of viral and cellular membranes and secondary uncoating of the virion. One of the important features of the third mechanism is that it may require far less than the approximately stoichiometric amounts of antibody expected for the first two mechanisms since occupation of a small number of critical sites on the virion may be sufficient for neutralization. For instance it has been shown that neutralization of the influenza A virion obeys single hit kinetics as described by Outlaw et al., Epidemiol. Infect., 106:205–220 (1992).

Intensive studies have been carried out on antibody neutralization of HIV-1. For review, see Nara et al., FASEB J., 5:2437–2455 (1991). Most have focussed on a single linear epitope in the third hypervariable domain of the viral envelope glycoprotein gp120 known as the V3 loop. Antibodies to this loop are suggested to neutralize by inhibiting fusion of viral and cell membranes. Binding to the loop resulting in neutralization can occur prior to virus-cell interaction or following gp120 binding to CD4. See, Nara, In Retroviruses of Human Aids and Related Animal Diseases, eds. Girard et al., pp. 138–150 (1988); Linsely et al., J. Virol., 62:3695–3702 (1988); and Skinner et al., J. Virol., 67:4195–4200 (1988). Features of the V3 loop are sequence variability within the loop [Goudsmit et al., FASEB J., 5:2427–2436 (1991) and Albert et al., AIDS, 4:107–112 (1990)] and sensitivity of neutralizing antibodies against the loop to sequence variations outside the loop [Nara et al., FASEB J., 5:2437–2455 (1991); Albert et al., AIDS, 4:107–112 (1990); McKeating et al., AIDS, 3:777–784 (1989); and Wahlberg et al., AIDS Res. Hum. Retroviruses, 7:983–990 (1991). Hence anti-V3 loop antibodies are often strain specific and mutations in the loop in vivo may provide a mechanism for viral escape from antibody neutralization.

Recently considerable interest has focussed on antibodies capable of blocking CD4 binding to gp120. A number of groups have described the features of these antibodies as (a) reacting with conformational i.e., non-linear epitopes, (b) reacting with a wide range of virus isolates and (c) being the predominant neutralizing antibodies in humans after longer periods of infection. See, Berkower,et al., J. Virol., 65:5983–5990 (1991); Steimer et al., Science, 254:105–108 (1991); Ho et al., J. Virol., 65:489–493 (1991); Kang et al., Proc. Natl. Acad. Sci., USA, 88:6171–6175 (1991); Posner et al., J. Immunol., 146:4325–4332 (1991); and Tilley et al., Res. Virol., 142:247–259 (1991).

Neutralizing antibodies of this type would appear to present a promising target for potential therapeutics. The mechanism(s) of neutralization of these antibodies is unknown although there is some indication that this may not be blocking of virus attachment since a number of mouse monoclonal antibodies inhibiting CD4 binding to gp120 are either non-neutralizing or only weakly neutralizing.

The generation of human monoclonal antibodies against the envelope of HIV-1 as described by Burton et al., Proc. Natl. Acad. Sci., USA, 88:10134–10137 (1991) using combinatorial libraries allows a novel approach to the problem of neutralization. Given the lack of a three-dimensional structure for gp120 and the complexity of the virus, the approach of enhancing the functional activity of gp120-specific Fabs through randomization of the CDR in either the heavy chain, light chain or both, seeks to explore neutralization at the molecular level through the behavior of related antibodies. Neutralization studies were performed as described herein on the human recombinant Fabs prepared in Example 1F and analyzed for binding affinity to gp120, derived from either MN or IIIb strains as described above.

a) Neutralizing Activity of gp120 Specific Fabs Having Randomized CDR1 and CDR3 with MN-derived qp120

A syncytium assay, was performed to measure neutralization ability of the recombinant human HIV-1 immunoreactive Fabs. For some of these assays, the recombinant Fabs were first purified. One liter cultures of SB containing 50 ug/ml carbenicillin and 20 MM $MgCl_2$ were inoculated with appropriate clones and induced 7 hours later with 2 mM IPTG and grown overnight at 30 C. The cell pellets were sonicated and the resultant supernatant were concentrated to a 50 ml volume. The filtered supernatants were loaded on a 25 ml protein G-anti-Fab column, washed with 120 ml buffer at a rate of 3 ml/minute and eluted with citric acid at pH 2.3. The neutralized fractions were then concentrated and exchanged into 50 mM MES at pH 6.0 and loaded onto a 2 ml Mono-S column at a rate of 1 ml/minute. A gradient of 0–500 mM NaCl was run at 1 ml/minute with the Fab eluting in the range of 200–250 mM NaCl. After concentrating, the Fabs were positive when titered on ELISA against gp120 and gave a single band at 50 kD by 10–15% SDS-PAGE. Concentration was determined by absorbance measurement at 280 nm using an extinction coefficient (1 mg/ml) of 1.4.

A quantitative neutralization assay with the MN strain of HIV-1 was performed as described by Nara et al., *AIDS Res. Human Retroviruses,* 3:283–302 (1987), the disclosure of which is hereby incorporated by reference. Monolayers of CEM-SS target cells were cultured with virus, in the presence or absence of Fab antibody, 3b1, 3b3, 3b4, 3b9 and MT4, and the number of syncytia forming units determined 3–5 days later. An equivalent amount of virus was used in the assays to allow direct comparison of the various antibody concentrations tested. The assays were repeatable over a virus-surviving fraction range of 1 to 0.001 within a 2 to 4-fold difference in the concentration of antibody (P<0.001).

Assays were generally repeated at least twice with reproducible results. For the data reported in Table 3, the data is expressed as both $IC_{50}$ ($M^{-1}$) and as Neutralization Titer in nanograms/milliliter (ng/ml). The neutralization titer is calculated as $1/IC_{50} \times (5 \times 10^{10})$. The original gp120-specific Fab, originally selected from a bone marrow library from an HIV-1 seropositive individual, was previously characterized by Barbas et al., *J. Mol. Biol.,* 230:812–823 (1993) as having high binding affinity and equally effective neutralization ability in both syncytial formation and p24 assays. In the neutralization assays performed as described herein, the MT4 Fab exhibited a neutralization titer of approximately 300 ng/ml to inhibit the infectivity of HIV-1 into the cells as measured by the decrease in syncytium formation. In striking contrast, four randomized Fabs of this invention, 3b1, 3b3, 3b4 and 3b9, all having been derived from original clone pMT4-3, exhibited neutralization titers in this assay ranging from approximately 5 up to 20 ng/ml. This represents a significant improvement of greater than 10 fold increase in titer of the neutralizing ability of the randomized Fabs as compared to MT4, and antibody known to neutralize HIV-1 infection.

TABLE 3

| Fab | $IC_{50}$ ($M^{-1}$) | Neutralization Titer (ng/ml) |
| --- | --- | --- |
| 3b1 | 5.42 × 10⁹ | 9.2 |
| 3b3 | 9.02 × 10⁹ | 5.5 |
| 3b4 | 2.57 × 10⁹ | 19.4 |
| 3b9 | 6.4 × 10⁹ | 7.8 |
| MT4 | 1.69 × 10⁸ | 296.0 |

Figure 3:
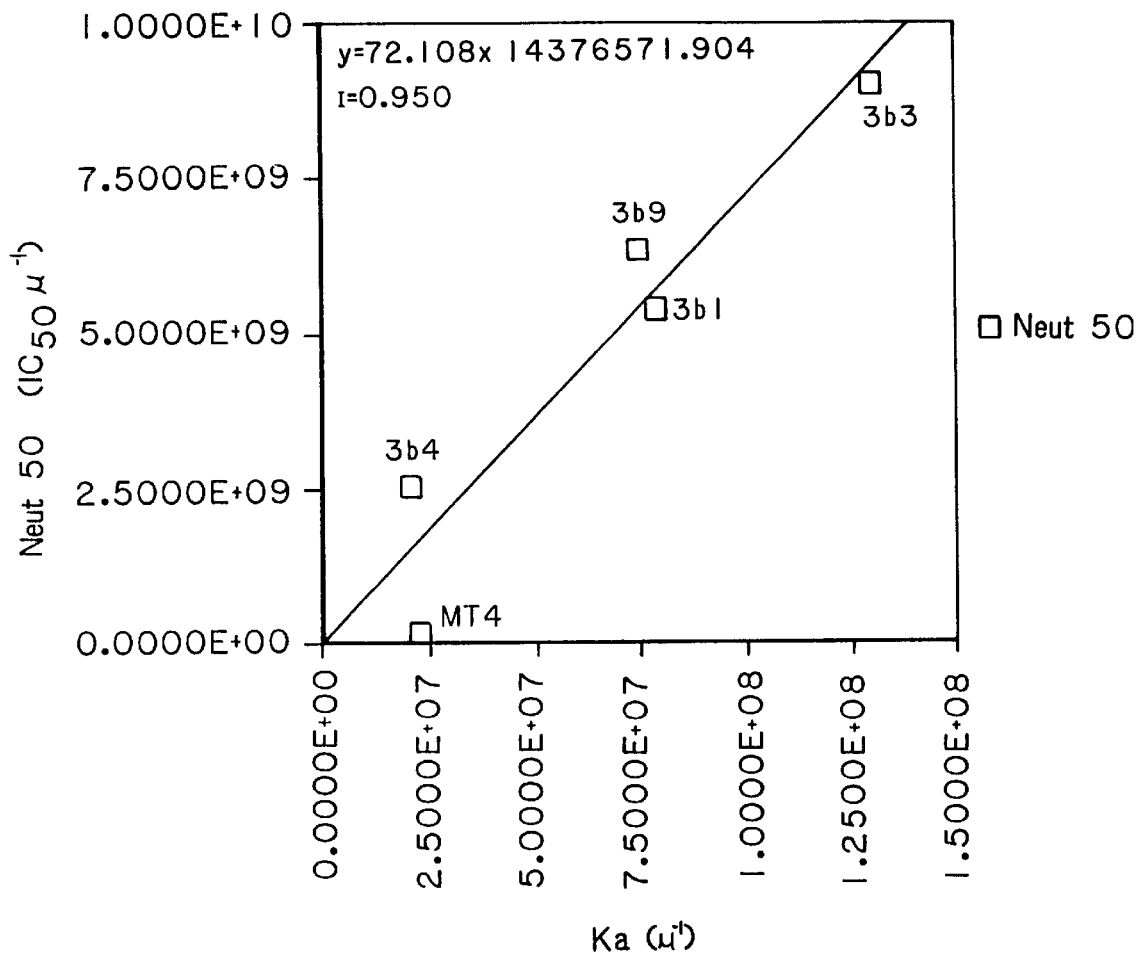
FIG. 3 is a graph that illustrates the correlation of the binding affinity and neutralization ability of the synthetic Fabs of this invention, 3b1, 3b3, 3b4 and 3b9, with gp120 from the MN strain of HIV-1. The binding affinity ($K_a$ $M^{-1}$) is plotted on the X-axis as indicated as an exponential value E+ and with the neutralization ability (Neut 50, $IC_{50}$ $M^{-1}$) plotted on the Y-axis. The $IC_{50}$ values, rather than the neutralization titer, are plotted for the neutralization data in the graph. The binding affinity data for generating the graph are presented in Table 1 in Example 1H under the column heading $K_a$ ($M^{-1}$). The neutralization data are presented in Table 3 in Example 1H under the column heading $IC_{50}$ ($M^{-1}$). The data for each Fab is indicated in the graph. The relationship between binding affinity and neutralization ability is relatively linear as described in Example 1H with Fab 3b3 exhibiting both the highest binding affinity and neutralization ability. All four synthetic Fabs of this invention having randomized CDR1 and CDR3 in the heavy chain exhibited enhanced binding affinity and neutralization ability over the original clone, MT4.

Thus, the methods of this invention in randomizing both the CDR1 and CDR3 of the heavy chain of a clone which originally was effective at binding to gp120 and neutralizing HIV-1 infection has resulted in the significant and unexpected improvement of Fabs that have heightened binding affinities as well as neutralization of infection capacities. Moreover, a correlation between the increase in binding affinity with the ability to inhibit HIV-1 infection of cells exists as graphically shown in FIG. 3. In that figure, the binding affinity of the randomized Fabs along with MT4 was plotted against the neutralization titer as shown by $IC_{50}$. Five separate squares are shown in the figure for each of the five Fabs plotted based on the two functional characterizations. A linear relationship is readily apparent in viewing the graph. Thus, there is a correlation of binding affinity to the ability to neutralize HIV-1 infection. Moreover, all four randomized Fabs of this invention, exhibited enhanced correlations as compared to MT4 as shown on the figure where the Fabs are shown in increasing linearity, with MT4 having the lowest binding affinity and neutralizing capacity, followed by 3b4, 3b9 and 3b1 (comparably similar), and lastly 3b3. The latter Fab bound to gp120, derived from either MN or IIIb strains, and had the lowest neutralization titer of all randomized Fabs of this invention. Thus, randomization of the CDR1 and three CDR3 amino acid residues, as the tryptophan in the sixth position in the latter was conserved throughout selection, resulted in the significant increase of both binding affinity and ability to neutralize HIV-1 infection compared to a non-randomized gp120-specific Fab.

b) Neutralizing Activity of gp-120 Specific Fabs Having Randomized CDR1 and CDR3 with IIIb-Derived gp120

A quantitative neutralization assay with the IIIb strain of HIV-1 was performed as described in Example H2a. For the results reported in Table 4, the data is expressed as both $IC_{50}$ (M) and as Neutralization Titer in nanograms/milliliter (ng/ml). The Neutralization Titer is calculated as $1/IC_{50} \times (5 \times 10^{10})$. The gp120-specific Fab MT4, originally selected from a bone marrow library from an HIV-1 seropositive individual, was previously characterized by Barbas et al., *J. Mol. Biol.,* 230:812–823 (1993), as having high binding affinity and equally effective neutralization ability in both syncytial formation and p24 assays. In the neutralization assays performed as described herein with gp120 from the IIIb strain of HIV-1, the MT4 Fab had a neutralization titer of approximately 39 ng/ml required to inhibit the infectivity of HIV-1 into the cells as measured by the decrease in syncytium formation. Four randomized Fabs of this invention, 3b1, 3b3, 3b4 and 3b9, all having been derived from original clone pMT4-3, had neutralization titers ranging from approximately 22 to 66 ng/ml. This represents a clustering of Fabs with similar potencies. With the gp120 from the IIIb strain of HIV-1, a range of reactivity of only 3-fold was noted with the most potent Fab, 3b1, showing a modest 2-fold increase in potency when compared to the original MT4 Fab.

TABLE 4

| Fab | $IC_{50}$ (M) | Neutralization titer (ng/ml) |
| --- | --- | --- |
| 3b1 | 4.4 × 10⁻¹⁰ | 22 |
| 3b3 | 9.4 × 10⁻¹⁰ | 47 |
| 3b4 | 9.9 × 10⁻¹⁰ | 50 |
| 3b9 | 1.3 × 10⁻⁹ | 66 |
| MT4 | 7.7 × 10⁻¹⁰ | 39 |

While the Fabs of this invention, 3b1, 3b3, 3b4 and 3b9, do not demonstrate the same striking increase in potency with IIIb as was demonstrated with MN, it should be noted that the MT4 Fab from which these Fabs were derived demonstrated a 10-fold greater potency with IIIb-derived gp120 than with MN-derived gp120.

The kinetics of binding of purified Fab to two types of gp120 were compared from the highly divergent isolates MN and IIIb. Myers et al., *Human Retroviruses and Aids* 1992, Theoretical Biology and Biophysics, Los Alamos, N.

Mex., (1992). A comparison of the recombinant protein MN-derived gp120 and IIIb-derived gp120 revealed 88 amino acid residue changes in the aligned sequences as well as 11 deletions and 5 insertions of amino acid residues. Infectivity of a target cell requires binding of the viral surface glycoprotein gp120 to the CD4 molecule on the surface of the target, therefore, the CD4 binding site on gp120 is a common target for anti-viral antibodies. Sun et al., *J. Virol.*, 63:3579–3585 (1989); Thali et al., *J. Virol.*, 65:6188–6193 (1991); Tilley et al., *Res. Virol.*, 142:247–259 (1991); Karwowska et al., *AIDS Res. Hum. Retroviruses,* 8:1099–1106 (1992); and Moore et al., *J. Virol.*, 67:863–875 (1993). However, antibodies to this region are not generally particularly potent in terms of virus neutralization. Furthermore, such antibodies tend to be even less potent against primary isolates of virus than the more commonly employed laboratory strains. Moore et al., *Perspectives in Drug Discovery and Design,* 1:235–250 (1993). Therefore, an HIV-1 neutralizing human antibody directed against the CD4-binding site of gp120 which demonstrates increased affinity, potency, and broadened strain reactivity would be highly desirable in prophylactic and therapeutic applications.

The Fabs of this invention demonstrate exceptional potency in the $10^{-9}$ range with both the gp120 derived from the MN and IIIb laboratory strains of HIV-1. The Fab 3b3 was selected for further study in neutralization assays with primary clinical ("field") isolates due to its 54-fold improvement in affinity to MN-derived gp120.

c) Neutralizing Activity of gp120-Specific Fab 3b3 Having a Randomized CDR1 and CDR3 with Primary Clinical HIV Isolates The key issue in producing antibodies to HIV-1 for therapeutic or prophylactic purposes is that they should be highly potent (of high affinity and neutralizing ability) and be cross reactive with a wide range of primary clinical (field) isolates. These are generally two opposing characteristics. The degree of antigenic relatedness between different patient isolates of HIV has been examined by cross-neutralization in a microplaque assay. Wrin et al., *J. of Acquired Immune Deficiency Syndromes,* 7:211–219, (1994). The cross-neutralization assays with heterologous sera and virus isolates from 11 individuals revealed variations in breadth of neutralization among individual sera and variation in the frequency of neutralization among the different primary clinical isolates.

A quantitative assay to measure the reduction of infectivity of primary clinical isolates of HIV-1 in the presence of the Fabs MT4 and 3b3 was determined in a microplaque assay as described in Hanson et al., *J. of Clin. Microb.,* 2030–2034 (1990). Primary clinical isolates of HIV-1 were isolated from frozen peripheral blood lymphocytes obtained from seropositive donors as described in Gallo et al., *J. of Clin. Microb.,* 1291–1294 (1987) and cultivated in peripheral blood mononuclear cells (PBMC). Briefly, HIV isolates were obtained by incubating frozen HIV-infected patient PBMCs with seronegative donor PBMCs in RPMI-1640 medium containing 20% heat-inactivated fetal bovine serum, 2 ug/ml polybrene, 5% interleukin-2, and 0.1 anti-human leukocyte interferon. The cultures were fed with fresh donor PBMCs once a week, and the supernatants were assayed for the presence of reverse transcriptase (RT) activity beginning at day 11. The cultures were considered positive if, for 2 consecutive weeks, the RT counts were >10-fold higher than those in the cultures of the seronegative donor PBMCs alone.

The resultant RT-positive virus isolates were tested for cytolysis in the MT2 (α-4 clone) (Hanson et al., *J. of Clin. Microb.,* 2030–2034, 1990), and the viruses which were found to cytolytic, a requirement for viruses usable in the subsequent MT2 microplaque assay system. Supernatant fluids from the primary PBMC isolation cultures were used to infect expanded cultures of phytohemagglutinin (PHA)-stimulated PBMCs from healthy seronegative blood donors. These infected PBMC cultures were grown in RPMI-1640 medium supplemented with 15% fetal bovine serum, 5% interleukin-2, 0.1% anti-α interferon, 2 ug/ml polybrene, 50 ug/ml gentamicin, 100 U/ml penicillin, and 100 ug/ml streptomycin. The crude supernatants were harvested after 7 days and frozen as viral stocks at −70° C.

The primary clinical isolates of HIV-1 used in this microplaque assay are designated VL135, VL263, VL596, VL069, VL434, VL114, VL172, VL530, and VL750. Isolates VL135, VL434, VL069, VL263, and VL596 have been previously described as isolates 1, 3, 4, 5, and 7, respectively, in Wrin et al., *J. of Acquired Immune Deficiency Syndromes,* 7:211–219 (1994).

The laboratory HIV-1 strains MN and IIIb as well as isolate VL069 were propagated in H9 cells as controls in the microplaque assay. Propagation of VL069 in H9 cells was performed to illustrate a host cell effect which results in a sensitization when isolates are propagated in H9 cells and has been previously described in Sawyer, et al., *J. Virol.,* 68:1342–1349 (1994).

The Fabs MT4 and 3b3 and a pool of human plasma from 13 HIV-1 seropositive patients (+PHP) were used as the source of neutralizing antibodies in a 96-well microtiter plaque reduction assay as described by Hanson et al., *J. of Clin. Microb.,* 2030–2034 (1990). Briefly, serial dilutions of the Fabs MT-4 or 3b3 (starting at 50 ug/ml and decreasing) or heat-inactivated pooled patients' plasma (starting at a 1:10 dilution and decreasing to 1:256) were combined with an equal volume containing 10–25 plaque-forming units (PFU) of HIV per well and incubated for 18 hours at 37 C. The diluent used for both virus and patient plasma dilutions contained 50% normal human serum pool (prepared by recalcification of human plasma) which had been heat inactivated at 56 C. for 60 minutes to remove complement. Negative control wells also contained 50% normal human serum pool with no patient immune serum. After the 18 hour incubation of Fabs or serum and virus, 90,000 MT2 cells were added per well and incubated at 37 C. for 1 hour. SeaPlaque Agarose in assay medium at 39.5 C. was then added to a final concentration of 1.6%. While the warm agarose was still molten, the microtiter plates were centrifuged at 20 C. for 20 minutes at 500×g to form cell monolayers. The plates were incubated for 5 days at 37 C. and then stained 18 to 24 hours with 50 ug/ml propidium iodide. The fluorescent plaques were counted with transillumination by a 304 nm ultraviolet light source using a low-power stereo zoom microscope. Inhibition of infectivity, or neutralization titer, is defined as the ug/ml of Fab or the plasma dilution giving 50% inhibition of plaque count as compared with controls. Within an experimental run, the intrinsic statistical error of the interpolated titers averages ±30%.

The inhibition of infectivity, or neutralization titer, for the Fabs MT4 and 3b3 and the pooled HIV seropositive human plasma from 13 donors (+PHP) is given in Table 5. The neutralization titer for each of the viral isolates is expressed as the minimum ug/ml of Fabs MT4 and 3b3 required for 50% inhibition of plaque count as compared to the controls. The neutralization titer for each of the viral isolates is expressed as the minimum titer of the pooled HIV seropositive human plasma from 13 donors (+PHP) required for 50% inhibition of plaque count as compared to the controls.

The Fab MT4 was able to neutralize only two of the nine primary clinical isolates assayed at concentrations of 50 ug/ml and less as measured as the ug/ml required for 50% inhibition of plaque count as compared to the controls. In contrast, the Fab 3b3 was able to neutralize six of the nine primary clinical isolates at concentrations of 50 ug/ml and less as measured as the ug/ml required for 50% inhibition of plaque count as compared to the controls. Thus, the highest affinity Fab, 3b3, was able to neutralize an additional four primary clinical isolates as compared to the Fab MT4 from which it was derived. Fifty-percent neutralization of isolates VL135 and VL530 by Fab 3b3 at 38.9 and 29.5 ug/ml, respectively, is significant because the Fab MT4, from which 3b3 was derived, showed insignificant levels of neutralization (about 10%) at 50 ug/ml. Neutralization of MN- and IIIb-derived gp120 was improved approximately 5-fold in the microplaque assay when compared to the previously performed syncytium formation assay described in Example 2H.

TABLE 5

Neutralization of Field Isolates of HIV

| | | ug/ml required for 50% neutralization | | Titer |
|---|---|---|---|---|
| Virus | Host Cell | MT-4 | 3b3 | +PHP |
| VL155 | PBMC | >50 | 38.9 | 1:33 |
| VL263 | PBMC | 17.0 | 6.6 | <1:10 |
| VL596 | PBMC | 33.1 | 17.0 | 1:10 |
| VL069 | PBMC | >50 | >50 | <1:10 |
| VL434 | PBMC | >50 | 10.5 | 1:10 |
| VL114 | PBMC | >50 | 5.2 | <1:10 |
| VL172 | PBMC | >50 | >50 | 1:10 |
| VL530 | PBMC | >50 | 29.5 | <1:10 |
| VL750 | PBMC | >50 | >50 | 1:10 |
| IIIb | H9 | 0.36 | 0.068 | 1:767 |
| MN | H9 | 0.18 | 0.044 | 1:24,000 |
| VL069 | H9 | 3.6 | 3.5 | 1:1,200 |

Thus, the methods of this invention in randomizing both the CDR1 and CDR3 of the heavy chain of an Fab clone which originally was effective at binding to gp120 and neutralizing HIV-1 infection has also resulted in the significant and unexpected improvement of Fabs that have broadened neutralization activities. This broadened neutralization activity was first demonstrated by an increase in binding affinities with the highly divergent HIV-1 gp120 isolates MN and IIIb. Selective pressure during the panning process could have been applied to favor cross-reactivity by selecting with a mixture of divergent gp120s, however, this did not prove to be necessary as Fabs with increased binding affinity to both MN and IIIb-derived gp120s were identified.

Potencies as judged by quantitative infectivity in neutralization assays with MN- and IIIb-derived gp120 stocks are improved as well. Affinity is well correlated with neutralizing ability with the MN-derived gp120. The potencies of the Fabs of this invention are equivalent to the potencies of soluble CD4 (sCD4). Layne et al., *Nature,* 346:277–279, (1990). This ability to neutralize with the potencies equivalent to sCD4 is unique.

The broadened neutralization activities of the Fabs of this invention were further demonstrated in quantitative neutralization assays with primary clinical isolates of HIV. The Fab 3b3, which demonstrated the highest affinity to MN-derived gp120, is able to neutralize an additional four primary clinical isolates as compared to the Fab MT4 from which it was derived. Characterization of these primary clinical isolates in neutralization assays revealed patterns of heterologous neutralization that suggested multiple phenotypes (Wrin et al., *J. of Acquired Immune Deficiency Syndromes,* 7:211–219, 1994). Thus, the randomization of CDR1 and CDR3 of the heavy chain of an Fab which effectively binds gp120 and neutralizes HIV-1 infection resulted in Fabs with broadened neutralization reactivity with primary clinical isolates of multiple phenotypes.

2. Preparation of Four Phagemid Libraries Having Randomized Heavy and Light Chain CDR and Selection of Affinity-Optimized Fabs Expressed Therefrom A. Overview of the Methods to Obtain Randomized Heavy and Light Chain gb120-Specific Fab Antibodies Mutagenesis of heavy chain CDR1 and CDR3 regions of pMT4-3 as described in Example 1 resulted in producing a phagemid, designated p3b3, for expressing the 3b3 heavy and light chain Fab heterodimer antibody which demonstrated an increase in affinity for gp120 with broadened neutralization reactivity with primary clinical isolates of multiple phenotypes.

The methods of producing higher affinity gp120-specific Fab antibodies of this invention, as described in Examples 2 and 3, are based on the CDR-directed random mutagenesis of either pMT4-3 or p3b3 obtained in Example 1. More particularly, preselected CDR were randomized in template DNA to optimize binding to the substrate gp120. Following the selective optimization, nucleotide fragments encoding mutagenized CDR from different gp120-reactive Fabs were then combined in particular combinations to form composite heavy and light chain domains that were subsequently inserted into an expression vector for the expression of soluble composite optimized CDR-containing Fabs having dissociation constants ($K_d$) of $10^{-10}$ M or greater.

The following general approach was used to obtain composite optimized CDR-containing Fabs having enhanced affinities: 1) New phagemid libraries were generated using the methods of this invention where each library resulted from amplification coupled with random mutagenesis of a particular CDR in preselected phagemid templates; 2) Following screening of the phagemid-Fab displayed libraries on gp120, particular clones were selected for preparation of additional libraries to obtain clones having multiple optimized CDR for conferring high affinity Fab antibody interaction with gp120; 3) Clones expressing preferred mutagenized Fabs were then used to create unique Fab-expressing clones having randomized and selected CDR1 and CDR3 heavy and light chains optimized for high affinity binding to gp120.

In producing and screening libraries as described in the overview above, the following libaries were prepared from which gp120-specific clones were selected for sequence and affinity analysis of expressed Fabs.

For one library, the pMT4-3 library having randomized heavy chain CDR1 (15 nucleotides) was subjected to a second round of screening as described in Example 1 in order to obtain additional gp120-specific clones expressing Fabs that are not glycosylated by having a histidine residue in the first position of CDR1 instead of a glycosylation-reactive asparagine residue as was obtained in the first screen in the clones encoding Fabs 3b1, 3b3, 3b4, and 3b9. The DNA encoding the selected Fabs was then inserted into the pPho-TT vector for the preparation of soluble Fabs for affinity and nucleotide sequence determination.

For a second library, the heavy chain CDR3 of phagemid 3b3 in pComb3H was also separately randomized over 15 nucleotides contiguous to the 12 nucleotides that were previously mutagenized in pMT4-3 for forming a phagemid expressing Fab 3b3 as described in Example 1. This extension of the mutagenized area in CDR3 was performed to obtain Fabs having affinities for gp120 equal to or greater than that obtained with Fab 3b3. Amplification products from the overlap PCR containing the newly randomized CDR3 were ligated back into 3b3 to form a randomized library having a randomized heavy chain CDR3 along with the previously randomized and selected heavy chain CDR1 and the nonmutagenized light chain originally derived from pMT4-3. Expression, selection and characterization were performed as described above.

For a third library, the light chain CDR1 of phagemid 3b3 in pComb3H was separately randomized over 18 nucleotides that encode six of the 12 amino acids in CDR1. The resultant amplification products having randomized light chain CDR1 were then ligated into 3b3 to form a 3b3-based light chain CDR1 mutagenized library. Thus, selected clones from this library contained the nucleotide sequences for expressing the original 3b3-mutagenized heavy chain CDR1 and CDR3 and the newly mutagenized light chain CDR1.

A fourth library in which a portion (15 nucleotides) of the light chain CDR3 were randomized was prepared as described for the third library above. The resultant 3b3-based library contained clones having nucleotide sequences for expressing the 3b3 mutagenized heavy chain CDR1 and CDR3 and the newly mutagenized light chain CDR3 with the original 3b3 light chain CDR1. Expression, selection and characterization were performed as described above.

To create gp120-binding synthetic Fabs having optimized light chain CDR1 and CDR3, a preferred clone, phagemid D, was selected from the fourth library having a randomized and selected light chain CDR1 and then was subjected to another round of mutagenesis on the light chain CDR3. For the resultant library, the expression and panning process was performed by two different methods, specific elution with acid versus competition with soluble Fab 3b3 followed by elution with acid. The latter elution procedure resulted in the isolation of clones encoding Fabs with both light- and heavy-chain mutagenized CDR1/CDR3 that exhibited a $K_d$ of $10^{-11}$ M or greater.

Individual light and heavy chain sequences having composite CDRs provided by separate identified and characterized Fab-expressing clones were prepared to eventually create unique Fabs having affinity optimized heavy and light chain variable domains compared to the clones from which the CDR were obtained.

One of skill in the art will appreciate that the above-enumerated steps can be performed in the order given or in a different order to prepare Fabs with mutagenized heavy and light chain CDR regions. The preparation of the aforementioned libraries and selection of gp120-specific Fabs therefrom are presented in detail below.

1) Preparation of pComb3H Expression Vector

The expression vector, pComb3H, is a modified version of the original pComb3 phagemid expression vector that was described in Example 1. As with pComb3, pComb3H also provides for the expression of phage-displayed bacteriophage coat protein 3-anchored proteins. Gene III of filamentous phage encodes the 406-residue minor phage coat protein, cpIII (cp3), which is expressed prior to extrusion in the phage assembly process on a bacterial membrane and accumulates on the inner membrane facing into the periplasm of E. coli. The nucleotide and amino acid residue sequences of gene 3 and the encoded coat protein, respectively, are familiar to one of ordinary skill in the art and have been published in International Application WO 92/18619, the disclosure of which is hereby incorporated by reference.

The modified vector, pComb3H, was designed to provide a human consensus sequence to the amino terminus of the heavy chain as described below. Furthermore, all homologous regions found in the original pComb3 were removed to increase the stability of the vector. The pComb3H vector from the lacZ promoter through the Not I restriction site is illustrated in FIG. 6 and the nucleotide sequence of the complete vector including the nucleotide sequences encoding the anti-tetanus toxin Fab, occupying the heavy and light chain cassettes, is listed in SEQ ID NO 43. The pComb3H vector containing the anti-tetanus toxin (TT) encoding sequences is designated pComb3H-TT. When the TT-encoding stuffers are removed from the pComb3H-TT vector, preselected heavy and light chain nucleotide sequences of this invention can be directionally inserted.

In using pComb3H, the first cistron encoding a periplasmic secretion signal (ompA leader) is operatively linked to a kappa light chain. The nucleotide sequence of the ompA, a leader sequence for directing the expressed protein to the periplasmic space, was as reported by Skerra et al., *Science*, 240:1038–1041 (1988). The second cistron encoded a pelB leader operatively linked to the fusion protein, Fd-cpIII. The presence of the pelB and ompA leaders facilitated the coordinated but separate secretion of both the fusion protein comprising the Fd/cp3 fusion protein and the kappa light chain from the bacterial cytoplasm into the periplasmic space.

Each chain was delivered to the periplasmic space by the pelB or ompA leader sequence, which was subsequently cleaved. The heavy chain was anchored in the membrane by the cp3 membrane anchor domain while the light chain was secreted into the periplasmic space. Fab molecules were formed from the binding of the anchored heavy chains with the soluble light chains.

The pComb3H vector was derived from the pComb3 vector and contains a lacZ promoter, ribosome binding site, ColE1 and f1 origins, and a beta-lactamase gene which were derived from pBluescript which has previously been described by Short et al., *Nuc. Acids Res.* 16:7583–7600 (1988). The complete nucleotide sequence of pBluescript has the GenBank Accession Number 52330. The DNA encoding amino acid residues 230 to 406 of cp3 was inserted following the Sfi I restriction site which is 3' of the Spe I restriction site (FIG. 6).

The pComb3H vector contains two Sfi I restriction sites (FIG. 6). One of the Sfi I sites is contained within the nucleotide sequence encoding the ompA leader which directs the secretion of the light chain and is therefore located 5' of the Sac I site. The second Sfi I site is between the Spe I site and the cp3 membrane anchor sequence. When the pComb3H vector contains DNA encoding a light chain and Fd, the two Sfi I sites are respectively located at the 5' end of the DNA sequence encoding the light chain and the 3' end of the DNA sequence encoding the Fd. Digestion of the pComb3H vector containing DNA encoding heavy and light chains with Sfi I removes a cassette comprising the DNA encoding the light chain, translational stop sequences, ribosomal binding site, pelB leader, and Fd. This cassette can then be directionally inserted into another expression vector, such as the pPho-TT vector, described in this invention. Therefore, in addition to the original restriction sites in pComb3, the addition of the Sfi I restriction sites is another modification to allow for subcloning of the entire heavy and light chain cassette in one fragment into an expression vector designated pPho for expression of soluble Fabs as described below.

Thus, the resultant combinatorial vector, pComb3H, consisted of a 3394 base pair DNA molecule having two cassettes to express one fusion protein, Fd/cp3, and one soluble protein, the light chain. The vector also contained nucleotide sequences for the following operatively linked elements listed in a 5' to 3' direction: a first cassette consisting of LacZ promoter/operator sequences; an Eco RI restriction site; a ribosome binding site; an ompA leader; a Sfi I restriction site; a spacer region; a cloning region bordered by 5' Sac I and 3' Xba I restriction sites; a Nco I restriction site located between the two cassettes; and a second cassette consisting of an expression control ribosome binding site; a pelB leader; a human consensus amino terminus spacer region encoding the amino acid residues Glu-Val-Gln-Leu-Leu-Glu (SEQ ID NO 44); a cloning region bordered by 5' Xho I and a 3' Spe I restriction sites followed by a Sfi I restriction site; the sequences encoding bacteriophage cp3 followed by a stop codon and a Nhe I restriction site; expression control stop sequences and a Not I restriction site.

The pComb3H vector sequence as given in SEQ ID NO 43, and designated pComb3H-TT, contains a light chain TT-encoding stuffer that is 1,200 bp in length and a heavy chain TT-encoding stuffer that is 300 bp in length. For cloning light chain variable domains for expressing Fabs of this invention, the light chain stuffer of an anti-tetanus toxin Fab light chain was removed by digestion with the restriction enzymes Sac I and Xba I prior to insertion of a similarly digested light chain. For cloning heavy chain variable domains for expressing Fabs of this invention, the heavy chain stuffer of an anti-tetanus toxin Fab heavy chain was removed by digestion with the restriction enzymes Xho I and Spe I prior to insertion of a similarly digested heavy chain.

The cassette containing DNA encoding the light chain sequences required for the expression of the heavy chain and DNA encoding the heavy chain were then removed from the pComb3H vector as described below and directionally inserted into the pPho-TT vector for the production of soluble Fab by digestion with the restriction enzyme Sfi I. Alternatively, the pComb3H vector can be digested with the restriction enzymes Nhe I and Spe I and religated to remove the cp3 membrane anchor sequence and express a soluble Fab.

1) Preparation of pComb3H Containing the Phagemid 3b3 Heavy and Light Chain Variable Domains In order to obtain CDR randomized expressed synthetic human Fab antibodies having both heavy and light chain variable domains, the heavy and light chain variable domain sequences of phagemid 3b3 were directionally ligated into pComb3H-TT by sequential replacement of each TT stuffer. This pComb3H-3b3 containing phagemid vector, designated pComb3H-3b3, was then used as a template for subsequent mutagenesis procedures. The randomization of 3b3-derived Fabs are described in Examples 2C through 2E.

For preparation of pComb3H-3b3, the phagemid 3b3 was first digested with Xho I and Spe I and the fragment was then ligated with a similarly digested pComb3H-TT vector to form a pComb3H vector containing the heavy chain variable domain of phagemid 3b3. To create a pComb3H phagemid for expressing both heavy and light chains derived from 3b3, the light chain cassette of 3b3, was digested with Sac I and Xba I and then inserted into the pComb3H-TT vector containing the 3b3 heavy chain that was similarly digested. In other words, a pComb3H-based vector containing the nucleotide sequence encoding the 3b3 mutagenized heavy chain variable domain and the nucleotide sequence encoding the 3b3-derived light chain variable domain respectively replaced the heavy and light chain anti-tetanus toxin stuffers in pComb3H-TT. The 3b3 light chain variable domain nucleotide sequence is the same as that of pMT4-3 as shown in FIG. 10 and in SEQ ID NO 62.

Following expression, the library of pComb3H-phage-anchored Fabs was screened by panning as previously described.

B. Preparation of Randomized CDR1 of the Heavy Chain Variable Domain of Phagemid pMT4-3

The CDR1 of the heavy chain variable domain in pMT4-3 was mutagenized as described in Example 1 and by Barbas et al., *Proc. Natl. Acad. Sci., USA*, 91:3809–3813115 (1994), the disclosure of which is hereby incorporated by reference. However, all of the screened and selected gp120-specific Fabs contained an asparagine (N) residue in the first position of CDR1. This is not a preferred residue as it serves as a glycosylation site. Therefore, to obtain additional Fabs having a preferred histidine (H) residue in that location, a second round of screening was performed on the heavy chain CDR1 in pMT4-3 as described in Example 1. The nucleotide sequences encoding resultant gp120-reactive phage-displayed Fabs were then subcloned into a pPho-TT vector as described below.

2) Amino Acid Residue Sequence Analysis of pMT4-3 Derived Fabs Having a Randomized Heavy Chain CDR1

Nucleic acid sequencing of the CDR1 randomized clones produced above was performed on six randomly chosen double-stranded Fab-expressing DNA clones using Sequenase 1.0 (USB, Cleveland, Ohio). Nucleic acid sequencing can be performed using any of the Fab-expressing vectors described in this invention as a template and is not dependent on whether the vector-driven Fab expression is soluble or membrane anchored. The alignment of derived amino acid residue sequences with one another and with the Genbank database made use of the MacVector suite of programs. The derived heavy chain amino acid residue sequences of six selected specific synthetic gp120-specific Fabs and MT4 are shown in FIG. 7. The alignment of the framework (FR) and complementarity determining regions (CDR) in the variable heavy chain domain as shown in FIG. 7 reveals that the original MT4 gp120-specific Fab obtained from screening a bone marrow library from an asymptomatic HIV-1 seropositive individual the amino acid residue sequence of CDR1 was Asn-Phe-Val-Ile-His (SEQ ID NO 1, from residues 28–32). Sequence comparisons indicated a preference for either asparagine (N) or histidine (H) at position 31, an aromatic residue at position 32, primarily threonine (T) at position 33, either isoleucine (I) or leucine (L) at position 34, and hydrophobic and/or aromatic residues at position 35.

The six amino acid residues indicated in FIG. 7 for CDR1 have the randomized and selected amino acid residue sequences from positions 28–32 in each of the SEQ ID NOs indicated: H4H1-1: His-Phe-Thr-Val-His (SEQ ID NO 45); H4H1-3: His-Phe-Thr-Leu-His (SEQ ID NO 46); H4H1-5: His-Phe-Thr-Ile-Met (SEQ ID NO 47); H4H1-6: Asn-Tyr-Thr-Leu-Gln (SEQ ID NO 48); H4H1-7: Asn-Phe-Thr-Leu-Ile (SEQ ID NO 49); and H4H1-8: Asn-Trp-Thr-Ile-Met (SEQ ID NO 50). As shown in FIG. 7, three of the six screened and selected heavy chain CDR1-mutagenized Fabs contained the preferred histidine residue as the first residue in CDR1 to avoid glycosylation as occurs if asparagine was present as was the case in MT4.

The DNA encoding the CDR1-mutagenized heavy chain Fabs selected for binding to gp120 were then separately transferred to the vector pPho-TT for expression of soluble Fabs. The soluble Fabs were then analyzed for binding affinity to gp120.

2) Binding Affinity Analysis of gb120-Specific Fabs Having Randomized Heavy Chain CDR1

The DNA that encoded Fabs containing a randomized heavy chain CDR1 which had been selected for binding to gp120 was then transferred to the vector pPho-TT for expression of soluble Fab. Affinity analysis of the binding of soluble Fabs was then performed as described below. The transfer of the nucleotide sequences encoding the gp120-specific Fabs coding regions for this purpose was facilitated by the presence of Sfi I restriction sites flanking the Fab coding regions in both the pComb3H-TT and pPho-TT vectors.

a) Preparation of pPho-TT Containing gb20-Specific Fabs

The expression vector, pPho-TT, is a modified version of the pComb3 and pComb3H phagemid expression vectors that were respectively described in Examples 1 and 2A. The pComb3 and pComb3H-TT vectors provided for the expression of soluble Fabs by the removal of the phagemid gene 3 anchor sequence encoding cp3 from the expression vector as described in Example 1G. As with the pComb3 and pComb3H vectors, pPho-TT also provides for the expression of soluble Fabs which are secreted to the periplasmic space. However, while expression of soluble Fabs from the pComb3 and pComb3H-TT vectors is regulated by the lacZ promoter, the expression of soluble Fabs from the pPho-TT vector is regulated by the alkaline phosphatase (phoA) promoter. As is well known to those of ordinary skill in the art, the phoA promoter is inducible under phosphate starvation conditions (Sambrook et al., in "Molecular Cloning: a Laboratory Manual", 2nd edition, Cold Spring Harbor Laboratory Press (1989)).

The pPho-TT vector is identical to the pComb3H-TT vector from the Eco RI site to the second Sfi I site, following the Spe I site. This region of pComb3H-TT is illustrated in FIG. 6. The nucleotide sequence of pPho-TT, the complete pPho vector including nucleotide sequences encoding an anti-tetanus toxin Fab which occupy the heavy and light chain cassettes, is listed in SEQ ID NO 51.

In using pPho-TT, the first cistron is identical to that encoded by the pComb3H-TT first cistron and provides for the expression and secretion of a kappa light chain. The second cistron encoded a pelB leader operatively linked to the heavy chain protein, Fd. The presence of the ompA and pelB leaders facilitated the coordinated but separate secretion of both the kappa light chain and Fd, respectively, from the bacterial cytoplasm into the periplasmic space.

The Fd and kappa light chains were secreted to the periplasmic space by their respective leader sequences which were then cleaved. Fab molecules were formed form the binding of the secreted Fd and kappa light chains.

The pPho-TT vector, a schematic restriction map of which is shown in FIG. 8, also contained a ribosome binding site, ColE1 and f1 origins, and a beta-lactamase gene as described for the pComb3H vector in Example 2B1a). The pPho-TT vector contained Xho I and Spe I sites for the directional insertion of DNA encoding a heavy chain and Sac I and Xba I sites for the directional insertion of DNA encoding a light chain. In addition, the pPho vector contained two Sfi I sites, identical to those of the pComb3H vector to facilitate the transfer of the entire heavy and light chain cassette in one fragment from the pComb3H vector into the pPho vector for the expression of soluble Fabs as herein described. Thus, the sites in the pPho vector allowed for the directional insertion of DNA encoding the heavy or light chain in two separate steps or for the directional insertion of a single cassette comprising DNA encoding both the heavy and light chain in a single step. When the DNA encoding the heavy or light chain is inserted into the pPho-TT vector in separate steps, the source of the inserted DNA can be from the same or different Fabs. In addition, a portion of either the heavy or light chain DNA-encoding sequence can be inserted into the pPho vector as described further herein.

Thus, the pPho-TT vector consisted of a DNA molecule having two cassettes to express two soluble proteins, a heavy chain (Fd) and a light chain. The vector contained nucleotide residue sequences for the following operatively linked elements listed in a 5' to 3' direction: a first cassette consisting of the phoA promoter/operator sequences; an Eco RI restriction site; a ribosome binding site; an ompA leader; a Sfi I restriction site; a spacer region; a cloning region bordered by 5' Sac I and 3' Xba I restriction sites; a Nco I restriction site located between the two cassettes and a second cassette consisting of an expression control ribosome binding site; a pelB leader; a human consensus amino terminus spacer region encoding the amino acid residues Glu-Val-Gln-Leu-Leu-Glu (SEQ ID NO 44); a cloning region bordered by 5' Xho I and 3' Spe I restriction sites followed by a Sfi I site; expression control stop sequences, and a Not I restriction site.

The pPho-TT vector sequence, as given in SEQ ID NO 51, contains a light chain stuffer that is 1,200 bp in length and a heavy chain stuffer that is 300 bp in length. The nucleotide sequences of the heavy and light chain stuffers encoded the heavy and light chain variable domains of a tetanus toxin (TT)-specific Fab, respectively. Thus the pPho vector sequence containing the light and heavy chain stuffers as given in SEQ ID NO 51 is designated, pPho-TT. For the insertion of heavy or light chain variable domains for the expression of Fabs of this invention, the heavy and light chain stuffers of pPho-TT were removed as described in Example 2B1a) for the preparation of the pComb3H-TT vector for expression of Fabs of this invention.

To prepare soluble heterodimers from pComb3H vectors as described in Examples 2C–2E, phagemid DNA encoding gp120-reactive clones was first isolated and then digested with Sfi I. pPho-TT was similarly digested. Digestion of the phagemid DNA and pPho-TT with the Sfi I restriction enzyme produced compatible cohesive ends. The 1.6-kb DNA fragment comprising the gp-120-reactive heavy and light chains and the 4.7-kb DNA fragment comprising the pPho vector were gel-purified (0.6% agarose) and ligated together. Transformation of E. coli DH10B (BioRad, Richmond, Calif.) afforded the isolation of recombinants comprising DNA encoding the gp120-reactive heavy and light chains and the pPho expression vector. Clones were examined for insertion of the heavy and light chain-encoding DNA fragment by Xho I-Xba I digestion, which should yield an 1.6-kb fragment. Thus, the DNA-encoding gp120-reactive heavy and light chains was transferred from the pComb3H to the pPho vector for the expression of soluble Fabs.

To prepare soluble heterodimers from pComb3-based vectors as described in Example 2B for vectors having a CDR1-randomized heavy chain, the heavy and light chain cassettes were separately isolated by digestion with Xho I/Spe I and Sac I/Xba I, respectively, and then sequentially directionally ligated into a similarly digested pPho-TT thereby sequentially replacing the TT heavy and light chain stuffer fragments.

b) Expression and Purification of Soluble gp120-Specific Fabs from pPho Expression Vectors For the expression and purification of gp120-specific soluble Fabs, clones were grown in low-phosphate medium to induce the phoA promoter as is well known in the art and described in Sambrook et al., in "Molecular Cloning: a Laboratory Manual", 2nd edition, Cold Spring Harbor Laboratory Press (1989)) and soluble Fabs purified as described in Example 1H2a).

c) Binding Affinity Analysis Using Plasmon Resonance

The second screened group of heavy chain CDR1-mutagenized Fabs selected by panning against gp120 as described in Example 2B2) were expressed in soluble form from pPho as described above for use in affinity determinations with laboratory isolates of gp120. Surface plasmon resonance was performed as described in Example 1H to determine the affinity of the selected Fabs having the preferred histidine residue in the first position of heavy chain CDR1.

The results of the Fab binding affinity analysis as measured by the equilibrium dissociation constant ($K_d$, M) of those Fabs having the preferred histidine residue (H4H1-1, H4H1-3 and H4H1-5) to gp120 strain IIIb are listed in Table 6. All measurements in the subsequent tables are presented as $K_d$, M. In addition, fold increases of affinity are calculated to provide a comparison of the effect on affinity of mutagenizing preselected heavy or light chain CDR with that of the nonmutagenized Fab MT4 obtained from a patient. The fold increases are calculated by dividing the measured $K_d$ ($6.3 \times 10^{-9}$ M) of the Fab MT4 with each of the measured $K_d$ of each new Fab having mutagenized CDR.

TABLE 6

| Fab | [1]$K_d$ | [2]Fold Increase of Mutant $K_d$ Compared to MT4 $K_d$ |
|---|---|---|
| H4H1-1 | $1.7 \times 10^{-9}$ | 3.7 |
| H4H1-3 | $2.0 \times 10^{-9}$ | 3.15 |
| H4H1-5 | $2.45 \times 10^{-9}$ | 2.57 |
| H4H1-6 | [3]ND | ND |
| H4H1-7 | ND | ND |
| H4H1-8 | ND | ND |

[1]Dissociation constants of mutants' binding to gp 120 (IIIB strain).
[2]Fold increase calculated by dividing the $K_d$ of MT4 ($6.3 \times 10^{-9}$) with the $K_d$ of each mutant.
[3]ND = not determined As evident from Table 6, the $K_d$ of the derived Fabs were in the range of $10^{-9}$ M and each exhibited an increase of gp120 IIIB strain binding affinity from 2–3 fold over that of the original Fab MT4. From each of the pPho vectors containing the nucleotide sequences encoding the H4H1 series Fabs, the nucleotide sequences encoding the histidine-containing heavy chain CDR1 were then separately isolated by a Xho I/Sac II digest and used as described in Example 3 (Table 11) to prepare separate composite heavy chains having the preferred CDR1 in combination with affinity optimized CDR3 prepared as described in C below.

C. Preparation of Randomized CDR3 Contiguous to the Previously Randomized Amino Acids in the Heavy Chain Variable Domain of Phagemid pComb3H-3b3

In order to further enhance the gp120 binding affinity of Fab 3b3 having a randomized heavy chain CDR1 and CDR3 prepared by overlap PCR as described in Example 1, 15 additional preselected nucleotides in the heavy chain CDR3 of p3b3 subcloned into pComb3H as described in Example 1A were subjected to mutagenesis by overlap PCR. To obtain Fab 3b3 as described in Example 1 from pMT4-3, 12 nucleotides encoding four amino acids, located at the third to the sixth amino acid residue position, in heavy chain CDR3 were randomized. The 15 contiguous nucleotides which were 3' to the first randomized 12 nucleotides were then mutagenized in pComb3H-3b3 to encode five new amino acid residues from the seventh to the eleventh CDR3 residues as shown in FIG. 9. As a result, Fabs selected from this new library as described below contained a total of nine randomized amino acid residues of the 18 amino acid residues in the CDR3 of the Fab 3b3 heavy chain, five newly randomized and selected amino acids combined with the four previously mutagenized and selected amino acids in Fab 3b3.

Thus, in essence, since Fab 3b3 was derived originally from pMT4-3, nine amino acid mutations were created by overlap PCR into the heavy chain CDR3 of Fab MT4.

As described in Example 1B, overlap PCR was similarly performed on the pComb3H-3b3 expression vector template previously obtained. In the first round of PCR, the 5' FTX3 oligonucleotide primer (SEQ ID NO 9) was used with 3' noncoding mutagenizing oligonucleotide primer, 3b3C35ob, having the nucleotide sequence 5'-CCAGACGTCCATATAATAATTGTCMNNMNNMNN-MNNMNNCCAACCCCACTCCCCCACTCT-3' (SEQ ID NO 52) to amplify heavy chain CDR3 and mutagenize the above-described 15 nucleotide region. The resultant amplified products were then purified as described in Example 1B and used in overlap PCR with the products from the second round.

The latter round of PCR was performed also as previously described in Example 1B but with the 5' coding overlapping oligonucleotide primer, h4h3of, having the nucleotide sequence 5'-GACAATTATTATATGGACGTCTGG-3' (SEQ ID NO 53) and the 3' noncoding oligonucleotide primer R3B (SEQ ID NO 12). The resultant amplified products were then purified as described in Example 1B and used in overlap PCR with the products from the first round using the oligonucleotide primer pair FTX3 and R3B to form a population of amplified heavy chain variable domains having newly mutagenized CDR3.

The heavy chain CDR3-randomized amplification products were then ligated into pComb3H-TT into which the Sac I/Xba I digested pMT4-3 light chain variable domain nucleotide sequence (same as p3b3's) was ligated as described in Example 2B to form a library of p3b3-derived pComb3H-CDR3 randomized expression vectors. Phage-displayed Fabs, each having a mutagenized heavy chain and the pMT4-derived light chain, were then expressed and panned on gp120 as described in Example 1.

1) Amino Acid Residue Sequence Analysis of p3b3 Derived Fabs Having a Randomized Heavy Chain CDR3

Clones encoding phage-displayed Fabs that specifically bound to gp120 were then sequenced and the derived amino acid residue sequences were analyzed as previously described. Nucleic acid sequencing of the CDR3 randomized clones produced above was performed on eight randomly chosen double-stranded Fab-expressing DNA clones using Sequenase 1.0 (USB, Cleveland, Ohio). Alignment of derived amino acid residue sequences with one another and with the Genbank database made use of the MacVector suite of programs. The derived heavy chain amino acid residue sequences of eight selected specific synthetic gp120-specific M556 series Fabs and 3b3 are shown in FIG. 9.

All selected M556 Fabs contained both the previously Fab 3b3-mutagenized and selected CDR1 (NFTVH—SEQ ID NO 3 from residues 28 to 32) and CDR3 (EWGW—SEQ ID NO 3 from residues 98–101). Each M556 Fab is unique, as indicated by the numbers following the M556 series designation, by having mutagenized and selected amino acid sequences in CDR3 corresponding to amino acid residue positions from 102 to 106. The complete heavy chain variable domain amino acid residue sequences of the M556 series are listed in the Sequence Listing as indicated in FIG. 9 by the assigned Sequence Listing identifiers.

2) Binding Affinity Analysis of gp120-Specific Fabs Having Randomized Heavy Chain CDR3

The DNA encoding the CDR3-mutagenized heavy chain M556 series Fabs selected for binding to gp120 obtained above were then transferred to the vector pPho-TT for expression of soluble Fabs as previously described. The soluble M556 series Fabs were then analyzed for binding affinity to gp120 (strain IIIB). Surface plasmon resonance was performed as described in Example 1H to determine the affinity of the selected Fabs.

The results of the Fab binding affinity analysis as measured by the equilibrium dissociation constant ($K_d$, M) of the M556 series Fabs are listed in Table 7. In addition, fold increases of affinity are also calculated as previously described.

TABLE 7

| Fab | [1]$K_d$ | [2]Fold Increase of Mutant $K_d$ Compared to MT4 $K_d$ |
|---|---|---|
| M556-2 | $4.39 \times 10^{-10}$ | 14.3 |
| M556-3 | $1.01 \times 10^{-10}$ | 63.0 |
| M556-7 | $1.31 \times 10^{-10}$ | 48.1 |
| M556-10 | $9.06 \times 10^{-11}$ | 69.5 |
| M556-15 | $1.74 \times 10^{-10}$ | 36.2 |
| M556-16 | $1.39 \times 10^{-10}$ | 45.3 |
| M556-5 | $1.81 \times 10^{-9}$ | 3.5 |
| M556-13 | $1.01 \times 10^{-9}$ | 6.2 |

[1]Dissociation constants of mutants' binding to gp 120 (IIIB strain).
[2]Fold increase calculated by dividing the $K_d$ of MT4 ($6.3 \times 10^{-9}$) with the $K_d$ of each mutant.

As evident from Table 7, six of the eight M556 series Fabs exhibited enhanced affinities as measured by $K_d$ of binding to gp120 IIIB strain in the range of $10^{-10}$ M to $10^{-11}$ M. Only two, M556-5 and M556-13, had affinities in the $10^{-9}$ M range. The fold increases of the M556 Fabs having $10^{-10}$ M or greater affinities ranged from 14 for M556-2 to 63 for M556-3, and 70 for M556-10, over that of original Fab MT4. The nucleotide sequences encoding the heavy chain CDR3 from these derived M556 Fabs were then separately isolated by a Sac II/Spe I digests from the pPho vectors and used as described in Example 3 (Table 11) to prepare separate composite heavy chains having the preferred CDR1 prepared above in combination with the M556 series affinity optimized heavy chain CDR3.

D. Preparation of Randomized CDR1 in the Kappa Light Chain Variable Domain of Phagemid pComb3H-3b3 (the pMT4-3 Original Light Chain)

In order to further enhance the gp120 binding affinity of Fab 3b3 having a randomized heavy chain CDR1 and CDR3 prepared by overlap PCR as described in Example 1, 15 preselected nucleotides in the light chain CDR1 of 3b3 in pComb3H-3b3 were subjected to mutagenesis by overlap PCR. The 3b3 nucleotide sequence having a CDR1 and CDR3 mutagenized heavy chain as prepared in Example 1 was subjected to overlap PCR to randomize 18 nucleotides from position 76 to 93 in the pComb3H-3b3 light chain variable domain as shown in FIG. 10 and listed as SEQ ID NO 62. Since the p3b3 sequence was derived from pMT4-3 without mutagenizing the light chain, the reference to the unmutagenized 3b3 light chain in pComb3H is the same as that to the light chain of pMT4-3. By randomizing the aforementioned 18 nucleotides, the encoded randomized amino acid residues are in CDR1 from positions 26 to 31 of the complete CDR1 from positions 22 to 33 as shown on FIG. 11 described below.

As a result of the light chain CDR1 mutagenesis of 3b3 in pComb3H-3b3, Fabs selected from this new library as described below contained a total of six randomized amino acid residues of the 12 amino acid residues in the Fab 3b3 light chain CDR1 and had the Fab 3b3 CDR1 and CDR3 mutagenized and selected heavy chain.

As described in Example 1B, overlap PCR was similarly performed on the pComb3H-3b3 expression vector template previously obtained. In the first round of PCR, the 5' oligonucleotide primer, KEF, having the nucleotide sequence 5'-GAATTCTAAACTAGCTAGTCG-3' (SEQ ID NO 63) was used with 3' noncoding mutagenizing oligonucleotide primer, HIV4cdr1-ov-b, having the nucleotide sequence 5'-AGGTTTGTGCTGGTACCAGGCTACMNNMNNMN-NMNNMNNMNNGTGACTGGACCTACAGGAGAAG-GT-3' (SEQ ID NO 64) to amplify the light chain CDR1 and mutagenize the above-described 18 nucleotide region. The resultant amplified products were then purified as described in Example 1B and used in overlap PCR with the products from the second round.

The latter round of PCR was performed also as previously described in Example 1B but with the 5' coding overlapping oligonucleotide primer, HIV4cdr1-fo, having the nucleotide sequence 5'-GTAGCCTGGTACCAGCACAAACCT-3' (SEQ ID NO 65) and the 3' noncoding oligonucleotide primer, T7B, having the nucleotide sequence 5'-AATACGACTCACTATAGGGCG-3' (SEQ ID NO 66). The resultant amplified products were then purified as described in Example 1B and used in overlap PCR with the products from the first round using the oligonucleotide primer pair KEF and T7B to form a population of amplified light chain variable domains having newly mutagenized CDR1.

The light chain CDR1-randomized amplification products were then ligated into pComb3H-TT into which the p3b3 heavy chain variable domain nucleotide sequence encoding the amino acid residue sequence shown in SEQ ID NO 3 was ligated as described in Example 2B to form a library of p3b3-derived pComb3H-CDR1 light chain randomized expression vectors. Phage-displayed Fabs, each having a mutagenized light chain and the p3b3-derived heavy chain, were then expressed and panned on gp120 as described in Example 1.

1) Amino Acid Residue Sequence Analysis of p3b3 Derived Fabs Having a Randomized Light Chain CDR1

Clones encoding phage-displayed Fabs that specifically bound to gp120 were then sequenced and the derived amino acid residue sequences were analyzed as previously described. Nucleic acid sequencing of the CDR1 randomized clones produced above was performed on four randomly chosen double-stranded Fab-expressing DNA clones using Sequenase 1.0 (USB, Cleveland, Ohio). The derived light chain amino acid residue sequences of the four selected specific synthetic gp120-specific A–D series of Fabs and 3b3 are shown in FIG. 11.

All selected A–D Fabs contained the p3b3-derived heavy chain variable domain. Each A–D Fab is unique by having mutagenized and selected amino acid sequences in the light chain CDR1 corresponding to amino acid residue positions from 26 to 31, within the complete CDR1 from amino acid residue positions 22 to 33 as listed in SEQ ID NOs 67–70. The complete light chain variable domain amino acid residue sequences of the A-D series are listed in the Sequence Listing as indicated in FIG. 11 by the assigned Sequence Listing identifiers.

2) Binding Affinity Analysis of gp120-Specific Fabs Having Randomized Light Chain CDR1

The DNA encoding the CDR1 mutagenized light chain A–D series Fabs selected for binding to gp120 obtained above were then transferred to the vector pPho-TT for expression of soluble Fabs as previously described. The soluble A–D series Fabs were then analyzed for binding affinity to gp120 strain IIIB. Surface plasmon resonance was performed as described in Example 1H to determine the affinity of the selected Fabs.

The results of the Fab binding affinity analysis as measured by the equilibrium dissociation constant ($K_d$, M) of the A–D series Fabs are listed in Table 8. In addition, fold increases of affinity are also calculated as previously described.

TABLE 8

| Fab | $^1K_d$ | $^2$Fold Increase of Mutant $K_d$ Compared to MT4 $K_d$ |
|---|---|---|
| A | $4.7 \times 10^{-9}$ | 1.30 |
| B | $1.1 \times 10^{-9}$ | 5.70 |
| C | $6.8 \times 10^{-10}$ | 9.26 |
| D | $2.2 \times 10^{-10}$ | 28.60 |

$^1$Dissociation constants of mutants' binding to gp 120 (IIIB strain).
$^2$Fold increase calculated by dividing the $K_d$ of MT4 ($6.3 \times 10^{-9}$) with the $K_d$ of each mutant.

As evident from Table 8, two Fabs, Fab C and Fab D, of the four A–D series Fabs exhibited enhanced affinities as measured by $K_d$ of binding to gp120 IIIB strain in the range of $10^{-10}$ M. Fabs A and B had affinities in the $10^{-9}$ M range. The fold increases of Fab C and Fab D were respectively approximately 9 and 28 fold over that of original Fab MT4 from which Fab 3b3 was derived. The fold increase as compared to the Fab 3b3 template from which Fabs A–D were derived can also be similarly calculated by using the $K_d$ of Fab 3b3 which is $7.7 \times 10^{-10}$ M.

The nucleotide sequences encoding the light chain variable domains from these derived CDR1-mutagenized Fabs were then separately used as templates for further mutagenesis procedures as described in Example 3. In addition, the nucleotide sequences encoding the light chain CDR1 of the Fabs A–D obtained herein were separately isolated by a Sac I/Kpn I digests from the pPho vectors and used as described in Example 3 (Table 11) to prepare separate composite light chains having the preferred CDR1 prepared above in combination with the H4L3 series affinity optimized light chain CDR3 prepared below.

E. Preparation of Randomized CDR3 in the Kappa Light Chain Variable Domain of Phagemid pComb3H-3b3 (the pMT4-3 Original Light Chain)

In order to further enhance the gp120 binding affinity of Fab 3b3 having a randomized heavy chain CDR1 and CDR3 prepared by overlap PCR as described in Example 1, 15 discontinuous preselected nucleotides in the light chain CDR3 of 3b3 in pComb3H were subjected to mutagenesis by overlap PCR. The 3b3 nucleotide sequences isolated from p3b3 having a CDR1 and CDR3 mutagenized heavy chain as prepared in Example 1 were subjected to overlap PCR to randomize 15 nucleotides from positions 265 to 267 and then from 271 to 282, the sites thus separated by one unmutagenized triplet in the p3b3-derived light chain variable domain as shown in FIG. 10 and listed as SEQ ID NO 62. Since p3b3 was derived from pMT4-3 without mutagenizing the light chain, the reference to the unmutagenized p3b3-derived light chain is the same as that to the light chain of pMT4-3. By randomizing the aforementioned 15 nucleotides, the encoded randomized amino acid residues are in CDR3 at position 89 then from positions 91 to 94 leaving conserved glutamine and tyrosine residues respectively in positions 88 and 90 and conserved tyrosine and threonine residues respectively in positions 95 and 96 thereby comprising the nine amino acid light chain CDR3.

As a result of the light chain CDR3 mutagenesis of 3b3 in pComb3H-3b3, Fabs selected from this new library as described below contained a total of five randomized amino acid residues of the nine amino acid residues in the Fab 3b3 light chain CDR3 and had the Fab 3b3 CDR1 and CDR3 mutagenized and selected heavy chain.

As described in Example 1B, overlap PCR was similarly performed on the pComb3H-3b3 expression vector template previously obtained. In the first round of PCR, the 5' oligonucleotide primer, KEF (SEQ ID NO 63) was used with 3' noncoding mutagenizing oligonucleotide primer, h4kcdr3-bo, having the nucleotide sequence 5'-CAGTTTGGTCCCCTGGCCAAAAGTGTAMNNMN-NMNNMNNATAMNNCTGACAGTAGTACAGTGCAA-AGTC-3' (SEQ ID NO 71) to amplify the light chain CDR3 and mutagenize the above-described 15 nucleotide region. The resultant amplified products were then purified as described in Example 1B and used in overlap PCR with the products from the second round.

The latter round of PCR was performed also as previously described in Example 1B but with the 5' coding overlapping oligonucleotide primer, hvkfr4-fo, having the nucleotide sequence 5'-TACACTTTTGGCCAGGGGACCAAACTG-3' (SEQ ID NO 72) and the 3' noncoding oligonucleotide primer, T7B (SEQ ID NO 66). The resultant amplified products were then purified as described in Example 1B and used in overlap PCR with the products from the first round using the oligonucleotide primer pair KEF and T7B to form a population of amplified light chain variable domains having newly mutagenized CDR3.

The light chain CDR3-randomized amplification products were then ligated into pComb3H-TT into which the p3b3 heavy chain variable domain nucleotide sequence encoding the amino acid residue sequence shown in SEQ ID NO 3 was ligated as described in Example 2B to form a library of p3b3-derived pComb3H-CDR3 randomized expression vectors. Phage-displayed Fabs, each having a mutagenized light chain and the p3b3-derived heavy chain, were then expressed and panned on gp120 as described in Example 1.

1) Amino Acid Residue Sequence Analysis of p3b3 Derived Fabs Having a Randomized Light Chain CDR3

Clones encoding phage-displayed Fabs that specifically bound to gp120 were then sequenced and the derived amino acid residue sequences were analyzed as previously described. Nucleic acid sequencing of the CDR3 randomized clones produced above was performed on three randomly chosen double-stranded Fab-expressing DNA clones using Sequenase 1.0 (USB, Cleveland, Ohio). The derived light chain amino acid residue sequences of the three selected specific synthetic gp120-specific H4L3 series of Fabs and 3b3 are shown in FIG. 12.

All selected H4L3 Fabs contained the p3b3-derived heavy chain variable domain. Each H4L3 Fab is unique by having mutagenized and selected amino acid sequences in CDR3 corresponding to the positions noted above. The complete light chain variable domain amino acid residue sequences of the H4L3 series are listed in the Sequence Listing as indicated in FIG. 12 by the assigned Sequence Listing identifiers.

2) Binding Affinity Analysis of gp120-Specific Fabs Having Randomized Light Chain CDR3

The DNA encoding the CDR3-mutagenized light chain H4L3 series Fabs selected for binding to gp120 obtained above were then transferred to the vector pPho-TT for expression of soluble Fabs as previously described. The soluble H4L3 series Fabs were then analyzed for binding affinity to gp120 strain IIB. Surface plasmon resonance was performed as described in Example 1H to determine the affinity of the selected Fabs.

The results of the Fab binding affinity analysis as measured by the equilibrium dissociation constant ($K_d$, M) of the H4L3 series Fabs are listed in Table 9. In addition, fold increases of affinity are also calculated as previously described.

TABLE 9

| Fab | [1]$K_d$ | [2]Fold Increase of Mutant $K_d$ Compared to MT4 $K_d$ |
| --- | --- | --- |
| H4L3-2 | $1.38 \times 10^{-10}$ | 45.3 |
| H4L3-3 | $3.31 \times 10^{-9}$ | 1.9 |
| H4L3-4 | $2.43 \times 10^{-10}$ | 25.7 |

[1]Dissociation constants of mutants' binding to gp 120 (IIIB strain).
[2]Fold increase calculated by dividing the $K_d$ of MT4 ($6.3 \times 10^{-9}$) with the $K_d$ of each mutant.

As evident from Table 9, two of the three Fabs, H4L3-2 and H4L3-4, exhibited enhanced affinities as measured by $K_d$ of binding to gp120 IIIB strain in the range of $10^{-10}$ M corresponding respectively to fold increases of approximately 45 and 26 fold over that of original Fab MT4 from which Fab 3b3, and thus the A–D Fabs, was derived. The fold increase as compared to the Fab 3b3 template from which Fabs A–D were derived can also be similarly calculated by using the $K_d$ of Fab 3b3 which is $7.7 \times 10^{-10}$ M.

The nucleotide sequences encoding the light chain variable domains from these derived CDR3 mutagenized Fabs were then separately used to create composite light chain variable domains having optimized mutagenized and selected CDR. Specifically, the nucleotide sequences encoding the mutagenized light chain CDR3 were isolated by Kpn I/Xba I digestion from the H4L3-pPho vectors and used as described in Example 3 (Table 11) to prepare separate composite light chains having the preferred CDR3 prepared above in combination with the A–D series affinity optimized light chain CDR1 prepared above.

3. Preparation of Randomized CDR Composite Fabs Having Optimized Affinity to gp120 Based Upon Preselected Randomized CDR of Phagemids 3b3 and MT4

A. Preparation of Randomized CDR3 Light Chain Based on Phagemid D Having a Randomized CDR1

1) PCR Amplification

In order to create a light chain having both randomized CDR1 and CDR3, one of the phagemids prepared in Example 2D, phagemid D, having a randomized CDR1 was used as a template for the subsequent randomization of CDR3. As described in Examples 1 and 2, the mutagenized light chain of phagemid D was derived from the nonrandomized light chain of 3b3, which is also referred to as the original light chain MT4 or 4L. In 3b3, the nonrandomized light chain of MT4 was retained while the heavy chain was randomized in CDR1 and CDR3. Since phagemid D was derived from phagemid 3b3 in pComb3H-3b3, phagemid D thus has the previously randomized 3b3-derived heavy chain and a newly randomized MT4 or 3b3 light chain in CDR1.

In this Example, phagemid D having a randomized CDR1 and CDR3 heavy chain sequence and a randomized CDR1 light chain sequence was subjected to light chain CDR3 mutagenesis as described herein. A preselected portion of the CDR3 light chain of phagemid D was selected for randomization by overlap PCR as described in Example 1B. The CDR3 originally from MT4 as described above contained 27 nucleotides that expressed the nine amino acid residue sequence QVYGASSYT (SEQ ID NO 6, from amino acid residue position 88 to 96). In mutagenizing the CDR3 light chain, the second (valine), and fourth through seventh amino acid residues (glycine, alanine, serine, serine) were randomized as dictated by the design of the oligonucleotide primer used to mutagenize the region. The first, third, eighth and ninth residues of the light chain CDR3 were retained as they are conserved residues found in light chains.

In the first round of PCR amplification, the phagemid D template was mutagenized using the 5' oligonucleotide primer KEF (SEQ ID NO 63) described in Example 2D and the 3' noncoding randomizing oligonucleotide primer h4kcdr3-bo (SEQ ID NO 71). The PCR products were purified as previously described and used in overlap PCR with the products of the second PCR.

The latter was performed on phagemid D with the 5' coding oligonucleotide primer hvkfr4-fo (SEQ ID NO 72) and the 3' noncoding oligonucleotide primer T7B (SEQ ID NO 66) described in Example 2D.

The PCR products of the second amplification were purified as previously described and used in overlap PCR with the products of the first PCR in overlap PCR with the primer pair KEF and T7B which provided for the overlap between the 5' end of the coding hvkfr4fo primer and the 5' end of the noncoding randomizing h4kcdr3bo primer. The library of overlap PCR products of the phagemid D-derived light chain having a population of randomized CDR3 in the context of the remainder of the phagemid D sequence, already having randomized and selected light chain CDR1 and heavy chain CDR1 and CDR3, were then purified as described in Example 1B and ligated into pComb3H-TT as described in Example 2B for subsequent phage-display Fab expression and screening as described below.

2) Selection of Anti-gp120 Fabs Having CDR1 and CDR3 Randomized Light Chains The construction of pComb3H-phagemid D-derived and newly mutagenized light chain CDR3-containing libraries was performed as previously described in Example 2B with the exception that the heavy chain variable domain cassette was obtained from phagemid D and light chain variable domain was provided in the amplified fragments having mutagenized CDR3. Following expression and panning as previously described, gp120-reactive phage-displayed Fabs were subjected to acid elution as previously described. The clones encoding the Fabs designated QA1 through QA9 were obtained using this standard elution procedure. When the affinities of the corresponding soluble Fabs were determined as described below and as shown in Table 10, the affinities were not as enhanced by the mutagenesis procedure as anticipated.

A separate elution procedure was, therefore, used to obtain Fab D-derived Fabs having higher affinities for gp120. In this procedure, the washed gp120-bound phage-displayed Fabs were competed by incubating 10 ug/well of soluble Fab 3b3 in a total volume of 25 ul for 1 to 2 hours. By competing with excess Fab in this way, the low affinity binders were eluted leaving the higher affinity binders immobilized with the gp120 for subsequent elution with acid performed as previously described. The clones obtained through the Fab competition/acid elution procedure encoded the Fabs designated QA10, QA11 and QA12, as shown in FIG. 13 and in Table 10 below.

3) Amino Acid Residue Sequence Analysis Comparison Between the Parent Fab D and the Fab D-based CDR1 and CDR3 Light Chain Randomized Fabs Clones encoding phagemid D-derived Fabs prepared above that specifically bound to gp120 and recovered using the elution procedures described above were then sequenced and the derived amino acid residue sequences were analyzed. Nucleic acid sequencing of the CDR3 randomized clones produced above was performed on four randomly chosen double-stranded Fab-expressing DNA clones using Sequenase 1.0 (USB, Cleveland, Ohio). The derived light chain amino acid residue sequences of the 12 selected specific synthetic gp120-specific QA series of Fabs and 3b3 are shown in FIG. 13.

All selected QA series Fabs contained the phagemid D-derived heavy chain variable domain, which is the p3b3 heavy chain as described in Example 2D, and the previously mutagenized and selected light chain CDR1 having the amino acid residue sequence RSSHQLDGSRVA (SEQ ID NO 70 from residue positions 22 to 33). Each QA Fab is unique by having mutagenized and selected amino acid sequences in the light chain CDR3 corresponding to the positions noted above. The complete light chain variable domain amino acid residue sequences of the QA series are listed in the Sequence Listing as indicated in FIG. 13 by the assigned Sequence Listing identifiers. The nucleotide sequence and corresponding encoded light chain variable domain from the Fab designated QA11 is referred to as LH for preparation of composite Fabs as described below.

4) Binding Affinity Analysis of gp120-Specific Fabs Derived from Phagemid D Having CDR1 and CDR3 Randomized Light Chain Domains The DNA encoding the CDR3-mutagenized light chain QA series Fabs selected for binding to gp120 obtained above were then transferred to the vector pPho-TT for expression of soluble Fabs as previously described. The soluble QA series Fabs were then analyzed for binding affinity to gp120 strain IIIB. Surface plasmon resonance was performed as described in Example 1H to determine the affinity of the selected Fabs.

The results of the Fab binding affinity analysis as measured by the equilibrium dissociation constant ($K_d$, M) of the QA11 series Fabs are listed in Table 10. In addition, fold increases of affinity are also calculated as previously described.

TABLE 10

| Fab | [1]$K_d$ | [2]Fold Increase of Mutant $K_d$ Compared to MT4 $K_d$ |
|---|---|---|
| QA1 | $5.1 \times 10^{-10}$ | 12.2 |
| QA2 | $4.2 \times 10^{-10}$ | 14.9 |
| QA3 | $1.2 \times 10^{-9}$ | 5.1 |
| QA4 | $5.0 \times 10^{-10}$ | 12.6 |
| QA5 | $4.6 \times 10^{-10}$ | 13.7 |
| QA6 | $2.2 \times 10^{-10}$ | 28.6 |
| QA7 | $4.5 \times 10^{-9}$ | 1.43 |
| QA8 | $4.4 \times 10^{-10}$ | 14.3 |
| QA9 | $6.1 \times 10^{-10}$ | 10.3 |
| QA10 | $7.4 \times 10^{-11}$ | 85.9 |
| QA11 | $6.7 \times 10^{-11}$ | 94.4 |
| QA12 | $1.3 \times 10^{-10}$ | 48.6 |

[1]Dissociation constants of mutants' binding to gp 120 (IIIB strain).
[2]Fold increase calculated by dividing the $K_d$ of MT4 ($6.3 \times 10^{-9}$) with the $K_d$ of each mutant.

As shown in Table 10, the Fab-expressing phage-displayed clones obtained from the Fab competition/acid elution exhibited higher affinities for gp120 as expected. While most of the QA Fabs had $K_d$'s greater than $10^{-10}$ M, the QA10 and QA11 Fabs had $K_d$'s exceeding $10^{-11}$ M of binding to gp120 IIIB strain with the latter corresponding respectively to fold increases of approximately 86 and 94 fold over that of original Fab MT4 from which Fab 3b3 and Fab D were derived.

The nucleotide sequences encoding the light chain variable domains from these derived CDR3 mutagenized Fabs were then separately used in creating unique composite affinity-optimized Fabs having a new heavy and light chain variable domains as described below and shown in Table 12 and 13.

B. Preparation of Composite Fabs by Combining Preselected Heavy and Light Chain Constructs 1) Preparation of pPho Constructs for Expressing Either Composite Heavy or Light Chains The nucleotide sequences encoding gp120-specific high affinity Fabs produced by the CDR-directed mutagenesis approach as taught in this invention and in Examples 1, 2 and 3A were then used to create new heavy and light chain variable domain constructs. The latter were then used to express new gp120 affinity-optimized heavy and light chain variable domains as components of new Fab compositions of this invention as described in Example 3B2) below.

In Table 11, four new heavy chain ($V_H$) phagemid constructs and one new light chain ($V_K$) phagemid construct were prepared using from the pPho-based constructs that contain nucleotide sequences encoding the specifically identified Fabs. To form the new heavy or light chain composite constructs, double restriction digests of selected pPho-Fab expressing constructs were performed resulting in isolating DNA fragments in which mutagenized CDR were contained. For all of the heavy chain digests, Xho I cuts in framework I, Spe I cuts in framework 4 and Sac II cuts in framework II at nucleotide positions 203 to 208 as shown in FIG. 4 and listed in SEQ ID NO 7. For all of the light chain digests, Sac I cuts in framework I, Xba I cuts in framework 4 and Kpn I cuts in framework II at nucleotide positions 100 to 105 as shown in FIG. 10 and listed in SEQ ID NO 62.

The particular digested fragments to form each composite heavy or light chain are identified in Table 11 along with the respective SEQ ID NO for each amino acid residue sequence encoded by the composite nucleotide sequence. In addition, the composite amino acid residue sequence for the light chain composite, designated L42, is shown in FIG. 14 and the composite amino acid residue sequence for the heavy chain composites, designated H31, H33, H101 and H103, are shown in FIG. 15.

TABLE 11

| $V_H$ or $V_K$ Chain Composite[1] | SEQ ID NO. | Phagemid DNA Chain Fragments Ligated to Form $V_H$ or $V_K$ Chain Composite Sequence |
|---|---|---|
| H31 ($V_H$) | 89 | H4H1-1 (Xho I/Sac II) + M556-3 (Sac II/Spe I) |
| H33 ($V_H$) | 90 | H4H1-3 (Xho I/Sac II) + M556-3 (Sac II/Spe I) |
| H101 ($V_H$) | 91 | H4H1-1 (Xho I/Sac II) + M556-10 (Sac II/Spe I) |
| H103 ($V_H$) | 92 | H4H1-3 (Xho I/Sac II) + M556-10 (Sac II/Spe I) |
| L42 ($V_K$) | 88 | D (Sac I/Kpn I) + H4L3-2 (Kpn I/Xba I) |

[1]Amino acid residue sequences of $V_H$ or $V_K$ (kappa light chain) chain composites are shown in FIGS. 15 and 14, respectively, and listed in the Sequence Listing according to the designated SEQ ID NOs.

In order to express the heavy and light chain composites, the isolated fragments were first ligated with the complementary termini resulting from the digestion to form one heavy or light chain fragment. The latter were then separately ligated with a similarly digested pPho-TT vector for directional ligation of the fragments into the vector for subsequent expression thereof for analysis of binding affinity as described below. Moreover, with the clones encoding the optimized Fabs produced in Examples 1, 2 and 3A, additional heavy and light chain composites are similarly prepared by ligating preselected isolated heavy or light chain DNA fragments.

2) Preparation of pPho Constructs for Expressing Unique Fabs Having Randomized CDR by Combining Preselected Heavy and Light Chain Constructs Using the heavy and light chain composite DNA constructs prepared above along with the nucleotide sequence encoding the original pMT4-derived light chain, designated 4L, the nucleotide sequence encoding the QA11-derived light chain (also referred to as LH), and the nucleotide sequence encoding the pMT4 original heavy chain designated 4H, unique DNA constructs for encoding preselected pairs of heavy and light chains were prepared.

The new Fab-encoding pPho constructs were prepared by combining Xho I/Spe I heavy chain constructs with Sac I/Xba I light chain constructs in pPho-TT by serial ligations. Alternatively, the pPho constructs in which either a preselected heavy or light chain construct was already present were digested with restriction enzymes for ligating the other chain as dictated by the chain present in the vector. For example, the expression vector, pPho-MT4, having the heavy and light chain constructs for expressing MT4, was digested with Sac I/Xba I for directional ligation of the L42 composite light chain construct prepared above. Similar constructions are accomplished by methods well known to one of ordinary skill in the art.

Preferred optimized composite constructs for encoding preferred unique high affinity binding Fabs of this invention are listed in Table 12. The pairs of heavy and light chain amino acid residue sequences of each preferred composite Fab are also indicated in Table 12 as pairs of SEQ ID NOs separated by a colon, e.g., 89:6 for the composite Fab having the mutagenized composite heavy chain H31 paired with the original unmutagenized light chain 4L.

TABLE 12

| Optimized Composite Fab Designations | Heavy ($V_H$):Light ($V_K$) Chain SEQ ID NOs |
|---|---|
| H31/4L | 89:6 |
| H31/L42 | 89:88 |
| 4H/L42 | 1:88 |
| H103/L42 | 92:88 |
| H33/L42 | 90:88 |
| H33/LH (LH = QA11 $V_K$) | 90:86 |
| H101/L42 | 91:88 |
| H101/4L (4L = MT4 $V_K$) | 91:6 |

Other pairs of heavy and light chains in addition to those listed in Table 12 are similarly constructed for expression of additional unique composite Fabs that exhibit binding to gp120.

4) Binding Affinity Analysis of Optimally CDR Randomized Composite Fabs Having Enhanced Affinity for gp120

For determination of the enhancement of affinity accomplished with the heavy and light chain CDR-directed mutagenesis optimization procedures as described in these Examples, soluble forms of the selected composite Fabs were expressed from the pPho composite constructs prepared above. The soluble composite Fabs were then analyzed for binding affinity to gp120 strain IIIB. Surface plasmon resonance was performed as described in Example 1H to determine the affinity of the selected composite Fabs.

The results of the composite Fab binding affinity analysis as measured by the association rate constants, $K_{on}$ and $K_{off}$, are shown in Table 13 and the calculated equilibrium association and dissociation constants ($K_a$, $M^{-1}$, $K_d$, M) are listed in Table 14. Selected individual clones are indicated by numbers separated by a dash from the Fab designation. In addition, fold increases of affinity are also calculated as previously described for each of the composite Fabs compared to that of the unmutagenized and nonoptimized gp120-binding MT4 Fab.

TABLE 13

| Fab | $K_{on}$ | $K_{off}$ |
|---|---|---|
| H31/4L-14 | $1.53 \times 10^5 \pm 2.6 \times 10^4$ | $3.39 \times 10^{-6} \pm 1.11 \times 10^{-7}$ |
| H31/L42-1 | $6.73 \times 10^4 \pm 6.5 \times 10^3$ | $1.75 \times 10^{-7} \pm 1.5 \times 10^{-7}$ |
| 4H*/L42-1 | $2.96 \times 10^5 \pm 1.8 \times 10^4$ | $6.15 \times 10^{-4} \pm 1.92 \times 10^{-6}$ |
| H103/L42-4 | $8.18 \times 10^4 \pm 6.5 \times 10^3$ | $9.41 \times 10^{-6} \pm 1.15 \times 10^{-7}$ |
| H33/L42-17 | $9.84 \times 10^4 \pm 6.5 \times 10^3$ | $1.78 \times 10^{-5} \pm 1.45 \times 10^{-7}$ |
| H33/LH-11 | $7.32 \times 10^4 \pm 1 \times 10^4$ | $5.45 \times 10^{-6} \pm 1.08 \times 10^{-7}$ |
| H101/L42-16 | $6.91 \times 10^4 \pm 7.9 \times 10^3$ | $1.19 \times 10^{-5} \pm 9.65 \times 10^{-8}$ |
| H101/L42-1 | $1.34 \times 10^5 \pm 8.7 \times 10^3$ | $1.74 \times 10^{-5} \pm 1.12 \times 10^{-7}$ |
| H101/4L-1 | $8.93 \times 10^5 \pm 1.3 \times 10^4$ | $3.39 \times 10^{-5} \pm 2.58 \times 10^{-7}$ |

*4H = Heavy Chain from MT4

TABLE 14

| Fab | $K_a$ | $K_d$ | [1]Fold Increase of Mutant $K_d$ Compared to MT4 $K_d$ |
|---|---|---|---|
| H31/4L-14 | $4.51 \times 10^{10}$ | $2.22 \times 10^{-11}$ | 283.8 |
| H31/L42-1 | $3.85 \times 10^{11}$ | $2.59 \times 10^{-12}$ | 2432.4 |
| 24H/L42-1 | $4.81 \times 10^8$ | $2.08 \times 10^{-9}$ | 3.02 |
| H103/L42-4 | $8.88 \times 10^9$ | $1.13 \times 10^{-10}$ | 55.8 |
| H33/L42-17 | $5.46 \times 10^9$ | $1.83 \times 10^{-10}$ | 34.4 |
| H33/LH-11 | $1.36 \times 10^{10}$ | $7.38 \times 10^{-11}$ | 85.4 |
| H101/L42-16 | $5.81 \times 10^9$ | $1.72 \times 10^{-10}$ | 36.6 |
| H101/L42-1 | $7.7 \times 10^9$ | $1.30 \times 10^{-10}$ | 48.5 |
| H101/4L-1 | $2.63 \times 10^9$ | $3.80 \times 10^{-10}$ | 16.6 |

[1]Fold increase calculated by dividing the $K_d$ of MT4 ($6.3 \times 10^{-9}$) with the $K_d$ of each mutant optimized composite Fab
[2]4H = Heavy chain from MT4

As shown in the above Tables, the Fab-expressing phage-displayed clones obtained from selectively combining mutagenesis-optimized heavy and light chain variable domain DNA cassettes encoded Fabs exhibiting high affinity binding to gp120. In particular, the Fabs in which either heavy or light chain CDR were mutagenized and selected for optimal gp120 binding exhibited $K_d$'s greater than $10^{-10}$ M, with two Fabs having $K_d$'s exceeding $10^{-11}$ M, and one preferred Fab designated H31/L42-1 exhibiting a $K_d$ greater than $10^{-12}$ M. The corresponding fold increases of gp120 binding affinity ranged from approximately 16 to over 2400 fold over that of original Fab MT4. In addition, the half-life of the binding of the gp120-reactive Fabs to gp120 can be obtained by dividing the natural log ($\ln_2$) with the $K_{off}$ rate constant, thereby obtaining a further parameter of the nature of the interaction. For the Fab designated H31/L42-1, the calculated half-life of binding to gp120 is 44.5 days compared to 24 minutes for the nonrandomized and nonoptimized Fab MT4 derived from a HIV-seropositive asymptomatic patient. Thus, the half-life determination is another way of characterizing the high affinity binding of the synthetic optimized Fabs of this invention to gp120 of HIV.

The Fab designated H31/L42-1 having the highest affinity was a Fab composite of the heavy chain composite H31 comprising heavy chain CDR1-mutagenized Fab H4H1 and heavy chain CDR3-mutagenized Fab M556–3 added in combination with the light chain composite L42 comprising light chain CDR1-mutagenized region from Fab D and light chain CDR3-mutagenized Fab H4L3-2.

A cell culture of E. coli strain DH10B containing the pPho construct in which the nucleotide sequence encoding the Fab H31/L42-1 is present has been deposited with American Type Culture Collection on Sep. 16, 1994, as described in Example 4 and has been assigned the ATCC Accession Number 69691.

Thus, the methods of this invention, in utilizing CDR-directed mutagenesis of both heavy and light chain genes, has generated unique Fabs not previously available by evolutionary selection pressures nor present in a patient generating endogenous antibodies directed against gp120 of HIV. The composite Fabs prepared in Example 3 along with the gp120-reactive Fabs selected from the four libraries prepared in Example 2 represent Fabs exhibiting higher affinity binding to gp120 than any other currently known gp120-reactive Fabs or intact immunoglobulins.

The preferred synthetic Fabs exhibiting high affinity binding to gp120 as obtained and characterized as described herein are listed in Table 15 where each Fab designation is listed along with the corresponding affinity measurement in Kd, M. In addition, the amino acid residue sequences of the heavy and light chain variable domains comprising the preferred Fabs of this invention are indicated in Table 15 by pairs of SEQ ID NOs separated by a colon. For example, the heavy and light chain amino acid residue sequences of the highest affinity binding Fab, H31/L42-1, respectively correspond to SEQ ID NO 89 and 88 and are listed as such in the Sequence Listing.

TABLE 15

| Fab Designation | $K_d$ | SEQ ID NOs of $V_H:V_K$ Pairs |
|---|---|---|
| MT4 (=Fab 4) | $6.3 \times 10^{-9}$ | 1:6 |
| 3b3 | $7.7 \times 10^{-10}$ | 3:6 |
| M556-2 | $4.39 \times 10^{-10}$ | 54:6 |
| M556-3 | $1.0 \times 10^{-10}$ | 55:6 |
| M556-7 | $1.3 \times 10^{-10}$ | 56:6 |
| M556-10 | $9.06 \times 10^{-10}$ | 57:6 |
| M556-15 | $1.74 \times 10^{-10}$ | 58:6 |
| M556-16 | $1.39 \times 10^{-10}$ | 59:6 |
| C | $6.8 \times 10^{-10}$ | 3:69 |
| D | $2.2 \times 10^{-10}$ | 3:70 |
| H4L3-2 | $1.38 \times 10^{-10}$ | 3:73 |
| H4L3-4 | $2.43 \times 10^{-10}$ | 3:75 |
| QA1 | $5.1 \times 10^{-10}$ | 3:76 |
| QA2 | $4.2 \times 10^{-10}$ | 3:77 |
| QA4 | $5.0 \times 10^{-10}$ | 3:79 |
| QA5 | $4.6 \times 10^{-10}$ | 3:80 |
| QA6 | $2.2 \times 10^{-10}$ | 3:82 |
| QA8 | $4.4 \times 10^{-10}$ | 3:83 |
| QA9 | $6.1 \times 10^{-10}$ | 3:84 |
| QA10 | $7.4 \times 10^{-11}$ | 3:85 |
| QA11 | $6.7 \times 10^{-11}$ | 3:86 |
| QA12 | $1.3 \times 10^{-10}$ | 3:87 |
| [1]H31/4L-14 | $2.2 \times 10^{-11}$ | 89:6 |
| [2]H31/L42-1 | $2.59 \times 10^{-12}$ | 89:88 |
| H103/L42-4 | $1.13 \times 10^{-10}$ | 92:88 |
| H33/L42-17 | $1.83 \times 10^{-10}$ | 90:88 |
| [3]H33/LH-11 | $7.38 \times 10^{-11}$ | 90:86 |
| [4]H101/L42-16 | $1.7 \times 10^{-10}$ | 91:88 |
| [4]H101/L42-1 | $1.3 \times 10^{-10}$ | 91:88 |
| H101/4L-1 | $3.8 \times 10^{-10}$ | 91:6 |

[1]4L = MT4 or 3b3 $V_K$
[2]Fab expressed by plasmid pPho-H31/L42-1 in E. coli ATCC deposit 69691
[3]LH = light chain of QA11
[4]Separate selected Fabs having the same $V_H/V_K$ 4. Deposit of Materials The plasmid, pMT4, was deposited on Oct. 19, 1993, with the American Type Culture Collection, 1301 Parklawn Drive, Rockville, Md., USA (ATCC) and has been assigned the ATCC accession number 75574. The deposit provides a plasmid that encodes and expresses a Fab antibody designated MT4, the heavy and light chain variable domain amino acid sequences of which are listed in SEQ ID NO 1 and 6, respectively, and are shown in FIGS. 1 and 2.

The cell culture, designated DH1OB-pPho-H31/L42-1, containing plasmid pPho-H31/L42-1, was deposited on or before Sep. 19, 1994 with ATCC and has been assigned the ATCC accession number 69691. The deposit provides an E. coli cell culture containing a pPho-based plasmid from which a Fab antibody designated H31/L42-1 is expressed, the heavy and light chain amino acid sequences of which are listed in SEQ ID NO 89 and 88, respectively, and are shown in FIGS. 15 and 14.

These deposits were made under the provisions of the Budapest Treaty on the International Recognition of the Deposit of Microorganisms for the Purpose of Patent Procedure and the Regulations thereunder (Budapest Treaty). This assures maintenance of a viable plasmid and viable cell culture for 30 years from the date of each deposit. The plasmid and cell culture will be made available by ATCC under the terms of the Budapest Treaty which assures permanent and unrestricted availability of the progeny of the plasmid and culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the plasmid and culture deposits should die or be lost or destroyed when cultivated under suitable conditions, it will be promptly replaced on notification with a viable specimen of the same plasmid and culture. Availability of the deposits is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiments are intended as single illustrations of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

```
                          SEQUENCE LISTING (1) GENERAL INFORMATION:

(iii) NUMBER OF SEQUENCES: 92

(2) INFORMATION FOR SEQ ID NO: 1:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 1:

Leu Glu Gln Ser Gly Ala Glu Val Lys Lys P ro Gly Ala Ser Val Lys
1               5                   10                  15

Val Ser Cys Gln Ala Ser Gly Tyr Arg Phe S er Asn Phe Val Ile His
                20                  25                  30

Trp Val Arg Gln Ala Pro Gly Gln Arg Phe G lu Trp Met Gly Trp Ile
            35                  40                  45

Asn Pro Tyr Asn Gly Asn Lys Glu Phe Ser A la Lys Phe Gln Asp Arg
        50                  55                  60

Val Thr Phe Thr Ala Asp Thr Ser Ala Asn T hr Ala Tyr Met Glu Leu
65                  70                  75                  80

Arg Ser Leu Arg Ser Ala Asp Thr Ala Val T yr Tyr Cys Ala Arg Val
                85                  90                  95

Gly Pro Tyr Ser Trp Asp Asp Ser Pro Gln A sp Asn Tyr Tyr Met Asp
            100                 105                 110

Val Trp Gly Lys Gly Thr Thr Val Ile Val S er Ser
        115                 120

(2) INFORMATION FOR SEQ ID NO: 2:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 2:

Leu Glu Gln Ser Gly Ala Glu Val Lys Lys P ro Gly Ala Ser Val Lys
1               5                   10                  15

Val Ser Cys Gln Ala Ser Gly Tyr Arg Phe S er Asn Phe Thr Leu Met
                20                  25                  30

Trp Val Arg Gln Ala Pro Gly Gln Arg Phe G lu Trp Met Gly Trp Ile
            35                  40                  45

Asn Pro Tyr Asn Gly Asn Lys Glu Phe Ser A la Lys Phe Gln Asp Arg
        50                  55                  60

Val Thr Phe Thr Ala Asp Thr Ser Ala Asn T hr Ala Tyr Met Glu Leu
65                  70                  75                  80
```

```
Arg Ser Leu Arg Ser Ala Asp Thr Ala Val Tyr Tyr Cys Ala Arg Val
                85                  90                  95

Gly Gln Trp Asn Trp Asp Asp Ser Pro Gln Asp Asn Tyr Tyr Met Asp
            100                 105                 110

Val Trp Gly Lys Gly Thr Thr Val Ile Val Ser Ser
        115                 120
```

(2) INFORMATION FOR SEQ ID NO: 3:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 3:

```
Leu Glu Gln Ser Gly Ala Glu Val Lys Lys Pro Gly Ala Ser Val Lys
1               5                   10                  15

Val Ser Cys Gln Ala Ser Gly Tyr Arg Phe Ser Asn Phe Thr Val His
                20                  25                  30

Trp Val Arg Gln Ala Pro Gly Gln Arg Phe Glu Trp Met Gly Trp Ile
            35                  40                  45

Asn Pro Tyr Asn Gly Asn Lys Glu Phe Ser Ala Lys Phe Gln Asp Arg
        50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Glu Trp Gly Trp Asp Asp Ser Pro Gln Asp Asn Tyr Tyr Met Asp
            100                 105                 110

Val Trp Gly Lys Gly Thr Thr Val Ile Val Ser Ser
        115                 120
```

(2) INFORMATION FOR SEQ ID NO: 4:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO: 4:

```
Leu Glu Gln Ser Gly Ala Glu Val Lys Lys Pro Gly Ala Ser Val Lys
1               5                   10                  15

Val Ser Cys Gln Ala Ser Gly Tyr Arg Phe Ser Asn Tyr Thr Leu Ile
                20                  25                  30

Trp Val Arg Gln Ala Pro Gly Gln Arg Phe Glu Trp Met Gly Trp Ile
            35                  40                  45

Asn Pro Tyr Asn Gly Asn Lys Glu Phe Ser Ala Lys Phe Gln Asp Arg
        50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Pro Trp Asn Trp Asp Ser Pro Gln Asp Asn Tyr Tyr Met Asp Val
            100                 105                 110
```

```
Trp Gly Lys Gly Thr Thr Val Ile Val Ser S er
            115                 120
```

(2) INFORMATION FOR SEQ ID NO: 5:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 5:

```
Leu Gln Ser Gly Ala Glu Val Lys Lys P ro Gly Ala Ser Val Lys
1               5                   10                  15

Val Ser Cys Gln Ala Ser Gly Tyr Arg Phe S er Asn Phe Thr Val His
            20                  25              30

Trp Val Arg Gln Ala Pro Gly Gln Arg Phe G lu Trp Met Gly Trp Ile
            35                  40                  45

Asn Pro Tyr Asn Gly Asn Lys Glu Phe Ser A la Lys Phe Gln Asp Arg
        50              55                  60

Val Thr Phe Thr Ala Asp Thr Ser Ala Asn T hr Ala Tyr Met Glu Leu
65              70                  75                  80

Arg Ser Leu Arg Ser Ala Asp Thr Ala Val T yr Tyr Cys Ala Arg Val
            85                  90                  95

Gly Pro Trp Arg Trp Asp Asp Ser Pro Gln A sp Asn Tyr Tyr Met Asp
            100                 105                 110

Val Trp Gly Lys Gly Thr Ile Val Ile Val S er Ser
            115                 120
```

(2) INFORMATION FOR SEQ ID NO: 6:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 6:

```
Glu Leu Thr Gln Ser Pro Gly Thr Leu Ser L eu Ser Pro Gly Glu Arg
1               5                   10                  15

Ala Thr Phe Ser Cys Arg Ser Ser His Ser I le Arg Ser Arg Arg Val
            20                  25                  30

Ala Trp Tyr Gln His Lys Pro Gly Gln Ala P ro Arg Leu Val Ile His
            35                  40                  45

Gly Val Ser Asn Arg Ala Ser Gly Ile Ser A sp Arg Phe Ser Gly Ser
        50              55                  60

Gly Ser Gly Thr Asp Phe Thr Leu Thr Ile T hr Arg Val Glu Pro Glu
65              70                  75                  80

Asp Phe Ala Leu Tyr Tyr Cys Gln Val Tyr G ly Ala Ser Ser Tyr Thr
            85                  90                  95

Phe Gly Gln Gly Thr Lys Leu Glu Arg Lys A rg Thr
            100                 105
```

(2) INFORMATION FOR SEQ ID NO: 7:

(i) SEQUENCE CHARACTERISTICS:
        (A) LENGTH: 372 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO: 7:

CTCGAGCAGT CTGGGGCTGA GGTGAAGAAG CCTGGGGCCT CAGTGAAGGT T TCTTGTCAA      60

GCTTCTGGAT ACAGATTCAG TAACTTTGTT ATTCATTGGG TGCGCCAGGC C CCCGGACAG    120

AGGTTTGAGT GGATGGGATG GATCAATCCT TACAACGGAA ACAAAGAATT T TCAGCGAAG    180

TTCCAGGACA GAGTCACCTT TACCGCGGAC ACATCCGCGA ACACAGCCTA C ATGGAGTGG    240

AGGAGCCTCA GATCTGCAGA CACGGCTGTT TATTATTGTG CGAGAGTGGG G CCATATAGT    300

TGGGATGATT CTCCCCAGGA CAATTATTAT ATGGACGTCT GGGGCAAAGG G ACCACGGTC    360

ATCGTCTCCT CA                                                        372

(2) INFORMATION FOR SEQ ID NO: 8:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 8:

Asn Phe Val Ile His
1               5

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

GCAATTAACC CTCACTAAAG GG                                              22

(2) INFORMATION FOR SEQ ID NO: 10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

AGAAGCTTGA CAAGAAGAAA CCTTC                                           25

(2) INFORMATION FOR SEQ ID NO: 11:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

GAAGGTTTCT TGTCAAGCTT CTGGATACAG ATTCAGTNNS NNSNNSNNSN N STGGGTGCG     60

CCAGGCCCCC 70

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

TTGATATTCA CAAACGAATG G 21

(2) INFORMATION FOR SEQ ID NO: 13:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

CCCTTTGCCC CAGACGTCCA TATAATAATT GTCCTGGGGA GAATCATCMN N MNNMNNMNN 60

CCCCACTCTC GCACA 75

(2) INFORMATION FOR SEQ ID NO: 14:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 14:

Arg Tyr Thr Val Phe
1          5

(2) INFORMATION FOR SEQ ID NO: 15:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 15:

Asn Trp Ser Val Met
1          5

(2) INFORMATION FOR SEQ ID NO: 16:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 16:

Gly Tyr Thr Leu Met
1          5

(2) INFORMATION FOR SEQ ID NO: 17:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 17:

Asn Phe Thr Leu Leu
1         5

(2) INFORMATION FOR SEQ ID NO: 18:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 18:

His Tyr Ser Leu Met
1         5

(2) INFORMATION FOR SEQ ID NO: 19:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 19:

Asn Trp Val Val His
1         5

(2) INFORMATION FOR SEQ ID NO: 20:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 20:

Asn Phe Ser Ile Met
1         5

(2) INFORMATION FOR SEQ ID NO: 21:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 21:

Asn Phe Ala Ile His
1         5

(2) INFORMATION FOR SEQ ID NO: 22:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 22:

Asn Phe Thr Met Val
1               5

(2) INFORMATION FOR SEQ ID NO: 23:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 23:

Asn Phe Thr Leu Gln
1               5

(2) INFORMATION FOR SEQ ID NO: 24:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 24:

Tyr Phe Thr Met His
1               5

(2) INFORMATION FOR SEQ ID NO: 25:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 25:

Ser Tyr Pro Leu His
1               5

(2) INFORMATION FOR SEQ ID NO: 26:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 26:

Asn Phe Thr Leu Met
1               5

(2) INFORMATION FOR SEQ ID NO: 27:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 27:

Asn Tyr Thr Ile Met
1               5

(2) INFORMATION FOR SEQ ID NO: 28:

(i) SEQUENCE CHARACTERISTICS:
         (A) LENGTH: 5 amino acids
         (B) TYPE: amino acid
         (D) TOPOLOGY: linear (ii) MOLECULE TYPE: protein (xi) SEQUENCE DESCRIPTION: SEQ ID NO: 28:

Asn Phe Thr Val His
1               5

(2) INFORMATION FOR SEQ ID NO: 29:

(i) SEQUENCE CHARACTERISTICS:
         (A) LENGTH: 5 amino acids
         (B) TYPE: amino acid
         (D) TOPOLOGY: linear (ii) MOLECULE TYPE: protein (xi) SEQUENCE DESCRIPTION: SEQ ID NO: 29:

Asn Tyr Thr Leu Ile
1               5

(2) INFORMATION FOR SEQ ID NO: 30:

(i) SEQUENCE CHARACTERISTICS:
         (A) LENGTH: 5 amino acids
         (B) TYPE: amino acid
         (D) TOPOLOGY: linear (ii) MOLECULE TYPE: protein (xi) SEQUENCE DESCRIPTION: SEQ ID NO: 30:

Asn Phe Ile Ile Met
1               5

(2) INFORMATION FOR SEQ ID NO: 31:

(i) SEQUENCE CHARACTERISTICS:
         (A) LENGTH: 5 amino acids
         (B) TYPE: amino acid
         (D) TOPOLOGY: linear (ii) MOLECULE TYPE: protein (xi) SEQUENCE DESCRIPTION: SEQ ID NO: 31:

Asn Phe Ser Ile Met
1               5

(2) INFORMATION FOR SEQ ID NO: 32:

(i) SEQUENCE CHARACTERISTICS:
         (A) LENGTH: 5 amino acids
         (B) TYPE: amino acid
         (D) TOPOLOGY: linear (ii) MOLECULE TYPE: protein (xi) SEQUENCE DESCRIPTION: SEQ ID NO: 32:

```
Asn Tyr Thr Ile Gln
1               5
```

(2) INFORMATION FOR SEQ ID NO: 33:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 33:

```
Asn Phe Thr Val His
1               5
```

(2) INFORMATION FOR SEQ ID NO: 34:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 34:

```
Pro Tyr Ser Trp
1
```

(2) INFORMATION FOR SEQ ID NO: 35:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 35:

```
Gln Trp Asn Trp
1
```

(2) INFORMATION FOR SEQ ID NO: 36:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 36:

```
Pro Trp Thr Trp
1
```

(2) INFORMATION FOR SEQ ID NO: 37:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 37:

```
Glu Trp Gly Trp
1
```

(2) INFORMATION FOR SEQ ID NO: 38:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 38:

Pro Trp Asn Trp
1

(2) INFORMATION FOR SEQ ID NO: 39:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 39:

Leu Trp Asn Trp
1

(2) INFORMATION FOR SEQ ID NO: 40:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 40:

Ser Trp Arg Trp
1

(2) INFORMATION FOR SEQ ID NO: 41:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 41:

Pro Tyr Ser Trp
1

(2) INFORMATION FOR SEQ ID NO: 42:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 42:

Pro Trp Arg Trp
1

(2) INFORMATION FOR SEQ ID NO: 43:

(i) SEQUENCE CHARACTERISTICS:

(A) LENGTH: 4691 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO: 43:

```
GGGAAATTGT AAGCGTTAAT ATTTTGTTAA AATTCGCGTT AAATTTTTGT T AAATCAGCT      60
CATTTTTTAA CCAATAGGCC GAAATCGGCA AAATCCCTTA TAAATCAAAA G AATAGACCG     120
AGATAGGGTT GAGTGTTGTT CCAGTTTGGA ACAAGAGTCC ACTATTAAAG A ACGTGGACT     180
CCAACGTCAA AGGGCGAAAA ACCGTCTATC AGGGCGATGG CCCACTACGT G AACCATCAC     240
CCTAATCAAG TTTTTTGGGG TCGAGGTGCC GTAAAGCACT AAATCGGAAC C CTAAAGGGA     300
GCCCCCGATT TAGAGCTTGA CGGGGAAAGC CGGCGAACGT GGCGAGAAAG G AAGGGAAGA     360
AAGCGAAAGG AGCGGGCGCT AGGGCGCTGG CAAGTGTAGC GGTCACGCTG C GCGTAACCA     420
CCACACCCGC CGCGCTTAAT GCGCCGCTAC AGGGCGCGTC AGGTGGCACT T TTCGGGGAA     480
ATGTGCGCGG AACCCCTATT TGTTTATTTT TCTAAATACA TTCAAATATG T ATCCGCTCA     540
TGAGACAATA ACCCTGATAA ATGCTTCAAT AATATTGAAA AAGGAAGAGT A TGAGTATTC     600
AACATTTCCG TGTCGCCCTT ATTCCCTTTT TTGCGGCATT TTGCCTTCCT G TTTTTGCTC     660
ACCCAGAAAC GCTGGTGAAA GTAAAAGATG CTGAAGATCA GTTGGGTGCA C GAGTGGGTT     720
ACATCGAACT GGATCTCAAC AGCGGTAAGA TCCTTGAGAG TTTTCGCCCC G AAGAACGTT     780
TTCCAATGAT GAGCACTTTT AAAGTTCTGC TATGTGGCGC GGTATTATCC C GTATTGACG     840
CCGGGCAAGA GCAACTCGGT CGCCGCATAC ACTATTCTCA GAATGACTTG G TTGAGTACT     900
CACCAGTCAC AGAAAAGCAT CTTACGGATG GCATGACAGT AAGAGAATTA T GCAGTGCTG     960
CCATAACCAT GAGTGATAAC ACTGCGGCCA ACTTACTTCT GACAACGATC G GAGGACCGA    1020
AGGAGCTAAC CGCTTTTTTG CACAACATGG GGGATCATGT AACTCGCCTT G ATCGTTGGG    1080
AACCGGAGCT GAATGAAGCC ATACCAAACG ACGAGCGTGA CACCACGATG C CTGTAGCAA    1140
TGGCAACAAC GTTGCGCAAA CTATTAACTG GCGAACTACT TACTCTAGCT T CCCGGCAAC    1200
AATTAATAGA CTGGATGGAG GCGGATAAAG TTGCAGGACC ACTTCTGCGC T CGGCCCTTC    1260
CGGCTGGCTG GTTTATTGCT GATAAATCTG GAGCCGGTGA GCGTGGGTCT C GCGGTATDA    1320
TTGCAGCACT GGGGCCAGAT GGTAAGCCCT CCCGTATCGT AGTTATCTAC A CGACGGGGA    1380
GTCAGGCAAC TATGGATGAA CGAAATAGAC AGATCGCTGA GATAGGTGCC T CACTGATTA    1440
AGCATTGGTA ACTGTCAGAC CAAGTTTACT CATATATACT TTAGATTGAT T TAAAACTTC    1500
ATTTTTAATT TAAAAGGATC TAGGTGAAGA TCCTTTTTGA TAATCTCATG A CCAAAATCC    1560
CTTAACGTGA GTTTTCGTTC CACTGAGCGT CAGACCCCGT AGAAAAGATC A AAGGATCTT    1620
CTTGAGATCC TTTTTTTCTG CGCGTAATCT GCTGCTTGCA AACAAAAAAA C CACCGCTAC    1680
CAGCGGTGGT TTGTTTGCCG GATCAAGAGC TACCAACTCT TTTTCCGAAG G TAACTGGCT    1740
TCAGCAGAGC GCAGATACCA AATACTGTCC TTCTAGTGTA GCCGTAGTTA G GCCACCACT    1800
TCAAGAACTC TGTAGCACCG CCTACATACC TCGCTCTGCT AATCCTGTTA C CAGTGGCTG    1860
CTGCCAGTGG CGATAAGTCG TGTCTTACCG GGTTGGACTC AAGACGATAG T TACCGGATA    1920
AGGCGCAGCG GTCGGGCTGA ACGGGGGGTT CGTGCACACA GCCCAGCTTG G AGCGAACGA    1980
CCTACACCGA ACTGAGATAC CTACAGCGTG AGCTATGAGA AAGCGCCACG C TTCCCGAAG    2040
GGAGAAAGGC GGACAGGTAT CCGGTAAGCG GCAGGGTCGG AACAGGAGAG C GCACGAGGG    2100
```

```
AGCTTCCAGG GGGAAACGCC TGGTATCTTT ATAGTCCTGT CGGGTTTCGC C ACCTCTGAC     2160

TTGAGCGTCG ATTTTTGTGA TGCTCGTCAG GGGGGCGGAG CCTATGGAAA A ACGCCAGCA     2220

ACGCGGCCTT TTTACGGTTC CTGGCCTTTT GCTGGCCTTT TGCTCACATG T TCTTTCCTG     2280

CGTTATCCCC TGATTCTGTG GATAACCGTA TTACCGCCTT TGAGTGAGCT G ATACCGCTC     2340

GCCGCAGCCG AACGACCGAG CGCAGCGAGT CAGTGAGCGA GGAAGCGGAA G AGCGCCCAA     2400

TACGCAAACC GCCTCTCCCC GCGCGTTGGC CGATTCATTA ATGCAGCTGG C ACGACAGGT     2460

TTCCCGACTG GAAAGCGGGC AGTGAGCGCA ACGCAATTAA TGTGAGTTAG C TCACTCATT     2520

AGGCACCCCA GGCTTTACAC TTTATGCTTC CGGCTCGTAT GTTGTGTGGA A TTGTGAGCG     2580

GATAACAATT GAATTCAGGA GGAATTTAAA ATGAAAAAGA CAGCTATCGC G ATTGCAGTG     2640

GCACTGGCTG GTTTCGCTAC CGTGGCCCAG GCGGCCGAGC TCACGCAGTC T CCAGGCACC     2700

CTGTCTTTGT CTCCAGGGGA AAGAGCCACC CTCTCCTGCA GGGCCAGTCA C AGTGTTAGC     2760

AGGGCCTACT TAGCCTGGTA CCAGCAGAAA CCTGGCCAGG CTCCCAGGCT C CTCATCTAT     2820

GGTACATCCA GCAGGGCCAC TGGCATCCCA GACAGGTTCA GTGGCAGTGG G TCTGGGACA     2880

GACTTCACTC TCACCATCAG CAGACTGGAG CCTGAAGATT TTGCAGTGTA C TACTGTCAG     2940

CAGTATGGTG GCTCACCGTG GTTCGGCCAA GGGACCAAGG TGGAACTCAA A CGAACTGTG     3000

GCTGCACCAT CTGTCTTCAT CTTCCCGCCA TCTGATGAGC AGTTGAAATC T GGAACTGCC     3060

TCTGTTGTGT GCCTGCTGAA TAACTTCTAT CCCAGAGAGG CCAAAGTACA G TGGAAGGTG     3120

GATAACGCCC TCCAATCGGG TAACTCCCAG GAGAGTGTCA CAGAGCAGGA C AGCAAGGAC     3180

AGCACCTACA GCCTCAGCAG CACCCTGACG CTGAGCAAAG CAGACTACGA G AAACACAAA     3240

GTCTACGCCT GCGAAGTCAC CCATCAGGGC CTGAGTTCGC CCGTCACAAA G AGCTTCAAC     3300

AGGGGAGAGT GTTAATTCTA GATAATTAAT TAGGAGGAAT TTAAAATGAA A TACCTATTG     3360

CCTACGGCAG CCGCTGGATT GTTATTACTC GCTGCCCAAC CAGCCATGGC C GAGGTGCAG     3420

CTGCTCGAGC AGTCTGGGGC TGAGGTGAAG AAGCCTGGGT CCTCGGTGAA G GTCTCCTGC     3480

AGGGCTTCTG GAGGCACCTT CAACAATTAT GCCATCAGCT GGGTGCGACA G GCCCCTGGA     3540

CAAGGGCTTG AGTGGATGGG AGGGATCTTC CCTTTCCGTA ATACAGCAAA G TACGCACAA     3600

CACTTCCAGG GCAGAGTCAC CATTACCGCG GACGAATCCA CGGGCACAGC C TACATGGAG     3660

CTGAGCAGCC TGAGATCTGA GGACACGGCC ATATATTATT GTGCGAGAGG G GATACGATT     3720

TTTGGAGTGA CCATGGGATA CTACGCTATG GACGTCTGGG GCCAAGGGAC C ACGGTCACC     3780

GTCTCCGCAG CCTCCACCAA GGGCCCATCG GTCTTCCCCC TGGCACCCTC C TCCAAGAGC     3840

ACCTCTGGGG GCACAGCGGC CCTGGGCTGC CTGGTCAAGG ACTACTTCCC C GAACCGGTG     3900

ACGGTGTCGT GGAACTCAGG CGCCCTGACC AGCGGCGTGC ACACCTTCCC G GCTGTCCTA     3960

CAGTCCTCAG GACTCTACTC CCTCAGCAGC GTGGTGACCG TGCCCTCCAG C AGCTTGGGC     4020

ACCCAGACCT ACATCTGCAA CGTGAATCAC AAGCCCAGCA ACACCAAGGT G GACAAGAAA     4080

GCAGAGCCCA AATCTTGTGA CAAAACTAGT GGCCAGGCCG GCCAGGAGGG T GGTGGCTCT     4140

GAGGGTGGCG GTTCTGAGGG TGGCGGCTCT GAGGGAGGCG GTTCCGGTGG T GGCTCTGGT     4200

TCCGGTGATT TTGATTATGA AAAGATGGCA AACGCTAATA AGGGGGCTAT G ACCGAAAAT     4260

GCCGATGAAA ACGCGCTACA GTCTGACGCT AAAGGCAAAC TTGATTCTGT C GCTACTGAT     4320

TACGGTGCTG CTATCGATGG TTTCATTGGT GACGTTTCCG GCCTTGCTAA T GGTAATGGT     4380

GCTACTGGTG ATTTTGCTGG CTCTAATTCC CAAATGGCTC AAGTCGGTGA C GGTGATAAT     4440

TCACCTTTAA TGAATAATTT CCGTCAATAT TTACCTTCCC TCCCTCAATC G GTTGAATGT     4500
```

```
CGCCCTTTTG TCTTTAGCGC TGGTAAACCA TATGAATTTT CTATTGATTG T GACAAAATA    4560

AACTTATTCC GTGGTGTCTT TGCGTTTCTT TTATATGTTG CCACCTTTAT G TATGTATTT    4620

TCTACGTTTG CTAACATACT GCGTAATAAG GAGTCTTAAG CTAGCTAATT A ATTTAAGCG    4680

GCCGCAGATC T                                                          4691
```

(2) INFORMATION FOR SEQ ID NO: 44:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 44:

```
Glu Val Gln Leu Leu Glu
1               5
```

(2) INFORMATION FOR SEQ ID NO: 45:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 45:

```
Leu Gln Gln Ser Gly Ala Glu Val Lys Lys P ro Gly Ala Ser Val Lys
1               5                   10                  15

Val Ser Cys Gln Ala Ser Gly Tyr Arg Phe S er His Phe Thr Val His
                20                  25                  30

Trp Val Arg Gln Ala Pro Gly Gln Arg Phe G lu Trp Met Gly Trp Ile
            35                  40                  45

Asn Pro Tyr Asn Gly Asn Lys Glu Phe Ser A la Lys Phe Gln Asp Arg
        50                  55                  60

Val Thr Phe Thr Ala Asp Thr Ser Ala Asn T hr Ala Tyr Met Glu Leu
65                  70                  75                  80

Arg Ser Leu Arg Ser Ala Asp Thr Ala Val T yr Tyr Cys Ala Arg Val
                85                  90                  95

Gly Pro Tyr Ser Trp Asp Asp Ser Pro Gln A sp Asn Tyr Tyr Met Asp
            100                 105                 110

Val Trp Gly Lys Gly Thr Thr Val Ile Val S er Ser
            115                 120
```

(2) INFORMATION FOR SEQ ID NO: 46:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 46:

```
Leu Gln Gln Ser Gly Ala Glu Val Lys Lys P ro Gly Ala Ser Val Lys
1               5                   10                  15

Val Ser Cys Gln Ala Ser Gly Tyr Arg Phe S er His Phe Thr Leu His
                20                  25                  30

Trp Val Arg Gln Ala Pro Gly Gln Arg Phe G lu Trp Met Gly Trp Ile
```

```
                  35                  40                  45
Asn Pro Tyr Asn Gly Asn Lys Glu Phe Ser Ala Lys Phe Gln Asp Arg
            50                  55                  60
Val Thr Phe Thr Ala Asp Thr Ser Ala Asn Thr Ala Tyr Met Glu Leu
 65                  70                  75                  80
Arg Ser Leu Arg Ser Ala Asp Thr Ala Val Tyr Tyr Cys Ala Arg Val
                85                  90                  95
Gly Pro Tyr Ser Trp Asp Asp Ser Pro Gln Asp Asn Tyr Tyr Met Asp
               100                 105                 110
Val Trp Gly Lys Gly Thr Thr Val Ile Val Ser Ser
           115                 120
```

(2) INFORMATION FOR SEQ ID NO: 47:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 47:

```
Leu Glu Gln Ser Gly Ala Glu Val Lys Lys Pro Gly Ala Ser Val Lys
 1               5                  10                  15
Val Ser Cys Gln Ala Ser Gly Tyr Arg Phe Ser His Phe Thr Ile Met
                20                  25                  30
Trp Val Arg Gln Ala Pro Gly Gln Arg Phe Glu Trp Met Gly Trp Ile
            35                  40                  45
Asn Pro Tyr Asn Gly Asn Lys Glu Phe Ser Ala Lys Phe Gln Asp Arg
        50                  55                  60
Val Thr Phe Thr Ala Asp Thr Ser Ala Asn Thr Ala Tyr Met Glu Leu
 65                  70                  75                  80
Arg Ser Leu Arg Ser Ala Asp Thr Ala Val Tyr Tyr Cys Ala Arg Val
                85                  90                  95
Gly Pro Tyr Ser Trp Asp Asp Ser Pro Gln Asp Asn Tyr Tyr Met Asp
               100                 105                 110
Val Trp Gly Lys Gly Thr Thr Val Ile Val Ser Ser
           115                 120
```

(2) INFORMATION FOR SEQ ID NO: 48:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 48:

```
Leu Glu Gln Ser Gly Ala Glu Val Lys Lys Pro Gly Ala Ser Val Lys
 1               5                  10                  15
Val Ser Cys Gln Ala Ser Gly Tyr Arg Phe Ser Asn Tyr Thr Leu Gln
                20                  25                  30
Trp Val Arg Gln Ala Pro Gly Gln Arg Phe Glu Trp Met Gly Trp Ile
            35                  40                  45
Asn Pro Tyr Asn Gly Asn Lys Glu Phe Ser Ala Lys Phe Gln Asp Arg
        50                  55                  60
Val Thr Phe Thr Ala Asp Thr Ser Ala Asn Thr Ala Tyr Met Glu Leu
 65                  70                  75                  80
```

```
Arg Ser Leu Arg Ser Ala Asp Thr Ala Val T yr Tyr Cys Ala Arg Val
            85                  90                  95

Gly Pro Tyr Ser Trp Asp Asp Ser Pro Gln A sp Asn Tyr Tyr Met Asp
            100                 105                 110

Val Trp Gly Lys Gly Thr Thr Val Ile Val S er Ser
            115                 120

(2) INFORMATION FOR SEQ ID NO: 49:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 49:

Leu Glu Gln Ser Gly Ala Glu Val Lys Lys P ro Gly Ala Ser Val Lys
1           5                   10                  15

Val Ser Cys Gln Ala Ser Gly Tyr Arg Phe S er Asn Phe Thr Leu Ile
            20                  25                  30

Trp Val Arg Gln Ala Pro Gly Gln Arg Phe G lu Trp Met Gly Trp Ile
            35                  40                  45

Asn Pro Tyr Asn Gly Asn Lys Glu Phe Ser A la Lys Phe Gln Asp Arg
    50                  55                  60

Val Thr Phe Thr Ala Asp Thr Ser Ala Asn T hr Ala Tyr Met Glu Leu
65                  70                  75                  80

Arg Ser Leu Arg Ser Ala Asp Thr Ala Val T yr Tyr Cys Ala Arg Val
            85                  90                  95

Gly Pro Tyr Ser Trp Asp Asp Ser Pro Gln A sp Asn Tyr Tyr Met Asp
            100                 105                 110

Val Trp Gly Lys Gly Thr Thr Val Ile Val S er Ser
            115                 120

(2) INFORMATION FOR SEQ ID NO: 50:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 50:

Leu Glu Gln Ser Gly Ala Glu Val Lys Lys P ro Gly Ala Ser Val Lys
1           5                   10                  15

Val Ser Cys Gln Ala Ser Gly Tyr Arg Phe S er Asn Trp Thr Ile Met
            20                  25                  30

Trp Val Arg Gln Ala Pro Gly Gln Arg Phe G lu Trp Met Gly Trp Ile
            35                  40                  45

Asn Pro Tyr Asn Gly Asn Lys Glu Phe Ser A la Lys Phe Gln Asp Arg
    50                  55                  60

Val Thr Phe Thr Ala Asp Thr Ser Ala Asn T hr Ala Tyr Met Glu Leu
65                  70                  75                  80

Arg Ser Leu Arg Ser Ala Asp Thr Ala Val T yr Tyr Cys Ala Arg Val
            85                  90                  95

Gly Pro Tyr Ser Trp Asp Asp Ser Pro Gln A sp Asn Tyr Tyr Met Asp
            100                 105                 110
```

Val Trp Gly Lys Gly Thr Thr Val Ile Val S er Ser
    115                 120

(2) INFORMATION FOR SEQ ID NO: 51:

(i) SEQUENCE CHARACTERISTICS:
        (A) LENGTH: 6166 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO: 51:

| | | | | | |
|---|---|---|---|---|---|
| TAATGCGGTA | GTTTATCACA | GTTAAATTGC | TAACGCAGTC | AGGCACCGTG T | ATGAAATCT | 60 |
| AACAATGCGC | TCATCGTCAT | CCTCGGCACC | GTCACCCTGG | ATGCTGTAGG C | ATAGGCTTG | 120 |
| GTTATGCCGG | TACTGCCGGG | CCTCTTGCGG | GATATCGTCC | ATTCCGACAG C | ATCGCCAGT | 180 |
| CACTATGGCG | TGCTGCTAGC | GCTATATGCG | TTGATGCAAT | TTCTATGCGC A | CCCGTTCTC | 240 |
| GGAGCACTGT | CCGACCGCTT | TGGCCGCCGC | CCAGTCCTGC | TCGCTTCGCT A | CTTGGAGCC | 300 |
| ACTATCGACT | ACGCGATCAT | GGCGACCACA | CCCGTCCTGT | GGATCCTCTA C | GCCGGACGC | 360 |
| ATCGTGGCCG | GCATCACCGG | CGCCACAGGT | GCGGTTGCTG | GCGCCTATAT C | GCCGACATC | 420 |
| ACCGATGGGG | AAGATCGGGC | TCGCCACTTC | GGGCTCATGA | GCGCTTGTTT C | GGCGTGGGT | 480 |
| ATGGTGGCAG | GCCCCGTGGC | CGGGGGACTG | TTGGGCGCCA | TCTCCTTGCA T | GCACCATTC | 540 |
| CTTGCGGCGG | CGGTGCTCAA | CGGCCTCAAC | CTACTACTGG | GCTGCTTCCT A | ATGCAGGAG | 600 |
| TCGCATAAGG | GAGAGCGTCG | ACCGATGCCC | TTGAGAGCCT | TCAACCCAGT C | AGCTCCTTC | 660 |
| CGGTGGGCGC | GGGGCATGAC | TATCGTCGCC | GCACTTATGA | CTGTCTTCTT T | ATCATGCAA | 720 |
| CTCGTAGGAC | AGGTGCCGGC | AGCGCTCTGG | GTCATTTTCG | GCGAGGACCG C | TTTCGCTGG | 780 |
| AGCGCGACGA | TGATCGGCCT | GTCGCTTGCG | GTATTCGGAA | TCTTGCACGC C | CTCGCTCAA | 840 |
| GCCTTCGTCA | CTGGTCCCGC | CACCAAACGT | TTCGGCGAGA | AGCAGGCCAT T | ATCGCCGGC | 900 |
| ATGGCGGCCG | ACGCGCTGGG | CTACGTCTTG | CTGGCGTTCG | CGACGCGAGG C | TGGATGGCC | 960 |
| TTCCCCATTA | TGATTCTTCT | CGCTTCCGGC | GGCATCGGGA | TGCCCGCGTT G | CAGGCCATG | 1020 |
| CTGTCCAGGC | AGGTAGATGA | CGACCATCAG | GGACAGCTTC | AAGGATCGCT C | GCGGCTCTT | 1080 |
| ACCAGCCTAA | CTTCGATCAC | TGGACCGCTG | ATCGTCACGG | CGATTTATGC C | GCCTCGGCG | 1140 |
| AGCACATGGA | ACGGGTTGGC | ATGGATTGTA | GGCGCCGCCC | TATACCTTGT C | TGCCTCCCC | 1200 |
| GCGTTGCGTC | GCGGTGCATG | GAGCCGGGCC | ACCTCGACCT | GAATGGAAGC C | GGCGGCACC | 1260 |
| TCGCTAACGG | ATTCACCACT | CCAAGAATTG | GAGCCAATCA | ATTCTTGCGG A | GAACTGTGA | 1320 |
| ATGCGCAAAC | CAACCCTTGG | CAGAACATAT | CCATCGCGTC | CGCCATCTCC A | GCAGCCGCA | 1380 |
| CGCGGCGCAT | CTCGGGCAGC | GTTGGGTCCT | GGCCACGGGT | GCGCATGATC G | TGCTCCTGT | 1440 |
| CGTTGAGGAC | CCGGCTAGGC | TGGCGGGGTT | GCCTTACTGG | TTAGCAGAAT G | AATCACCGA | 1500 |
| TACGCGAGCG | AACGTGAAGC | GACTGCTGCT | GCAAAACGTC | TGCGACCTGA G | CAACAACAT | 1560 |
| GAATGGTCTT | CGGTTTCCGT | GTTTCGTAAA | GTCTGGAAAC | GCGGAAGTCA G | CGCCCTGCA | 1620 |
| CCATTATGTT | CCGGATCTGC | ATCGCAGGAT | GCTGCTGGCT | ACCCTGTGGA A | CACCTACAT | 1680 |
| CTGTATTAAC | GAAGCGCTGG | CATTGACCCT | GAGTGATTTT | TCTCTGGTCC C | GCCGCATCC | 1740 |
| ATACCGCCAG | TTGTTTACCC | TCACAACGTT | CCAGTAACCG | GCATGTTCA T | CATCAGTAA | 1800 |
| CCCGTATCGT | GAGCATCCTC | TCTCGTTTCA | TCGGTATCAT | TACCCCCATG A | ACAGAAATT | 1860 |
| CCCCCTTACA | CGGAGGCATC | AAGTGACCAA | ACAGGAAAAA | ACCGCCCTTA A | CATGGCCCG | 1920 |

```
CTTTATCAGA AGCCAGACAT TAACGCTTCT GGAGAAACTC AACGAGCTGG A CGCGGATGA    1980

ACAGGCAGAC ATCTGTGAAT CGCTTCACGA CCACGCTGAT GAGCTTTACC G CAGCTGCCT    2040

CGCGCGTTTC GGTGATGACG GTGAAAACCT CTGACACATG CAGCTCCGG A GACGGTCAC     2100

AGCTTGTCTG TAAGCGGATG CCGGGAGCAG ACAAGCCCGT CAGGGCGCGT C AGCGGGTGT    2160

TGGCGGGTGT CGGGGCGCAG CCATGACCCA GTCACGTAGC GATAGCGGAG T GTATACTGG    2220

CTTAACTATG CGGCATCAGA GCAGATTGTA CTGAGAGTGC ACCATATGCG G TGTGAAATA    2280

CCGCACAGAT GCGTAAGGAG AAAATACCGC ATCAGGCGCT CTTCCGCTTC C TCGCTCACT    2340

GACTCGCTGC GCTCGGTCGT TCGGCTGCGG CGAGCGGTAT CAGCTCACTC A AAGGCGGTA    2400

ATACGGTTAT CCACAGAATC AGGGGATAAC GCAGGAAAGA ACATGTGAGC A AAAGGCCAG    2460

CAAAAGGCCA GGAACCGTAA AAAGGCCGCG TTGCTGGCGT TTTTCCATAG G CTCCGCCGC    2520

CCTGACGAGC ATCACAAAAA TCGACGCTCA AGTCAGAGGT GGCGAAACCC G ACAGGACTA    2580

TAAAGATACC AGGCGTTTCC CCCTGGAAGC TCCCTCGTGC GCTCTCCTGT T CCGACCCTG    2640

CCGCTTACCG GATACCTGTC CGCCTTTCTC CCTTCGGGAA GCGTGGCGCT T TCTCATAGC    2700

TCACGCTGTA GGTATCTCAG TTCGGTGTAG GTCGTTCGCT CCAAGCTGGG C TGTGTGCAC    2760

GAACCCCCCG TTCAGCCCGA CCGCTGCGCC TTATCCGGTA ACTATCGTCT T GAGTCCAAC    2820

CCGGTAAGAC ACGACTTATC GCCACTGGCA GCAGCCACTG GTAACAGGAT T AGCAGAGCG    2880

AGGTATGTAG CGGTGCTAC AGAGTTCTTG AAGTGGTGGC CTAACTACGG C TACACTAGA    2940

AGGACAGTAT TTGGTATCTG CGCTCTGCTG AAGCCAGTTA CCTTCGGAAA A AGAGTTGGT    3000

AGCTCTTGAT CCGGCAAACA AACCACCGCT GGTAGCGGTG GTTTTTTTGT T TGCAAGCAG    3060

CAGATTACGC GCAGAAAAAA AGGATCTCAA GAAGATCCTT TGATCTTTTC T ACGGGTCT     3120

GACGCTCAGT GGAACGAAAA CTCACGTTAA GGGATTTTGG TCATGAGATT A TCAAAAAGG    3180

ATCTTCACCT AGATCCTTTT AAATTAAAAA TGAAGTTTTA AATCAATCTA A AGTATATAT    3240

GAGTAAACTT GGTCTGACAG TTACCAATGC TTAATCAGTG AGGCACCTAT C TCAGCGATC    3300

TGTCTATTTC GTTCATCCAT AGTTGCCTGA CTCCCCGTCG TGTAGATAAC T ACGATACGG    3360

GAGGGCTTAC CATCTGGCCC CAGTGCTGCA ATGATACCGC GAGACCCACG C TCACCGGCT    3420

CCAGATTTAT CAGCAATAAA CCAGCCAGCC GGAAGGGCCG AGCGCAGAAG T GGTCCTGCA    3480

ACTTATCCG CCTCCATCCA GTCTATTAAT TGTTGCCGGG AAGCTAGAGT A AGTAGTTCG    3540

CCAGTTAATA GTTTGCGCAA CGTTGTTGCC ATTGCTGCAG GCATCGTGGT G TCACGCTCG    3600

TCGTTTGGTA TGGCTTCATT CAGCTCCGGT TCCCAACGAT CAAGGCGAGT T ACATGATCC    3660

CCCATGTTGT GCAAAAAAGC GGTTAGCTCC TTCGGTCCTC CGATCGTTGT C AGAAGTAAG    3720

TTGGCCGCAG TGTTATCACT CATGGTTATG GCAGCACTGC ATAATTCTCT T ACTGTCATG    3780

CCATCCGTAA GATGCTTTTC TGTGACTGGT GAGTACTCAA CCAAGTCATT C TGAGAATAG    3840

TGTATGCGGC GACCGAGTTG CTCTTGCCCG GCGTCAACAC GGGATAATAC C GCGCCACAT    3900

AGCAGAACTT TAAAAGTGCT CATCATTGGA AAACGTTCTT CGGGGCGAAA A CTCTCAAGG    3960

ATCTTACCGC TGTTGAGATC CAGTTCGATG TAACCCACTC GTGCACCCAA C TGATCTTCA    4020

GCATCTTTTA CTTTCACCAG CGTTTCTGGG TGAGCAAAAA CAGGAAGGCA A AATGCCGCA    4080

AAAAAGGGAA TAAGGGCGAC ACGGAAATGT TGAATACTCA TACTCTTCCT T TTTCAATAT    4140

TATTGAAGCA TTTATCAGGG TTATTGTCTC ATGAGCGGAT ACATATTTGA A TGTATTTAG    4200

AAAAATAAAC AAATAGGGGT TCCGCGCACA TTTCCCCGAA AAGTGCCACC T GACGTCCTG    4260
```

```
CAGTGGAGAT TATCGTCACT GCAATGCTTC GCAATATGGC GCAAAATGAC C AACAGCGGT      4320

TGATTGATCA GGTAGAGGGG GCGCTGTACG AGGTAAAGCC CGATGCCAGC A TTCCTGACG      4380

ACGATACGGA GCTGCTGCGC GATTACGTAA AGAAGTTATT GAAGCATCCT C GTCAGTAAA      4440

AAGTTAATCT TTTCAACAGC TGTCATAAAG TTGTCACGGC CGAGACTTAT A GTCGCTTTG      4500

TTTTTATTTT TTAATGTATT GAATTCAGGA GGAATTTAAA ATGAAAAAGA C AGCTATCGC      4560

GATTGCAGTG GCACTGGCTG GTTTCGCTAC CGTGGCCCAG GCGGCCGAGC T CACGCAGTC      4620

TCCAGGCACC CTGTCTTTGT CTCCAGGGGA AAGAGCCACC CTCTCCTGCA G GGCCAGTCA      4680

CAGTGTTAGC AGGGCCTACT TAGCCTGGTA CCAGCAGAAA CCTGGCCAGG C TCCCAGGCT      4740

CCTCATCTAT GGTACATCCA GCAGGGCCAC TGGCATCCCA GACAGGTTCA G TGGCAGTGG      4800

GTCTGGGACA GACTTCACTC TCACCATCAG CAGACTGGAG CCTGAAGATT T TGCAGTGTA      4860

CTACTGTCAG CAGTATGGTG GCTCACCGTG GTTCGGCCAA GGGACCAAGG T GGAACTCAA      4920

ACGAACTGTG GCTGCACCAT CTGTCTTCAT CTTCCCGCCA TCTGATGAGC A GTTGAAATC      4980

TGGAACTGCC TCTGTTGTGT GCCTGCTGAA TAACTTCTAT CCCAGAGAGG C CAAAGTACA      5040

GTGGAAGGTG GATAACGCCC TCCAATCGGG TAACTCCCAG GAGAGTGTCA C AGAGCAGGA      5100

CAGCAAGGAC AGCACCTACA GCCTCAGCAG CACCCTGACG CTGAGCAAAG C AGACTACGA      5160

GAAACACAAA GTCTACGCCT GCGAAGTCAC CCATCAGGGC CTGAGTTCGC C CGTCACAAA      5220

GAGCTTCAAC AGGGGAGAGT GTTAATTCTA GATAATTAAT TAGGAGGAAT T TAAAATGAA      5280

ATACCTATTG CCTACGGCAG CCGCTGGATT GTTATTACTC GCTGCCCAAC C AGCCATGGC      5340

CGAGGTGCAG CTGCTCGAGC AGTCTGGGGC TGAGGTGAAG AAGCCTGGGT C CTCGGTGAA      5400

GGTCTCCTGC AGGGCTTCTG GAGGCACCTT CAACAATTAT GCCATCAGCT G GGTGCGACA      5460

GGCCCCTGGA CAAGGGCTTG AGTGGATGGG AGGGATCTTC CCTTTCCGTA A TACAGCAAA      5520

GTACGCACAA CACTTCCAGG GCAGAGTCAC CATTACCGCG GACGAATCCA C GGGCACAGC      5580

CTACATGGAG CTGAGCAGCC TGAGATCTGA GGACACGGCC ATATATTATT G TGCGAGAGG      5640

GGATACGATT TTTGGAGTGA CCATGGGATA CTACGCTATG GACGTCTGGG G CCAAGGGAC      5700

CACGGTCACC GTCTCCGCAG CCTCCACCAA GGGCCCATCG GTCTTCCCCC T GGCACCCTC      5760

CTCCAAGAGC ACCTCTGGGG GCACAGCGGC CCTGGGCTGC CTGGTCAAGG A CTACTTCCC      5820

CGAACCGGTG ACGGTGTCGT GGAACTCAGG CGCCCTGACC AGCGGCGTGC A CACCTTCCC      5880

GGCTGTCCTA CAGTCCTCAG GACTCTACTC CCTCAGCAGC GTGGTGACCG T GCCCTCCAG      5940

CAGCTTGGGC ACCCAGACCT ACATCTGCAA CGTGAATCAC AAGCCCAGCA A CACCAAGGT      6000

GGACAAGAAA GCAGAGCCCA AATCTTGTGA CAAAACTAGT GGCCAGGCCG G CCAGTAATT      6060

AATTAGCCCG CCTAATGAGC GGGCTTTTTT TTAAGCGGCC GCTTATCATC G ATAAGCTTT      6120

CGTCTTCAAG ATTTCTCATG TTTGACAGCT TATCATCGAT AAGCTT            6166
```

(2) INFORMATION FOR SEQ ID NO: 52:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

```
CCAGACGTCC ATATAATAAT TGTCMNNMNN MNNMNNMNNC CAACCCCACT C CCCCACTCT        60
```

(2) INFORMATION FOR SEQ ID NO: 53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

GACAATTATT ATATGGACGT CTGG                                               24

(2) INFORMATION FOR SEQ ID NO: 54:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 54:

Leu Glu Gln Ser Gly Ala Glu Val Lys Lys Pro Gly Ala Ser Val Lys
1               5                   10                  15

Val Ser Cys Gln Ala Ser Gly Tyr Arg Phe Ser Asn Phe Thr Val His
            20                  25                  30

Trp Val Arg Gln Ala Pro Gly Gln Arg Phe Glu Trp Met Gly Trp Ile
        35                  40                  45

Asn Pro Tyr Asn Gly Asn Lys Glu Phe Ser Ala Lys Phe Gln Asp Arg
    50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Glu Trp Gly Trp Glu Gln Phe Arg Phe Asp Asn Tyr Tyr Met Asp
            100                 105                 110

Val Trp Gly Lys Gly Thr Thr Val Ile Val Ser Ser
        115                 120

(2) INFORMATION FOR SEQ ID NO: 55:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 55:

Leu Glu Gln Ser Gly Ala Glu Val Lys Lys Pro Gly Ala Ser Val Lys
1               5                   10                  15

Val Ser Cys Gln Ala Ser Gly Tyr Arg Phe Ser Asn Phe Thr Val His
            20                  25                  30

Trp Val Arg Gln Ala Pro Gly Gln Arg Phe Glu Trp Met Gly Trp Ile
        35                  40                  45

Asn Pro Tyr Asn Gly Asn Lys Glu Phe Ser Ala Lys Phe Gln Asp Arg
    50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val

```
                    85                  90                  95
Gly Glu Trp Gly Trp Glu Met Phe Arg Tyr Asp Asn Tyr Tyr Met Asp
                100                 105                 110
Val Trp Gly Lys Gly Thr Thr Val Ile Val Ser Ser
            115                 120
```

(2) INFORMATION FOR SEQ ID NO: 56:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 56:

```
Leu Glu Gln Ser Gly Ala Glu Val Lys Lys Pro Gly Ala Ser Val Lys
1               5                   10                  15
Val Ser Cys Gln Ala Ser Gly Tyr Arg Phe Ser Asn Phe Thr Val His
                20                  25                  30
Trp Val Arg Gln Ala Pro Gly Gln Arg Phe Glu Trp Met Gly Trp Ile
                35                  40                  45
Asn Pro Tyr Asn Gly Asn Lys Glu Phe Ser Ala Lys Phe Gln Asp Arg
            50                  55                  60
Val Thr Phe Thr Ala Asp Thr Ser Ala Asn Thr Ala Tyr Met Glu Leu
65                  70                  75                  80
Arg Ser Leu Arg Ser Ala Asp Thr Ala Val Tyr Tyr Cys Ala Arg Val
                85                  90                  95
Gly Glu Trp Gly Trp Glu Met Arg Phe Asp Asn Tyr Tyr Met Asp
                100                 105                 110
Val Trp Gly Lys Gly Thr Thr Val Ile Val Ser Ser
            115                 120
```

(2) INFORMATION FOR SEQ ID NO: 57:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 57:

```
Leu Glu Gln Ser Gly Ala Glu Val Lys Lys Pro Gly Ala Ser Val Lys
1               5                   10                  15
Val Ser Cys Gln Ala Ser Gly Tyr Arg Phe Ser Asn Phe Thr Val His
                20                  25                  30
Trp Val Arg Gln Ala Pro Gly Gln Arg Phe Glu Trp Met Gly Trp Ile
                35                  40                  45
Asn Pro Tyr Asn Gly Asn Lys Glu Phe Ser Ala Lys Phe Gln Asp Arg
            50                  55                  60
Val Thr Phe Thr Ala Asp Thr Ser Ala Asn Thr Ala Tyr Met Glu Leu
65                  70                  75                  80
Arg Ser Leu Arg Ser Ala Asp Thr Ala Val Tyr Tyr Cys Ala Arg Val
                85                  90                  95
Gly Glu Trp Gly Trp His Gln Arg Arg Tyr Asp Asn Tyr Tyr Met Asp
                100                 105                 110
Val Trp Gly Lys Gly Thr Thr Val Ile Val Ser Ser
            115                 120
```

(2) INFORMATION FOR SEQ ID NO: 58:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 58:

```
Leu Glu Gln Ser Gly Ala Glu Val Lys Lys Pro Gly Ala Ser Val Lys
1               5                   10                  15

Val Ser Cys Gln Ala Ser Gly Tyr Arg Phe Ser Asn Phe Thr Val His
            20                  25                  30

Trp Val Arg Gln Ala Pro Gly Gln Arg Phe Glu Trp Met Gly Trp Ile
        35                  40                  45

Asn Pro Tyr Asn Gly Asn Lys Glu Phe Ser Ala Lys Phe Gln Asp Arg
    50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Glu Trp Gly Trp Thr Gln Arg Arg Phe Asp Asn Tyr Tyr Met Asp
                100                 105                 110

Val Trp Gly Lys Gly Thr Thr Val Ile Val Ser Ser
                115                 120
```

(2) INFORMATION FOR SEQ ID NO: 59:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 59:

```
Leu Glu Gln Ser Gly Ala Glu Val Lys Lys Pro Gly Ala Ser Val Lys
1               5                   10                  15

Val Ser Cys Gln Ala Ser Gly Tyr Arg Phe Ser Asn Phe Thr Val His
            20                  25                  30

Trp Val Arg Gln Ala Pro Gly Gln Arg Phe Glu Trp Met Gly Trp Ile
        35                  40                  45

Asn Pro Tyr Asn Gly Asn Lys Glu Phe Ser Ala Lys Phe Gln Asp Arg
    50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Glu Trp Gly Trp Asp Gln Val Arg Tyr Asp Asn Tyr Tyr Met Asp
                100                 105                 110

Val Trp Gly Lys Gly Thr Thr Val Ile Val Ser Ser
                115                 120
```

(2) INFORMATION FOR SEQ ID NO: 60:

(i) SEQUENCE CHARACTERISTICS:
        (A) LENGTH: 124 amino acids
        (B) TYPE: amino acid (D) TOPOLOGY: linear (ii) MOLECULE TYPE: protein (xi) SEQUENCE DESCRIPTION: SEQ ID NO: 60:

Leu Glu Gln Ser Gly Ala Glu Val Lys Lys Pro Gly Ala Ser Val Lys
1               5                  10                  15

Val Ser Cys Gln Ala Ser Gly Tyr Arg Phe Ser Asn Phe Thr Val His
            20                  25                  30

Trp Val Arg Gln Ala Pro Gly Gln Arg Phe Glu Trp Met Gly Trp Ile
        35                  40                  45

Asn Pro Tyr Asn Gly Asn Lys Glu Phe Ser Ala Lys Phe Gln Asp Arg
    50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Glu Trp Gly Trp Asp Gln Arg Arg Tyr Asp Asn Tyr Tyr Met Asp
            100                 105                 110

Val Trp Gly Lys Gly Thr Thr Val Ile Val Ser Ser
        115                 120

(2) INFORMATION FOR SEQ ID NO: 61:

(i) SEQUENCE CHARACTERISTICS:
         (A) LENGTH: 124 amino acids
         (B) TYPE: amino acid
         (D) TOPOLOGY: linear (ii) MOLECULE TYPE: protein (xi) SEQUENCE DESCRIPTION: SEQ ID NO: 61:

Leu Glu Gln Ser Gly Ala Glu Val Lys Lys Pro Gly Ala Ser Val Lys
1               5                  10                  15

Val Ser Cys Gln Ala Ser Gly Tyr Arg Phe Ser Asn Phe Thr Val His
            20                  25                  30

Trp Val Arg Gln Ala Pro Gly Gln Arg Phe Glu Trp Met Gly Trp Ile
        35                  40                  45

Asn Pro Tyr Asn Gly Asn Lys Glu Phe Ser Ala Lys Phe Gln Asp Arg
    50                  55                  60

Val Thr Phe Thr Ala Asp Thr Ser Ala Asn Thr Ala Tyr Met Glu Leu
65                  70                  75                  80

Arg Ser Leu Arg Ser Ala Asp Thr Ala Val Tyr Tyr Cys Ala Arg Val
                85                  90                  95

Gly Glu Trp Gly Trp Glu Met Ala Ile Gln Asp Asn Tyr Tyr Met Asp
            100                 105                 110

Val Trp Gly Lys Gly Thr Thr Val Ile Val Ser Ser
        115                 120

(2) INFORMATION FOR SEQ ID NO: 62:

(i) SEQUENCE CHARACTERISTICS:
         (A) LENGTH: 324 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 62:

```
GAGCTCACGC AGTCTCCAGG CACCCTGTCT CTGTCTCCAG GGGAAAGAGC C ACCTTCTCC      60

TGTAGGTCCA GTCACAGCAT TCGCAGCCGC CGCGTAGCCT GGTACCAGCA C AAACCTGGC     120

CAGGCTCCAA GGCTGGTCAT ACATGGTGTT TCCAATAGGG CCTCTGGCAT C TCAGACAGG     180

TTCAGCGGCA GTGGGTCTGG GACAGACTTC ACTCTCACCA TCACCAGAGT G GAGCCTGAA     240

GACTTTGCAC TGTACTACTG TCAGGTCTAT GGTGCCTCCT CGTACACTTT T GGCCAGGGG     300

ACCAAACTGG AGAGGAAACG AACT                                              324
```

(2) INFORMATION FOR SEQ ID NO: 63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

```
GAATTCTAAA CTAGCTAGTC G                                                  21
```

(2) INFORMATION FOR SEQ ID NO: 64:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

```
AGGTTTGTGC TGGTACCAGG CTACMNNMNN MNNMNNMNNM NNGTGACTGG A CCTACAGGA      60

GAAGGT                                                                   66
```

(2) INFORMATION FOR SEQ ID NO: 65:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

```
GTAGCCTGGT ACCAGCACAA ACCT                                               24
```

(2) INFORMATION FOR SEQ ID NO: 66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

```
AATACGACTC ACTATAGGGC G                                                  21
```

(2) INFORMATION FOR SEQ ID NO: 67:

(i) SEQUENCE CHARACTERISTICS:
        (A) LENGTH: 108 amino acids (B) TYPE: amino acid
            (D) TOPOLOGY: linear (ii) MOLECULE TYPE: protein (xi) SEQUENCE DESCRIPTION: SEQ ID NO: 67:

Glu Leu Thr Gln Ser Pro Gly Thr Leu Ser Leu Ser Pro Gly Glu Arg
1               5                   10                  15

Ala Thr Phe Ser Cys Arg Ser Ser His Lys Glu Phe Gly Arg Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Val Tyr Gly Ala Ser Ser Tyr Thr
                85                  90                  95

Phe Gly Gln Gly Thr Lys Leu Glu Arg Lys Arg Thr
            100                 105

(2) INFORMATION FOR SEQ ID NO: 68:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 68:

Glu Leu Thr Gln Ser Pro Gly Thr Leu Ser Leu Ser Pro Gly Glu Arg
1               5                   10                  15

Ala Thr Phe Ser Cys Arg Ser Ser His Thr Val Tyr Arg Asp Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Val Tyr Gly Ala Ser Ser Tyr Thr
                85                  90                  95

Phe Gly Gln Gly Thr Lys Leu Glu Arg Lys Arg Thr
            100                 105

(2) INFORMATION FOR SEQ ID NO: 69:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 69:

Glu Leu Thr Gln Ser Pro Gly Thr Leu Ser Leu Ser Pro Gly Glu Arg
1               5                   10                  15

Ala Thr Phe Ser Cys Arg Ser Ser His Pro Leu His Arg Ala Arg Val
                20                  25                  30

Ala Trp Tyr Gln His Lys Pro Gly Gln Ala Pro Arg Leu Val Ile His
         35                  40                  45

Gly Val Ser Asn Arg Ala Ser Gly Ile Ser Asp Arg Phe Ser Gly Ser
         50                  55                  60

Gly Ser Gly Thr Asp Phe Thr Leu Thr Ile Thr Arg Val Glu Pro Glu
65                   70                  75                  80

Asp Phe Ala Leu Tyr Tyr Cys Gln Gln Tyr Gly Trp Pro Phe Tyr Thr
                 85                  90                  95

Phe Gly Gln Gly Thr Lys Leu Glu Arg Lys Arg Thr
            100                 105

(2) INFORMATION FOR SEQ ID NO: 70:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 70:

Glu Leu Thr Gln Ser Pro Gly Thr Leu Ser Leu Ser Pro Gly Glu Arg
1                5                  10                  15

Ala Thr Phe Ser Cys Arg Ser Ser His Gln Leu Asp Gly Ser Arg Val
             20                  25                  30

Ala Trp Tyr Gln His Lys Pro Gly Gln Ala Pro Arg Leu Val Ile His
         35                  40                  45

Gly Val Ser Asn Arg Ala Ser Gly Ile Ser Asp Arg Phe Ser Gly Ser
         50                  55                  60

Gly Ser Gly Thr Asp Phe Thr Leu Thr Ile Thr Arg Val Glu Pro Glu
65                   70                  75                  80

Asp Phe Ala Leu Tyr Tyr Cys Gln Val Tyr Gly Ala Ser Ser Tyr Thr
                 85                  90                  95

Phe Gly Gln Gly Thr Lys Leu Glu Arg Lys Arg Thr
            100                 105

(2) INFORMATION FOR SEQ ID NO: 71:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

CAGTTTGGTC CCCTGGCCAA AAGTGTAMNN MNNMNNMNNA TAMNNCTGAC A GTAGTACAG      60

TGCAAAGTC      69

(2) INFORMATION FOR SEQ ID NO: 72:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 72:

TACACTTTTG GCCAGGGGAC CAAACTG      27

(2) INFORMATION FOR SEQ ID NO: 73:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 73:

```
Glu Leu Thr Gln Ser Pro Gly Thr Leu Ser Leu Ser Pro Gly Glu Agr
 1               5                  10                  15

Ala Thr Phe Ser Cys Arg Ser Ser His Ser Ile Arg Ser Arg Arg Val
            20                  25                  30

Ala Trp Tyr Gln His Lys Pro Gly Gln Ala Pro Arg Leu Val Ile His
        35                  40                  45

Gly Val Ser Asn Arg Ala Ser Gly Ile Ser Asp Arg Phe Ser Gly Ser
    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Gln Tyr Gly Trp Pro Phe Tyr Thr
                85                  90                  95

Phe Gly Gln Gly Thr Lys Leu Glu Arg Lys Arg Thr
                100                 105
```

(2) INFORMATION FOR SEQ ID NO: 74:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 74:

```
Glu Leu Thr Gln Ser Pro Gly Thr Leu Ser Leu Ser Pro Gly Glu Arg
 1               5                  10                  15

Ala Thr Phe Ser Cys Arg Ser Ser His Ser Ile Arg Ser Arg Arg Val
            20                  25                  30

Ala Trp Tyr Gln His Lys Pro Gly Gln Ala Pro Arg Leu Val Ile His
        35                  40                  45

Gly Val Ser Asn Arg Ala Ser Gly Ile Ser Asp Arg Phe Ser Gly Ser
    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Val Tyr Gly Gly Ser Ala Tyr Thr
                85                  90                  95

Phe Gly Gln Gly Thr Lys Leu Glu Arg Lys Arg Thr
                100                 105
```

(2) INFORMATION FOR SEQ ID NO: 75:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 75:

Glu Leu Thr Gln Ser Pro Gly Thr Leu Ser Leu Ser Pro Gly Glu Arg
1               5                   10                  15

Ala Thr Phe Ser Cys Arg Ser Ser His Ser Ile Arg Ser Arg Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Lys Tyr Gly Gly Gly Thr Tyr Thr
                85                  90                  95

Phe Gly Gln Gly Thr Lys Leu Glu Arg Lys Arg Thr
                100                 105

(2) INFORMATION FOR SEQ ID NO: 76:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 76:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Val Tyr Gly Trp Ser Gln Tyr Thr
                85                  90                  95

Phe Gly Gln Gly Thr Lys Leu Glu Arg Lys Arg Thr
                100                 105

(2) INFORMATION FOR SEQ ID NO: 77:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 77:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu

```
                65                  70                  75                  80
Asp Phe Ala Leu Tyr Tyr Cys Gln Leu Tyr Gly Arg Gly Asn Tyr Thr
                    85                  90                  95

Phe Gly Gln Gly Thr Lys Leu Glu Arg Lys Arg Thr
                100                 105
```

(2) INFORMATION FOR SEQ ID NO: 78:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 78:

```
Glu Leu Thr Gln Ser Pro Gly Thr Leu Ser Leu Ser Pro Gly Glu Arg
1                   5                   10                  15

Ala Thr Phe Ser Cys Arg Ser Ser His Gln Leu Asp Gly Ser Arg Val
                    20                  25                  30

Ala Trp Tyr Gln His Lys Pro Gly Gln Ala Pro Arg Leu Val Ile His
                    35                  40                  45

Gly Val Ser Asn Arg Ala Ser Gly Ile Ser Asp Arg Phe Ser Gly Ser
                    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Thr Tyr Gly Arg Gly Val Tyr Thr
                    85                  90                  95

Phe Gly Gln Gly Thr Lys Leu Glu Arg Lys Arg Thr
                100                 105
```

(2) INFORMATION FOR SEQ ID NO: 79:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 79:

```
Glu Leu Thr Gln Ser Pro Gly Thr Leu Ser Leu Ser Pro Gly Glu Arg
1                   5                   10                  15

Ala Thr Phe Ser Cys Arg Ser Ser His Gln Leu Asp Gly Ser Arg Val
                    20                  25                  30

Ala Trp Tyr Gln His Lys Pro Gly Gln Ala Pro Arg Leu Val Ile His
                    35                  40                  45

Gly Val Ser Asn Arg Ala Ser Gly Ile Ser Asp Arg Phe Ser Gly Ser
                    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Ser Tyr Gly Gly Arg Asp Tyr Thr
                    85                  90                  95

Phe Gly Gln Gly Thr Lys Leu Glu Arg Lys Arg Thr
                100                 105
```

(2) INFORMATION FOR SEQ ID NO: 80:

(i) SEQUENCE CHARACTERISTICS:
        (A) LENGTH: 108 amino acids (B) TYPE: amino acid
            (D) TOPOLOGY: linear (ii) MOLECULE TYPE: protein (xi) SEQUENCE DESCRIPTION: SEQ ID NO: 80:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Thr Tyr Gly Trp Ser Gly Tyr Thr
                85                  90                  95

Phe Gly Gln Gly Thr Lys Leu Glu Arg Lys Arg Thr
                100                 105

(2) INFORMATION FOR SEQ ID NO: 81:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 81:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Lys Tyr Gly Asp Ser Phe Tyr Thr
                85                  90                  95

Phe Gly Gln Gly Thr Lys Leu Glu Arg Lys Arg Thr
                100                 105

(2) INFORMATION FOR SEQ ID NO: 82:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 82:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Met Tyr Gly Gly Arg Asp Tyr Thr
                85                  90                  95

Phe Gly Gln Gly Thr Lys Leu Glu Arg Lys Arg Thr
                100                 105

(2) INFORMATION FOR SEQ ID NO: 83:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 83:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Gln Tyr Gly Asp Ser Leu Tyr Thr
                85                  90                  95

Phe Gly Gln Gly Thr Lys Leu Glu Arg Lys Arg Thr
                100                 105

(2) INFORMATION FOR SEQ ID NO: 84:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 84:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Met Tyr Gly Gly Phe Thr Tyr Thr
                85                  90                  95

Phe Gly Gln Gly Thr Lys Leu Glu Arg Lys Arg Thr (2) INFORMATION FOR SEQ ID NO: 85:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 85:

```
Glu Leu Thr Gln Ser Pro Gly Thr Leu Ser Leu Ser Pro Gly Glu Arg
 1               5                  10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Thr Tyr Gly Arg Gly Ser Tyr Thr
                85                  90                  95

Phe Gly Gln Gly Thr Lys Leu Glu Arg Lys Arg Thr
                100                 105
```

(2) INFORMATION FOR SEQ ID NO: 86:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 86:

```
Glu Leu Thr Gln Ser Pro Gly Thr Leu Ser Leu Ser Pro Gly Glu Arg
 1               5                  10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Thr Tyr Gly Arg Gly His Tyr Thr
                85                  90                  95

Phe Gly Gln Gly Thr Lys Leu Glu Arg Lys Arg Thr
                100                 105
```

(2) INFORMATION FOR SEQ ID NO: 87:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 87:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Thr Tyr Gly Arg Gly Ile Tyr Thr
                85                  90                  95

Phe Gly Gln Gly Thr Lys Leu Glu Arg Lys Arg Thr
                100                 105

(2) INFORMATION FOR SEQ ID NO: 88:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO: 88:

Glu Leu Thr Gln Ser Pro Gly Thr Leu Ser Leu Ser Pro Gly Glu Arg
1               5                   10                  15

Ala Thr Phe Ser Cys Arg Ser Ser His Gln Leu Asp Gly Ser Arg Val
                20                  25                  30

Ala Trp Tyr Gln His Lys Pro Gly Gln Ala Pro Arg Leu Val Ile His
            35                  40                  45

Gly Val Ser Asn Arg Ala Ser Gly Ile Ser Asp Arg Phe Ser Gly Ser
        50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Gln Tyr Gly Trp Pro Phe Tyr Thr
                85                  90                  95

Phe Gly Gln Gly Thr Lys Leu Glu Arg Lys Arg Thr
                100                 105

(2) INFORMATION FOR SEQ ID NO: 89:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 89:

Leu Glu Gln Ser Gly Ala Glu Val Lys Lys Pro Gly Ala Ser Val Lys
1               5                   10                  15

Val Ser Cys Gln Ala Ser Gly Tyr Arg Phe Ser His Phe Thr Val His
                20                  25                  30

Trp Val Arg Gln Ala Pro Gly Gln Arg Phe Glu Trp His Gly Trp Ile
            35                  40                  45

Asn Pro Tyr Asn Gly Asn Lys Glu Phe Ser Ala Lys Phe Gln Asp Arg
        50                  55                  60

```
Val Thr Phe Thr Ala Asp Thr Ser Ala Asn Thr Ala Tyr Met Glu Leu
 65                  70                  75                  80

Arg Ser Leu Arg Ser Ala Asp Thr Ala Val Tyr Tyr Cys Ala Arg Val
                 85                  90                  95

Gly Glu Trp Gly Trp Glu Met Phe Arg Tyr Asp Asn Tyr Tyr Met Asp
            100                 105                 110

Val Trp Gly Lys Gly Thr Thr Val Ile Val Ser Ser
            115                 120

(2) INFORMATION FOR SEQ ID NO: 90:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 90:

Leu Glu Gln Ser Gly Ala Glu Val Lys Lys Pro Gly Ala Ser Val Lys
 1               5                  10                  15

Val Ser Cys Gln Ala Ser Gly Tyr Arg Phe Ser His Phe Thr Leu His
                 20                  25                  30

Trp Val Arg Gln Ala Pro Gly Gln Arg Phe Glu Trp His Gly Trp Ile
                35                  40                  45

Asn Pro Tyr Asn Gly Asn Lys Glu Phe Ser Ala Lys Phe Gln Asp Arg
             50                  55                  60

Val Thr Phe Thr Ala Asp Thr Ser Ala Asn Thr Ala Tyr Met Glu Leu
 65                  70                  75                  80

Arg Ser Leu Arg Ser Ala Asp Thr Ala Val Tyr Tyr Cys Ala Arg Val
                 85                  90                  95

Gly Glu Trp Gly Trp Glu Met Phe Arg Tyr Asp Asn Tyr Tyr Met Asp
            100                 105                 110

Val Trp Gly Lys Gly Thr Thr Val Ile Val Ser Ser
            115                 120

(2) INFORMATION FOR SEQ ID NO: 91:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 91:

Leu Glu Gln Ser Gly Ala Glu Val Lys Lys Pro Gly Ala Ser Val Lys
 1               5                  10                  15

Val Ser Cys Gln Ala Ser Gly Tyr Arg Phe Ser His Phe Thr Val His
                 20                  25                  30

Trp Val Arg Gln Ala Pro Gly Gln Arg Phe Glu Trp His Gly Trp Ile
                35                  40                  45

Asn Pro Tyr Asn Gly Asn Lys Glu Phe Ser Ala Lys Phe Gln Asp Arg
             50                  55                  60

Val Thr Phe Thr Ala Asp Thr Ser Ala Asn Thr Ala Tyr Met Glu Leu
 65                  70                  75                  80

Arg Ser Leu Arg Ser Ala Asp Thr Ala Val Tyr Tyr Cys Ala Arg Val
                 85                  90                  95

Gly Glu Trp Gly Trp His Gln Arg Arg Tyr Asp Asn Tyr Tyr Met Asp
```

```
                 100                 105                 110
Val Trp Gly Lys Gly Thr Thr Val Ile Val S er Ser
            115                 120
```

(2) INFORMATION FOR SEQ ID NO: 92:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 92:

```
Leu Glu Gln Ser Gly Ala Glu Val Lys Lys P ro Gly Ala Ser Val Lys
1               5                   10                  15

Val Ser Cys Gln Ala Ser Gly Tyr Arg Phe S er His Phe Thr Leu His
            20                  25                  30

Trp Val Arg Gln Ala Pro Gly Gln Arg Phe G lu Trp His Gly Trp Ile
            35                  40                  45

Asn Pro Tyr Asn Gly Asn Lys Glu Phe Ser A la Lys Phe Gln Asp Arg
        50                  55                  60

Val Thr Phe Thr Ala Asp Thr Ser Ala Asn T hr Ala Tyr Met Glu Leu
65                  70                  75                  80

Arg Ser Leu Arg Ser Ala Asp Thr Ala Val T yr Tyr Cys Ala Arg Val
                85                  90                  95

Gly Glu Trp Gly Trp His Gln Arg Arg Tyr A sp Asn Tyr Tyr Met Asp
                100                 105                 110

Val Trp Gly Lys Gly Thr Thr Val Ile Val S er Ser
            115                 120
```

What is claimed is:

1. A composition comprising a synthetic human monoclonal antibody capable of immunoreacting with and neutralizing human immunodeficiency virus (HIV), wherein the monoclonal antibody has the capacity to reduce HIV infectivity titer in an in vitro virus infectivity assay by 50% at a concentration of less than 100 nanograms (ng) of antibody per milliliter (ml) in a pharmacological carrier.

2. A kit useful for the detection of human immunodeficiency virus (HIV) in a source suspected of containing HIV, the kit comprising carrier means being compartmentalized to receive in close confinement therein one or more containers comprising a container containing a synthetic human monoclonal antibody capable of immunoreacting with and neutralizing human immunodeficiency virus (HIV), wherein the monoclonal antibody has the capacity to reduce HIV infectivity titer in an in vitro virus infectivity assay by 50% at a concentration of less than 100 nanograms (ng) of antibody per milliliter (ml).

3. The composition of claim 1 wherein said composition contains two or more different monoclonal antibodies.

* * * * *